US011773110B2

(12) United States Patent
Ho et al.

(10) Patent No.: US 11,773,110 B2
(45) Date of Patent: Oct. 3, 2023

(54) HETEROCYCLE AMINES AND USES THEREOF

(71) Applicant: Ligand Pharmaceuticals Incorporated, San Diego, CA (US)

(72) Inventors: Koc-Kan Ho, Salt Lake City, UT (US); David Diller, East Windsor, NJ (US); Jeffrey J. Letourneau, East Windsor, NJ (US); Brian F. McGuinness, Plainsboro, NJ (US); Andrew G. Cole, Robbinsville, NJ (US); David Rosen, Kendall Park, NJ (US); Cornelis A. van Oeveren, San Diego, CA (US); Jason C. Pickens, San Diego, CA (US); Lin Zhi, San Diego, CA (US); Yixing Shen, Encinitas, CA (US); Bijan Pedram, San Diego, CA (US)

(73) Assignee: LIGAND PHARMACEUTICALS INCORPORATED, San Diego, CA (US)

( * ) Notice: Subject to any disclaimer, the term of this patent is extended or adjusted under 35 U.S.C. 154(b) by 176 days.

(21) Appl. No.: 17/513,093

(22) Filed: Oct. 28, 2021

(65) Prior Publication Data

US 2022/0119413 A1 Apr. 21, 2022

Related U.S. Application Data

(63) Continuation of application No. 16/735,988, filed on Jan. 7, 2020, now Pat. No. 11,186,593, which is a continuation of application No. 16/015,925, filed on Jun. 22, 2018, now Pat. No. 10,604,533, which is a continuation of application No. 15/006,940, filed on Jan. 26, 2016, now Pat. No. 10,030,034, which is a continuation of application No. 14/137,318, filed on Dec. 20, 2013, now Pat. No. 9,266,874, which is a continuation of application No. 13/885,138, filed as application No. PCT/US2011/061532 on Nov. 18, 2011, now abandoned.

(60) Provisional application No. 61/415,685, filed on Nov. 19, 2010.

(51) Int. Cl.
| | | |
|---|---|---|
| C07D 235/02 | (2006.01) |
| C07D 269/02 | (2006.01) |
| C07D 277/42 | (2006.01) |
| C07D 277/60 | (2006.01) |
| C07D 513/04 | (2006.01) |
| A61K 31/407 | (2006.01) |
| A61K 31/4168 | (2006.01) |
| A61K 31/4353 | (2006.01) |
| A61P 29/00 | (2006.01) |
| A61P 37/00 | (2006.01) |
| C07D 417/12 | (2006.01) |
| C07D 417/14 | (2006.01) |
| C07D 471/04 | (2006.01) |

(52) U.S. Cl.
CPC .......... *C07D 513/04* (2013.01); *A61K 31/407* (2013.01); *A61K 31/4168* (2013.01); *A61K 31/4353* (2013.01); *A61P 29/00* (2018.01); *A61P 37/00* (2018.01); *C07D 235/02* (2013.01); *C07D 269/02* (2013.01); *C07D 277/42* (2013.01); *C07D 277/60* (2013.01); *C07D 417/12* (2013.01); *C07D 417/14* (2013.01); *C07D 471/04* (2013.01)

(58) Field of Classification Search
CPC .. C07D 235/02; C07D 269/02; C07D 277/42; C07D 277/60
See application file for complete search history.

(56) References Cited

U.S. PATENT DOCUMENTS

| | | |
|---|---|---|
| 8,022,222 B2 | 9/2011 | Aicher et al. |
| 2005/0153984 A1 | 7/2005 | Chen |
| 2007/0066577 A1 | 3/2007 | Choo et al. |
| 2010/0023218 A1 | 1/2010 | Hayakawa |

FOREIGN PATENT DOCUMENTS

| | | |
|---|---|---|
| EP | 1674466 | 6/2006 |
| EP | 2277881 A1 | 1/2011 |
| JP | S 48-78166 | 10/1973 |
| JP | 2000-086641 | 3/2000 |
| JP | 2006-520805 | 9/2006 |
| JP | 2007-518765 | 7/2007 |
| JP | 2008-255024 | 10/2008 |
| JP | 2009-523803 | 6/2009 |
| JP | 2009-524670 | 7/2009 |
| WO | WO 1997/049704 | 12/1997 |
| WO | WO 1997/49704 | 12/1997 |
| WO | WO 1999/24035 | 5/1999 |
| WO | WO 2003/082272 A1 | 10/2003 |
| WO | WO 2004/085425 A1 | 10/2004 |
| WO | WO 2005/037285 A1 | 4/2005 |
| WO | WO 2005/044793 | 5/2005 |

(Continued)

OTHER PUBLICATIONS

STN search record, Columbus, Ohio, US Registry [Online], published on Sep. 4, 2007.

(Continued)

*Primary Examiner* — Bruck Kifle
(74) *Attorney, Agent, or Firm* — Knobbe, Martens, Olson & Bear LLP

(57) ABSTRACT

Compounds and methods in the fields of chemistry and medicine are disclosed. Some of the disclosed embodiments include compounds, compositions and methods of using heterocycle amines. Some of the disclosed embodiments include heterocycle amines useful to treat inflammatory disorders.

11 Claims, No Drawings

(56) References Cited

FOREIGN PATENT DOCUMENTS

| WO | WO 2007/016392 | | 2/2007 |
|---|---|---|---|
| WO | WO 2007/058482 | | 5/2007 |
| WO | WO 2007/121154 | A2 | 10/2007 |
| WO | WO 2008/030579 | A2 | 3/2008 |
| WO | WO 2008/030584 | A2 | 3/2008 |
| WO | WO 2009/126635 | | 10/2009 |
| WO | WO 2009/128520 | A1 | 10/2009 |
| WO | WO 2010/011964 | | 1/2010 |
| WO | WO 2010/057121 | | 5/2010 |
| WO | WO 2010/106016 | A1 | 9/2010 |
| WO | WO 2010/135014 | | 11/2010 |
| WO | WO 2010/144909 | | 12/2010 |
| WO | WO 2011/110575 | | 6/2011 |
| WO | WO 2012/035055 | | 3/2012 |
| WO | WO 2015/150995 | | 10/2015 |

OTHER PUBLICATIONS

Buckley, G., et al., IRAK-4 inhibitors. Part III: A series of imidazo[1,2a]pyridines, Bioorganic & Medicinal Chemistry Letters 18:3656-3660 (2008).

Cruickshank, K, et al., Access to the 1,3, 4, 6-tetraazapentalene ring system, Tetrahedron Letters 26(23):2723-2726 (1985).

Caleta et al., "Novel Cyano-and Amidinobenzothiazole Derivatives: Synthesis, Antitumor Evaluation, and X-ray and Quantitative Structure—Activity Relationship (QSAR) Analysis", J. Med. Chem. 2009, 52, 1744-1756.

Das, J.; et al. Discovery of 2-amino-heteroaryl-benzothiazole-6-anilides as potent p56lck inhibitors., Bioorg Med Chem Lett. Aug. 4, 2003;13(15):2587-90.

Dasu M.R.D., et al., Increased Toll-Like Receptor (TLR) Activation and TLR Ligands in Recently Diagnosed Type 2 Diabetic Subjects, Diabetes Care 33(4): 861-868 (2010).

Deng, et al., IL-1 Receptor-associated kinase 1 regulates susceptibility to organ-specific autoimmunity, J Immunol 170:2833-2842 (2003).

Ehlers, et al., TLR9/MyD88 signaling is required for class switching to pathogenic IgG2a and 2b autoantibodies in SLE, JEM 203(3):553-561 (2006).

Greene, et al., Protective Groups in Organic Synthesis, 3rd Ed., John Wiley & Sons, New York, NY, 1999.

International Search Report dated May 16, 2012 received in International Application No. PCT/US2011/061532.

Kato, et al., Studies on Ketene and its Derivatives. LXI. Reaction of Primary Amine with Chloroketene Diethylacetal, Yakugaku Zasshi 94(5):627-632 (1974).

Lau, et al., RNA-associated autoantigens activate B cells by combined B cell antigen receptor/Toll-like receptor 7 engagement, JEM 202(9):1171-1177 (2005).

Li X., IRAK4 in TLR/IL-1R Signaling: Possible Clinical Applications, European J Immunol 38:614-618 (2008).

Pereira, et al., Dissymmetry of Certain Substituted Dipyridotetraazapentalenes, Tetrahedron 43(21):4931-4946 (1987).

Pubchem, Compound Summary for CID 118414016 (https://pubchem.ncbi.nlm.nih.gov/compound/118414016) Create date Feb. 23, 2016.

Ringwood, et al., The involvement of the interleukin-1 receptor-associated kinases (IRAKs) in cellular signaling networks controlling inflammation, Cytokine 42:1-7 (2008).

Safety and Efficacy of Pf-06650833 in Subjects with Rheumatoid Arthritis, with an Inadequate Response to Methotrexate, ClinicalTrials.gov Identifier: NCT02996500 (2018).

Sanmiguel J.C. et al., Interleukin-1 regulates keratinocyte expression of T cell targeting chemokines through interleukin-1 receptor associated kinase-1 (IRAK1) dependent and independent pathways, Cellular Signalling 21:685-694 (2009).

Song, K.W. et al., The kinase activities of interleukin-1 receptor associated kinase (IRAK)-1 and 4 are redundant in the control of inflammatory cytokine expression in human cells, Mol Immunol 46:1458-1466 (2009).

Staschke, et al., IRAK4 kinase activity is required for Th17 Differentiation and Th17-mediated disease, J Immunol 183:568-577 (2009).

Vaughan T. et al., Molecular mechanism underlying the inflammatory complication of leptin in macrophages, Mol Immunol, 47:2515-2518 (2010).

Wang Z. et al., Crystal Structures of IRAK-4 Kinase in Complex with Inhibitors: A Serine/Threonine Kinase with Tyrosine as a Gatekeeper, Structure 14:1835-1844 (2006).

Wang Z. et al., IRAK-4 Inhibitors for Inflammation, Curr Topics in Med Chem, 9:724-737 (2009).

Yin, J. et al., "Pd-Catalyzed N-Arylation of Heteroarylamines," Org. Lett. 4:3481-3484 (2002).

Zhang T. et al., A Modeling-Derived Hypothesis on Chronicity in Respiratory Dieseases: Desinsitized Pathogen Recognition Secondary to Hyperactive IRAK/TRAF6 Signaling, PLOS One 4(4):1-7 (2009).

Zhang T., et al., "Aminothiazolomorphinans with Mixed κ and μ Opioid Activity" J. Med Chem, 54:1903-1913 (2011).

Zhu J. et al., Toll-Like Receptor Signaling Pathways—Therapeutic Opportunities, Mediators of Inflammation vol. 2010, Article ID 781235, 7 pages (2010).

HETEROCYCLE AMINES AND USES THEREOF

RELATED APPLICATIONS

This application is a continuation of U.S. application Ser. No. 16/735,988 filed Jan. 7, 2020 which is a continuation of U.S. application Ser. No. 16/015,925 filed Jun. 22, 2018 now U.S. Pat. No. 10,604,533 issued Mar. 31, 2020 which is a continuation of U.S. application Ser. No. 15/006,940 filed Jan. 26, 2016 now U.S. Pat. No. 10,030,034 issued Jul. 24, 2018 which is a continuation of U.S. application Ser. No. 14/137,318 filed Dec. 20, 2013 now U.S. Pat. No. 9,266,874 which issued Feb. 23, 2016 which is a continuation of U.S. application Ser. No. 13/885,138 filed May 13, 2013 now abandoned which is the U.S. National Phase of App. No. PCT/US2011/061532 entitled "HETEROCYCLE AMINES AND USES THEREOF" filed Nov. 18, 2011 and published in English on May 24, 2012 as WO2012/068546 which claims the benefit of U.S. Prov. App. No. 61/415,685 filed Nov. 19, 2010 entitled "HETEROCYCLE AMINES AND USES THEREOF" which are each incorporated herein by reference in its entirety.

FIELD OF THE INVENTION

Compounds and methods in the fields of chemistry and medicine are disclosed. Some of the disclosed embodiments include compounds, compositions and methods of using heterocycle amines. Some of the disclosed embodiments include heterocycle amines useful to treat inflammatory disorders.

BACKGROUND

The recruitment of immune cells to sites of injury involves the concerted interactions of a large number of soluble mediators. Several cytokines appear to play roles in these processes, for example, IL-1 and TNF. Both cytokines are derived from mononuclear cells and macrophages along with other cell types. Physiologically, they produce many of the same proinflammatory responses, including fever, sleep, anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration seen in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, multiple sclerosis, diabetes, obesity, cancer, and sepsis.

The role of IL-1 in inflammation has been demonstrated by the ability of the highly specific IL-1 receptor antagonist protein (IL-1 Ra, or IRAP) to relieve inflammatory conditions. IL-1 treatment of cells induces the formation of a complex consisting of the two IL-1 receptor chains, IL-IRI and IL-1 RAcP, and the resulting heterodimer recruits an adaptor molecule designated as MyD88. MyD88 binds to a protein designated IRAK (Interleukin-1 Receptor-Associated Kinase). IRAK is subsequently phosphorylated and released from the receptor complex to interact with a tumor necrosis factor receptor-associated factor, TRAF6, which transduces the signal to downstream effector molecules. TRAF6 can trigger the NIK/IKK kinase cascade to activate the transcription factor NF-κB. NF-κB regulates a number of genes that, in turn, regulate immune and inflammatory responses.

Four IRAKs have been identified: IRAK-1, IRAK-2, the monomyeloic cell-specific IRAK-M, also known as IRAK-3, and IRAK-4. IRAK proteins have been shown to play a role in transducing signals other than those originating from IL-I receptors, including signals triggered by activation of IL-18 receptors and LPS receptors. Overexpression of IRAK-2 and IRAK-M has been shown to be capable of reconstituting the response to IL-1 and LPS in an IRAK deficient cell line.

SUMMARY OF THE INVENTION

Compounds, compositions and methods of using heterocycle amines are disclosed. Some of the disclosed embodiments include heterocycle amines useful to treat inflammatory disorders.

Some embodiments include a compound of Formula (I):

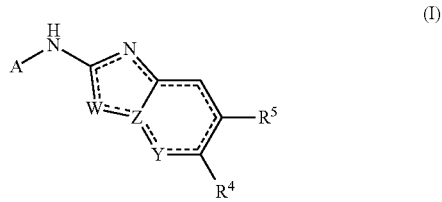

or a salt, ester, amide, or prodrug thereof,
wherein
=== is a single or double bond;
W is selected from CH, CH—CH, O, S, $NR^6$, and CO;
Y is N or $CR^9$;
Z is N or C, and Z is N if W is CH and Y is $CR^9$;
$R^4$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted carbocycle, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, $SO_2R^6$ and $SO_2NR^7R^8$;
$R^5$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;
or $R^4$ and $R^5$ are linked to form an optionally substituted non-aromatic ring;
each $R^6$ is independently selected from an optionally substituted aryl, an optionally substituted heteroaryl, and an optionally substituted non-aromatic ring, each optionally fused with a substituted aryl or a substituted heteroaryl, hydrogen, an optionally substituted $C_1$-$C_{10}$ alkyl, an optionally substituted $C_1$-$C_{10}$ haloalkyl, and an optionally substituted $C_1$-$C_{10}$ heteroalkyl;
each $R^7$ and $R^8$ is independently selected from an optionally substituted aryl, an optionally substituted heteroaryl, an optionally substituted non-aromatic ring, each optionally fused with a substituted aryl or a substituted heteroaryl, hydrogen, an optionally substituted $C_1$-$C_{10}$ alkyl, an optionally substituted $C_1$-$C_{10}$ haloalkyl, an optionally substituted $C_1$-$C_{10}$ alkenyl, an optionally substituted $C_1$-$C_{10}$ alkynyl, and an optionally substituted $C_1$-$C_{10}$ heteroalkyl, or $R^7$ and $R^8$ are linked to form an optionally substituted non-aromatic ring;

$R^9$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, and $SO_2NR^7R^8$;

A is an optionally substituted aryl or an optionally substituted heteroaryl group;

each optionally substituted group is either unsubstituted or substituted with one or more groups independently selected from alkyl, heteroalkyl, alkenyl, alkynyl, haloalkyl, heterohaloalkyl, aryl, arylalkyl, heteroaryl, non-aromatic ring, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, =O, =S, amino, and protected derivatives of amino groups.

In some embodiments, $R^4$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted carbocycle, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, $SO_2R^6$ and $SO_2NR^7R^8$.

In some embodiments, if $R^4$ is pyrazolyl, the pyrazolyl is not substituted with aryl or heteroaryl groups.

In some embodiments, if $R^4$ is oxazolyl, isoxazolyl, or imidazoyl, the oxazolyl, isoxazolyl, or imidazoyl radical is not substituted with aryl or heteroaryl groups.

Some embodiments include a compound represented by Formula (I-A):

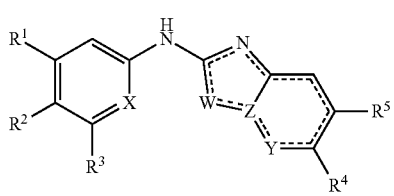

or a salt, ester, amide, or prodrug thereof,
wherein
X is N or $CR^{5'}$, wherein $R^{5'}$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;

$R^1$ is selected from hydrogen, halogen, $OR^6$, CN, $NR^7R^8$, $CH_2OR^6$, $CH_2NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, an optionally substituted $C_1$-$C_6$ heteroalkyl, $CO_2R^6$, $CONR^7R^8$, $SO_3R^6$, and $SO_2NR^7R^8$;

$R^2$ and $R^3$ are independently selected from hydrogen, halogen, $OR^6$, $NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, and an optionally substituted $C_1$-$C_6$ heteroalkyl.

Some embodiments include a compound represented by Formula (II):

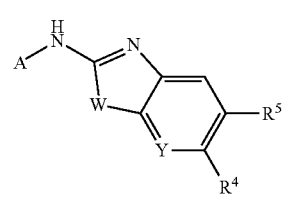

or a salt, ester, amide, or prodrug thereof.

Some embodiments include a compound represented by Formula (III):

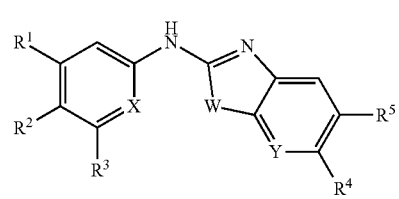

or a salt, ester, amide, or prodrug thereof,
wherein
X is N or $CR^{5'}$, wherein $R^{5'}$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;

$R^1$ is selected from hydrogen, halogen, $OR^6$, CN, $NR^7R^8$, $CH_2OR^6$, $CH_2NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, an optionally substituted $C_1$-$C_6$ heteroalkyl, $CO_2R^6$, $CONR^7R^8$, $SO_3R^6$, and $SO_2NR^7R^8$;

$R^2$ and $R^3$ are independently selected from hydrogen, halogen, $OR^6$, $NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, and an optionally substituted $C_1$-$C_6$ heteroalkyl.

In some embodiments, W is S.
In some embodiments, X is N.
In some embodiments, Y is $CR^9$.
In some embodiments, $R^4$ is selected from the group consisting of pyridyl, pyrazolyl, cyano, triazolyl, and oxazolyl.
In some embodiments, Y is N.
In some embodiments, $R^4$ is selected from the group consisting of pyridyl, pyrazolyl, pyrimidinyl, pyridazinyl, and $C_1$-$C_6$ alkyl.

Some embodiments include a compound represented by Formula (IV):

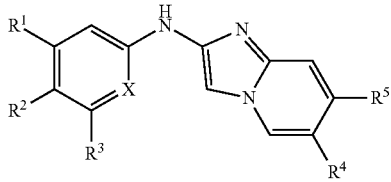

or a salt, ester, amide, or prodrug thereof,
wherein:

X is N or $CR^{5'}$, wherein $R^{5'}$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;

$R^1$ is selected from hydrogen, halogen, $OR^6$, CN, $NR^7R^8$, $CH_2OR^6$, $CH_2NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, an optionally substituted $C_1$-$C_6$ heteroalkyl, $CO_2R^6$, $CONR^7R^8$, $SO_3R^6$, and $SO_2NR^7R^8$; and $R^2$ and $R^3$ are independently selected from hydrogen, halogen, $OR^6$, $NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, and an optionally substituted $C_1$-$C_6$ heteroalkyl.

In some embodiments, X is N.

Some embodiments include a pharmaceutical composition comprising a compound provided herein and a pharmaceutically acceptable carrier.

Some embodiments include a method of treating a disorder responsive to inhibition of Interleukin-1 Receptor-Associated Kinase-mediated signal transduction comprising administering to a subject in need thereof an effective amount of a compound provided herein.

In some embodiments, the disorder is an inflammatory disorder. In some embodiments, the inflammatory disorder is selected from the group consisting of osteoarthritis, rheumatoid arthritis, multiple sclerosis, corneal ulcers, uveitis, and inflammatory bowel disease.

In some embodiments, the disorder is a skin disorder. In some embodiments, the skin disorder is selected from the group consisting of dermatitis, cutaneous eosinophilias, Lichen planus, urticaria, psoriasis, pruritus, angioedemas, chronic skin ulcers, conjunctivitis, vasculitides, and erythemas.

In some embodiments, the disorder is a respiratory disorder. In some embodiments, the respiratory disorder is selected from the group consisting of asthma, rhinitis, chronic obstructive pulmonary disease, bronchitis, nasal polyposis, nasal congestion, farmer's lung, fibroid lung and cough.

In some embodiments, the disorder is selected from the group consisting of diabetes, obesity, allergic disease, cancer, and sepsis.

Some embodiments include use of a compound provided herein in the preparation of a medicament for treating a disorder responsive to inhibition of Interleukin-1 Receptor-Associated Kinase-mediated signal transduction.

In some embodiments, the disorder is an inflammatory disorder. In some embodiments, the inflammatory disorder is selected from the group consisting of osteoarthritis, rheumatoid arthritis, multiple sclerosis, corneal ulcers, uveitis, and inflammatory bowel disease.

In some embodiments, the disorder is a skin disorder. In some embodiments, the skin disorder is selected from the group consisting of dermatitis, cutaneous eosinophilias, Lichen planus, urticaria, psoriasis, pruritus, angioedemas, chronic skin ulcers, conjunctivitis, vasculitides, and erythemas.

In some embodiments, the disorder is a respiratory disorder. In some embodiments, the respiratory disorder is selected from the group consisting of asthma, rhinitis, chronic obstructive pulmonary disease, bronchitis, nasal polyposis, nasal congestion, farmer's lung, fibroid lung and cough.

In some embodiments, the disorder is selected from the group consisting of diabetes, obesity, allergic disease, cancer, and sepsis.

Some embodiments include a compound provided herein for treating a disorder responsive to inhibition of Interleukin-1 Receptor-Associated Kinase-mediated signal transduction.

In some embodiments, the disorder is an inflammatory disorder. In some embodiments, the inflammatory disorder is selected from the group consisting of osteoarthritis, rheumatoid arthritis, multiple sclerosis, corneal ulcers, uveitis, and inflammatory bowel disease.

In some embodiments, the disorder is a skin disorder. In some embodiments, the skin disorder is selected from the group consisting of dermatitis, cutaneous eosinophilias, Lichen planus, urticaria, psoriasis, pruritus, angioedemas, chronic skin ulcers, conjunctivitis, vasculitides, and erythemas.

In some embodiments, the disorder is a respiratory disorder. In some embodiments, the respiratory disorder is selected from the group consisting of asthma, rhinitis, chronic obstructive pulmonary disease, bronchitis, nasal polyposis, nasal congestion, farmer's lung, fibroid lung and cough.

In some embodiments, the disorder is selected from the group consisting of diabetes, obesity, allergic disease, cancer, and sepsis.

DETAILED DESCRIPTION

Compounds and methods in the fields of chemistry and medicine are disclosed. Some of the disclosed embodiments include compounds, compositions and methods of using heterocycle amines. Some of the disclosed embodiments include heterocycle amines useful to treat inflammatory disorders.

Some embodiments include a compound of Formula (I):

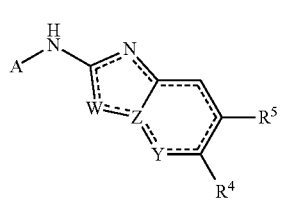

or a salt, ester, amide, or prodrug thereof,
wherein
=== is a single or double bond;
W is selected from CH, CH—CH, O, S, $NR^6$, and CO;

Y is N or CR⁹; p Z is N or C, and Z is N if W is CH and Y is CR⁹;

R⁴ is selected from hydrogen, halogen, OR⁶, CN, NR⁷R⁸, CH₂OR⁶, an optionally substituted aryl, an optionally substituted heteroaryl, an optionally substituted non-aromatic ring, an optionally substituted carbocycle, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, CO₂R⁶, SO₃R⁶, SO₂R⁶ and SO₂NR⁷R⁸;

R⁵ is selected from hydrogen, halogen, OR⁶, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;

or R⁴ and R⁵ are linked to form an optionally substituted non-aromatic ring;

each R⁶ is independently selected from an optionally substituted aryl, an optionally substituted heteroaryl, and an optionally substituted non-aromatic ring, each optionally fused with a substituted aryl or a substituted heteroaryl, hydrogen, an optionally substituted $C_1$-$C_{10}$ alkyl, an optionally substituted $C_1$-$C_{10}$ haloalkyl, and an optionally substituted $C_1$-$C_{10}$ heteroalkyl;

each R⁷ and R⁸ is independently selected from an optionally substituted aryl, an optionally substituted heteroaryl, an optionally substituted non-aromatic ring, each optionally fused with a substituted aryl or a substituted heteroaryl, hydrogen, an optionally substituted $C_1$-$C_{10}$ alkyl, an optionally substituted $C_1$-$C_{10}$ haloalkyl, an optionally substituted $C_1$-$C_{10}$ alkenyl, an optionally substituted $C_1$-$C_{10}$ alkynyl, and an optionally substituted $C_1$-$C_{10}$ heteroalkyl, or R⁷ and R⁸ are linked to form an optionally substituted non-aromatic ring;

R⁹ is selected from hydrogen, halogen, OR⁶, CN, NR⁷R⁸, CH₂OR⁶, an optionally substituted aryl, an optionally substituted heteroaryl, an optionally substituted non-aromatic ring, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, CO₂R⁶, SO₃R⁶, and SO₂NR⁷R⁸;

A is an optionally substituted aryl or an optionally substituted heteroaryl group;

each optionally substituted group is either unsubstituted or substituted with one or more groups independently selected from alkyl, heteroalkyl, alkenyl, alkynyl, haloalkyl, heterohaloalkyl, aryl, arylalkyl, heteroaryl, non-aromatic ring, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, =O, =S, amino, and protected derivatives of amino groups.

In some embodiments, R⁴ is selected from hydrogen, halogen, OR⁶, CN, NR⁷R⁸, CH₂OR⁶, an optionally substituted aryl, an optionally substituted heteroaryl, an optionally substituted non-aromatic ring, an optionally substituted carbocycle, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, CO₂R⁶, SO₃R⁶, SO₂R⁶ and SO₂NR⁷R⁸.

In some embodiments, if R⁴ is pyrazolyl, the pyrazolyl is not substituted with aryl or heteroaryl groups.

In some embodiments, if R⁴ is oxazolyl, isoxazolyl, or imidazoyl, the oxazolyl, isoxazolyl, or imidazoyl radical is not substituted with aryl or heteroaryl groups.

Some embodiments include a compound represented by Formula (I-A):

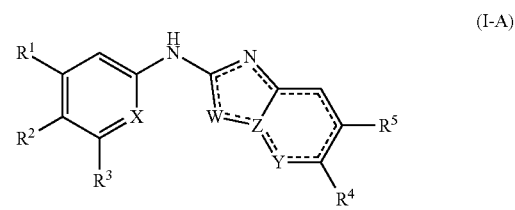

(I-A)

or a salt, ester, amide, or prodrug thereof, wherein

X is N or CR⁵', wherein R⁵' is selected from hydrogen, halogen, OR⁶, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;

R¹ is selected from hydrogen, halogen, OR⁶, CN, NR⁷R⁸, CH₂OR⁶, CH₂NR⁷R⁸, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, an optionally substituted $C_1$-$C_6$ heteroalkyl, CO₂R⁶, CONR⁷R⁸, SO₃R⁶, and SO₂NR⁷R⁸;

R² and R³ are independently selected from hydrogen, halogen, OR⁶, NR⁷R⁸, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, and an optionally substituted $C_1$-$C_6$ heteroalkyl.

Some embodiments include a compound represented by Formula (II):

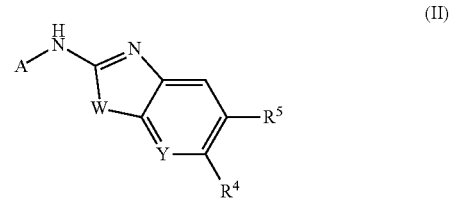

(II)

or a salt, ester, amide, or prodrug thereof.

Some embodiments include a compound represented by Formula (III):

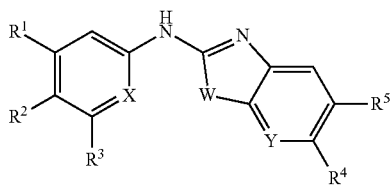

or a salt, ester, amide, or prodrug thereof,
wherein
X is N or $CR^{5'}$, wherein $R^{5'}$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;
$R^1$ is selected from hydrogen, halogen, $OR^6$, CN, $NR^7R^8$, $CH_2OR^6$, $CH_2NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, an optionally substituted $C_1$-$C_6$ heteroalkyl, $CO_2R^6$, $CONR^7R^8$, $SO_3R^6$, and $SO_2NR^7R^8$;
$R^2$ and $R^3$ are independently selected from hydrogen, halogen, $OR^6$, $NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, and an optionally substituted $C_1$-$C_6$ heteroalkyl.

In some embodiments, W is S.
In some embodiments, X is N.
In some embodiments, Y is $CR^9$.
In some embodiments, $R^4$ is selected from the group consisting of pyridyl, pyrazolyl, cyano, triazolyl, and oxazolyl.
In some embodiments, Y is N.
In some embodiments, $R^4$ is selected from the group consisting of pyridyl, pyrazolyl, pyrimidinyl, pyridazinyl, and $C_1$-$C_6$ alkyl.

Some embodiments include a compound represented by Formula (IV):

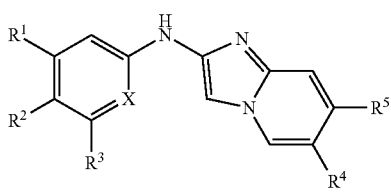

or a salt, ester, amide, or prodrug thereof,
wherein:
X is N or $CR^{5'}$, wherein $R^{5'}$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;
$R^1$ is selected from hydrogen, halogen, $OR^6$, CN, $NR^7R^8$, $CH_2OR^6$, $CH_2NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, an optionally substituted $C_1$-$C_6$ heteroalkyl, $CO_2R^6$, $CONR^7R^8$, $SO_3R^6$, and $SO_2NR^7R^8$; and
$R^2$ and $R^3$ are independently selected from hydrogen, halogen, $OR^6$, $NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, and an optionally substituted $C_1$-$C_6$ heteroalkyl.

In some embodiments, X is N.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989)), which is incorporated herein by reference in its entirety for any purpose.

The term "alkyl" refers to a branched or unbranched aliphatic hydrocarbon group. An alkyl may be a "saturated alkyl," which means that it does not contain any alkene or alkyne groups. An alkyl group may be an "unsaturated alkyl," which means that it comprises at least one alkene or alkyne group. An alkyl, whether saturated or unsaturated, may be branched or straight chain. Alkyls may be cyclic or non-cyclic. Cyclic alkyls may include multicyclic systems including fused alkyl rings. Alkyls may be substituted or unsubstituted. Alkyls include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated).

The term "lower alkyl" refers to an alkyl comprising 1 to 5 carbon atoms. The term "medium alkyl" refers to an alkyl comprising 5 to 10 carbon atoms. An alkyl may be designated as "$C_1$-$C_4$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, n-butyl, iso-butyl, sec-butyl, and t-butyl.

The term "alkenyl" refers to an alkyl group comprising at least one carbon-carbon double bond, including by way of non-limiting example ethenyl, propenyl, and butenyl.

The term "alkynyl" refers to an alkyl group comprising at least one carbon-carbon triple bond, including by way of non-limiting example ethynyl, propynyl, and butynyl.

The term "haloalkyl" refers to an alkyl in which at least one hydrogen atom is replaced with a halogen atom. In certain of the embodiments in which two or more hydrogen atoms are replaced with halogen atoms, the halogen atoms are all the same as one another. In certain of such embodiments, the halogen atoms are not all the same as one another.

The term "heteroalkyl" refers to a branched or unbranched aliphatic hydrocarbon group comprising one or more oxygen, sulfur, nitrogen, or NH. Examples of heteroalkyls include, but are not limited to, $CH_3C(=O)CH_2—$, $CH_3C(=O)CH_2CH_2—$, $CH_3CH_2C(=O)CH_2CH_2—$, $CH_3C(=O)CH_2CH_2CH_2—$, $CH_3NHC(=O)CH_2—$, $CH_3C(=O)NHCH_2—$, $CH_3OCH_2CH_2—$, $CH_3NHCH_2—$, and the like.

The term "straight-chain alkoxy" refers to a group comprising the formula: $—(CH_2)_pO—$ wherein p is any integer. Straight-chain alkoxy does not include substituted or branched alkoxy groups.

The term "non-straight-chain-alkoxy-heteroalkyl" refers to any heteroalkyl that is not a straight-chain alkoxy heteroalkyl. Thus, for example, non-straight-chain-alkoxy heteroalkyls include, but are not limited to: 2,2-isopropyloxy; 1,2-propyloxy; 1,1-ethyloxy; methylamino; ethylamino; propylamino; methylpyrrolidino; and methylpiperidino.

The term "heterohaloalkyl" refers to a heteroalkyl in which at least one hydrogen atom is replaced with a halogen atom.

The term "carbocycle" refers to a group comprising a covalently closed ring, wherein each of the atoms that forms and/or comprises the ring is a carbon atom. Carbocyclic rings may be formed by three, four, five, six, seven, eight, nine, or more than nine carbon atoms. Carbocycles may be optionally substituted.

The term "heterocycle" refers to a group comprising a covalently closed ring wherein at least one atom that forms and/or comprises the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same or different from one another. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

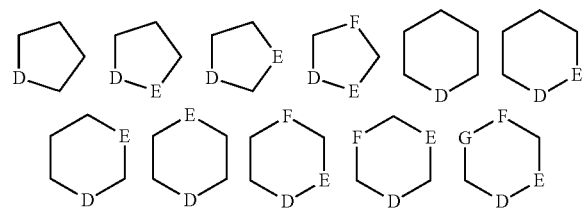

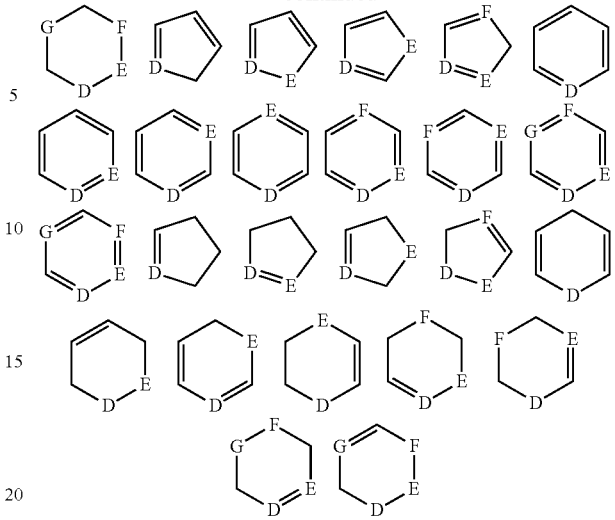

wherein D, E, F, and G independently represent a heteroatom. Each of D, E, F, and G may be the same or different from one another.

The term "heteroatom" refers to an atom other than carbon or hydrogen. Heteroatoms, typically, are independently selected from oxygen, sulfur, nitrogen, and phosphorus, but heteroatoms are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic ring, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl) phenyl.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_3$-8 heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine, pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that does not have a delocalized π-electron system in its principle and/or predominant tautomer.

The term "cycloalkyl" refers to a group comprising a non-aromatic ring wherein each of the atoms forming the ring is a carbon atom. Cycloalkyl rings may be formed by three, four, five, six, seven, eight, nine, or more than nine carbon atoms. Cycloalkyls may include multicyclic systems (e.g., fused ring systems). Cycloalkyls may be optionally substituted. In certain embodiments, a cycloalkyl comprises one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

The term "non-aromatic ring" refers to a group comprising a non-aromatic ring moiety wherein the atoms that form and/or comprise the ring include carbon and/or heteroatoms. When heteroatoms are included in the ring, one or more such heteroatoms may be present. Non-aromatic rings also optionally include one or more carbonyl or thiocarbonyl groups as part of the ring. Non-aromatic rings may be formed by three, four, five, six, seven, eight, nine, or more than nine atoms. Non-aromatic rings may be optionally substituted. Examples of non-aromatic rings include, but are not limited to, cycloalkyls (including but not limited to cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene), lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "ring" refers to any covalently closed structure. Rings include, for example, carbocycles (e.g., aryls and cycloalkyls), heterocycles (e.g., heteroaryls and non-aromatic heterocyclic rings), aromatics (e.g., aryls and heteroaryls), and non-aromatic rings. Rings may be optionally substituted. Rings may form part of a ring system.

The term "ring system" refers to a either a single ring or two or more rings, wherein, if two or more rings are present, the two or more of the rings are fused. The term "fused" refers to structures in which two or more rings share one or more bonds.

The substituent "R" appearing by itself and without a number designation refers to a substituent selected from alkyl, cycloalkyl, aryl, heteroaryl (bonded through a ring carbon) and non-aromatic ring (bonded through a ring carbon).

The term "O-carboxy" refers to the group consisting of formula RC(=O)O—.

The term "C-carboxy" refers to the group consisting of formula —C(=O)OR.

The term "acetyl" refers to the group consisting of formula —C(=O)CH_3.

The term "trihalomethanesulfonyl" refers to the group consisting of formula $X_3CS(=O)_2$— where X is a halogen.

The term "cyano" refers to the group consisting of formula —CN.

The term "isocyanato" refers to the group consisting of formula —NCO.

The term "thiocyanato" refers to the group consisting of formula —CNS.

The term "isothiocyanato" refers to the group consisting of formula —NCS.

The term "sulfonyl" refers to the group consisting of formula —S(=O) 13 R.

The term "S-sulfonamido" refers to the group consisting of formula —S(=O)_2NR.

The term "N-sulfonamido" refers to the group consisting of formula RS(=O)_2NH—.

The term "trihalomethanesulfonamido" refers to the group consisting of formula $X_3CS(=O)_2NR$—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR_2.

The term "N-amido" refers to the group consisting of formula RC(=O)NH—.

The term "oxo" refers to the group consisting of formula =O.

The term "carbonyl" refers to the group consisting of formula —C(=O)R.

The term "thiocarbonyl" refers to the group consisting of formula —C(=S)R.

The term "dihydropyrazolylene" refers to a di-radical of an optionally substituted dihydropyrazole ring, wherein the dihydropyrazole ring has the structure:

and wherein the two radicals may be at any positions on the ring.

The term "pyrazolyl" refers to a radical of a pyrazole ring, wherein the pyrazole ring has the structure:

and wherein the radical may be at any position on the ring.

The term "ester" refers to a chemical moiety with formula —(R)$_n$—COOR', where R and R' are independently selected from alkyl, cycloalkyl, aryl, heteroaryl (bonded through a ring carbon) and non-aromatic ring (bonded through a ring carbon), where n is 0 or 1.

The term "amide" refers to a chemical moiety with formula —(R)$_n$—C(O)NHR' or —(R)$_n$—NHC(O)R', where R and R' are independently selected from alkyl, cycloalkyl, aryl, heteroaryl (bonded through a ring carbon) and heteroalicyclic (bonded through a ring carbon), where n is 0 or 1. In certain embodiments, an amide may be an amino acid or form part of a peptide.

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein in its entirety.

Unless otherwise indicated, the term "optionally substituted" refers to a group in which none, one, or more than one of the hydrogen atoms has been replaced with one or more group(s) individually and independently selected from: alkyl, heteroalkyl, haloalkyl, alkenyl, alkynyl, heterohaloalkyl, cycloalkyl, aryl, arylalkyl, heteroaryl, non-aromatic ring, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, oxo, and amino, including mono- and di-substituted amino groups, and the protected derivatives of amino groups. Such protective derivatives (and protecting groups that may form such protective derivatives) are known to those of skill in the art and may be found in references such as Greene and Wuts, above. In embodiments in which two or more hydrogen atoms have been substituted, the substituent groups may together form a ring.

Throughout the specification, groups and substituents thereof can be chosen by one skilled in the field to provide stable moieties and compounds.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "prodrug" refers to a pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

Certain Compounds

In certain embodiments, compounds of Formula (I) are provided:

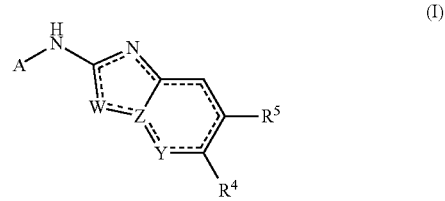

or a salt, ester, amide, or prodrug thereof,
wherein
=== is a single or double bond;
W is selected from CH, CH—CH, O, S, NR$^6$, and CO;
Y is N or CR$^9$;
Z is N or C, and Z is N if W is CH and Y is CR$^9$;

$R^4$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted carbocycle, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, $SO_2R^6$ and $SO_2NR^7R^8$;

$R^5$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;

or $R^4$ and $R^5$ are linked to form an optionally substituted non-aromatic ring;

each $R^6$ is independently selected from an optionally substituted aryl, an optionally substituted heteroaryl, and an optionally substituted non-aromatic ring, each optionally fused with a substituted aryl or a substituted heteroaryl, hydrogen, an optionally substituted $C_1$-$C_{10}$ alkyl, an optionally substituted $C_1$-$C_{10}$ haloalkyl, and an optionally substituted $C_1$-$C_{10}$ heteroalkyl;

each $R^7$ and $R^8$ is independently selected from an optionally substituted aryl, an optionally substituted heteroaryl, an optionally substituted non-aromatic ring, each optionally fused with a substituted aryl or a substituted heteroaryl, hydrogen, an optionally substituted $C_1$-$C_{10}$ alkyl, an optionally substituted $C_1$-$C_{10}$ haloalkyl, an optionally substituted $C_1$-$C_{10}$ alkenyl, an optionally substituted $C_1$-$C_{10}$ alkynyl, and an optionally substituted $C_1$-$C_{10}$ heteroalkyl, or $R^7$ and $R^8$ are linked to form an optionally substituted non-aromatic ring;

$R^9$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, and $SO_2NR^7R^8$;

A is an optionally substituted aryl or an optionally substituted heteroaryl group;

each optionally substituted group is either unsubstituted or substituted with one or more groups independently selected from alkyl, heteroalkyl, alkenyl, alkynyl, haloalkyl, heterohaloalkyl, aryl, arylalkyl, heteroaryl, non-aromatic ring, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, =O, =S, amino, and protected derivatives of amino groups.

In some embodiments, $R^4$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted carbocycle, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, $SO_2R^6$ and $SO_2NR^7R^8$.

In some embodiments, if $R^4$ is pyrazolyl, the pyrazolyl is not substituted with aryl or heteroaryl groups.

In some embodiments, if $R^4$ is oxazolyl, isoxazolyl, or imidazoyl, the oxazolyl, isoxazolyl, or imidazoyl radical is not substituted with aryl or heteroaryl groups.

Some embodiments include a compound represented by Formula (I-A):

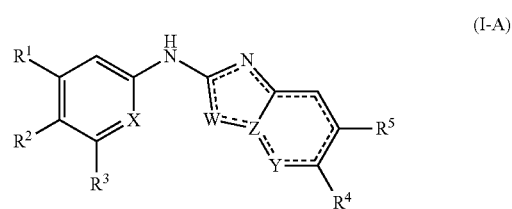

or a salt, ester, amide, or prodrug thereof, wherein

X is N or $CR^{5'}$, wherein $R^{5'}$ is selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;

$R^1$ is selected from hydrogen, halogen, $OR^6$, CN, $NR^7R^8$, $CH_2OR^6$, $CH_2NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, an optionally substituted $C_1$-$C_6$ heteroalkyl, $CO_2R^6$, $CONR^7R^8$, $SO_3R^6$, and $SO_2NR^7R^8$;

$R^2$ and $R^3$ are independently selected from hydrogen, halogen, $OR^6$, $NR^7R^8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, and an optionally substituted $C_1$-$C_6$ heteroalkyl.

Some embodiments include a compound represented by Formula (II), (III), or (IV):

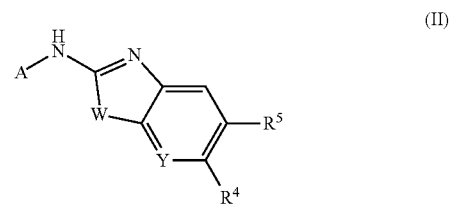

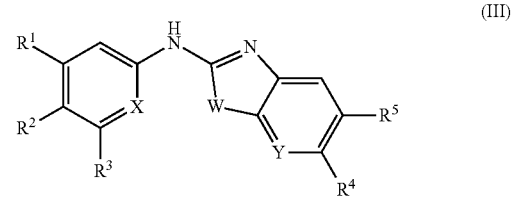

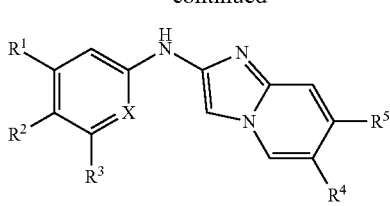

or a salt, ester, amide, or prodrug thereof,
wherein:
W is selected from O, S, $NR^6$, and CO;
X is N or $CR^5$;
Y is N or $CR^9$;
$R^4$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted carbocycle, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, and $SO_2NR^7R^8$;
each $R^5$ is independently selected from hydrogen, halogen, $OR^6$, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ haloheteroalkyl, an optionally substituted $C_1$-$C_6$ alkenyl, and an optionally substituted $C_1$-$C_6$ alkynyl;
or $R^4$ and $R^5$ are linked to form an optionally substituted non-aromatic ring;
each $R^6$ is independently selected from hydrogen, an optionally substituted aryl, an optionally substituted heteroaryl, an optionally substituted non-aromatic ring, an optionally substituted $C_1$-$C_{10}$ alkyl, an optionally substituted $C_1$-$C_{10}$ haloalkyl, and an optionally substituted $C_1$-$C_{10}$ heteroalkyl, each optionally fused with a substituted aryl or a substituted heteroaryl;
each $R^7$ and $R^8$ is independently selected from hydrogen, an optionally substituted aryl, an optionally substituted heteroaryl, an optionally substituted non-aromatic ring, an optionally substituted $C_1$-$C_{10}$ alkyl, an optionally substituted $C_1$-$C_{10}$ haloalkyl, an optionally substituted $C_1$-$C_{10}$ alkenyl, an optionally substituted $C_1$-$C_{10}$ alkynyl, and an optionally substituted $C_1$-$C_{10}$ heteroalkyl, each optionally fused with a substituted aryl or a substituted heteroaryl, or $R^7$ and $R^8$ are linked to form an optionally substituted non-aromatic ring;
$R^9$ is selected from hydrogen, halogen, $OR^6$, CN, $NR^7R^8$, $CH_2OR^6$, an optionally substituted aryl, an optionally substituted heteroaryl, an optionally substituted non-aromatic ring, an optionally substituted $C_1$-$C_6$ alkyl, an optionally substituted $C_1$-$C_6$ haloalkyl, an optionally substituted $C_1$-$C_6$ heteroalkyl, an optionally substituted $C_1$-$C_6$ alkenyl, an optionally substituted $C_1$-$C_6$ alkynyl, $CO_2R^6$, $SO_3R^6$, and $SO_2NR^7R^8$;
A is an optionally substituted aryl or an optionally substituted heteroaryl group;
each optionally substituted group is either unsubstituted or substituted with one or more groups independently selected from alkyl, heteroalkyl, alkenyl, alkynyl, haloalkyl, heterohaloalkyl, aryl, arylalkyl, heteroaryl, non-aromatic ring, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, =O, =S, amino, and protected derivatives of amino groups.

In some embodiments, if $R^4$ is a pyrazolyl, oxazolyl, isoxazolyl, or imidazoyl radical in compounds of Formula (II), (III), or (IV), the pyrazolyl, oxazolyl, isoxazolyl, or imidazoyl radical is not substituted with aryl or heteroaryl groups.

In some specific embodiments, if $R^4$ is a pyrazolyl radical in compounds of Formula (II), (III), or (IV), the pyrazolyl is not substituted with aryl or heteroaryl groups.

Certain Synthetic Methods

In certain embodiments, compounds of the present invention can by synthesized using the following Schemes.

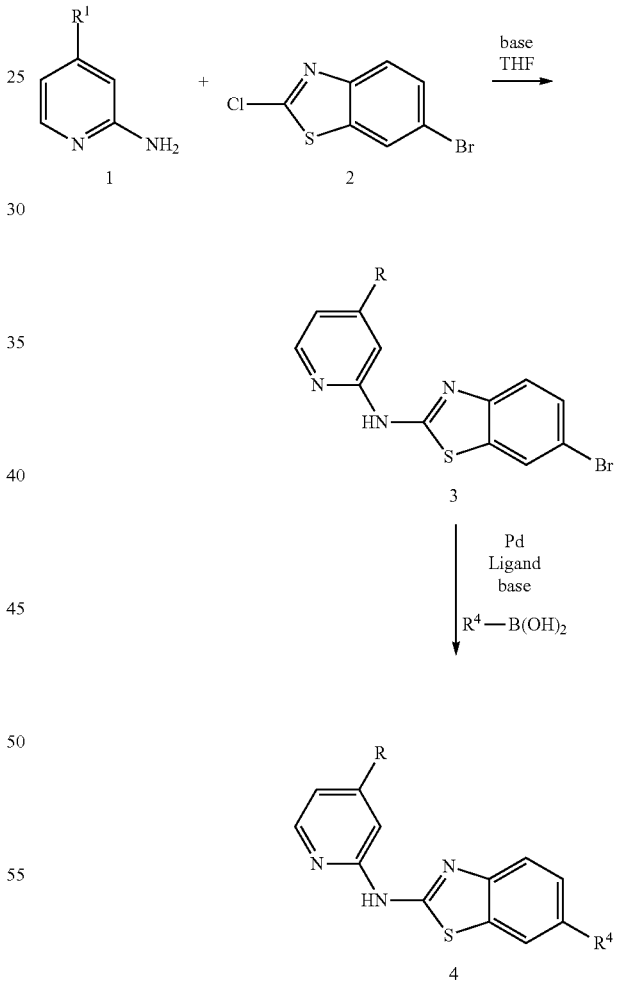

Scheme I describes the synthesis of aminopyridine substituted benzothiazoles. An aminopyridine 1 is treated with a base such as NaH and reacted with 6-bromo-2-chlorobenzothiazole 2 to afford compounds of structure 3. Palladium catalyzed coupling of structure 3 with a boronic acid affords compounds of structure 4.

Scheme II

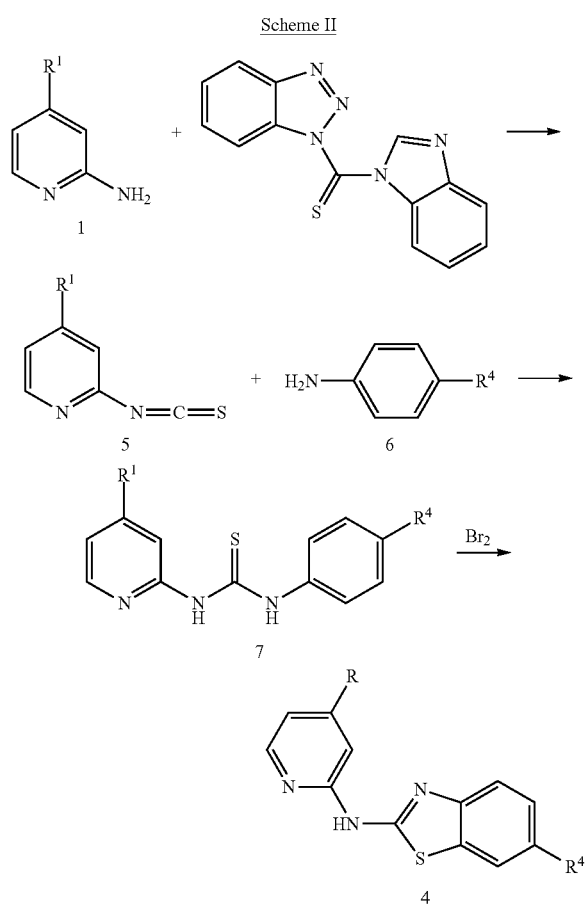

Scheme II describes the synthesis of aminopyridine substituted benzothiazoles. Aminopyridine 1 is converted to an isothiocyanate 5 and reacted with an aniline 6, to give a thiourea 7. The thiourea is oxidatively cyclized with, for example, bromine to give the benzothiazole 4.

Scheme III

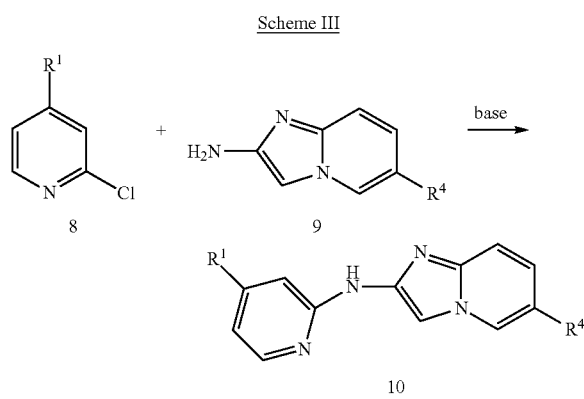

Scheme III describes the synthesis of aminopyridine substituted imidazopyridines 10. A 2-halopyridine, such as compound 8, is coupled with an aminoimidazopyridine, such as 9, under the influence of a palladium catalyst and a base to furnish products 10.

One of skill in the art will recognize that analogous synthetic schemes may be used to synthesize similar compounds. One of skill will recognize that compounds of the present invention may be synthesized using other synthesis schemes. In certain embodiments, the invention provides a salt corresponding to any of the compounds provided herein.

Certain Pharmaceutical Agents

Some embodiments include pharmaceutical agents. In some embodiments a pharmaceutical agent can include a compound and/or composition provided herein and a pharmaceutical carrier. In certain embodiments, at least one compound of Formula (I), (II), (III), or (IV), or a pharmaceutically acceptable salt, ester, amide, and/or prodrug thereof, either alone or combined with one or more pharmaceutically acceptable carriers, forms a pharmaceutical agent. Techniques for formulation and administration of compounds of the present embodiments may be found for example, in "Remington's Pharmaceutical Sciences," Mack Publishing Co., Easton, PA, 18th edition, 1990, which is incorporated herein by reference in its entirety.

In certain embodiments, a pharmaceutical agent comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present embodiments is a liquid (e.g., a suspension, elixir and/or solution). In certain of such embodiments, a liquid pharmaceutical agent comprising one or more compounds of the present embodiments is prepared using ingredients known in the art, including, but not limited to, water, glycols, oils, alcohols, flavoring agents, preservatives, and coloring agents.

In certain embodiments, a pharmaceutical agent comprising one or more compounds of the present embodiments is a solid (e.g., a powder, tablet, and/or capsule). In certain of such embodiments, a solid pharmaceutical agent comprising one or more compounds of the present embodiments is prepared using ingredients known in the art, including, but not limited to, starches, sugars, diluents, granulating agents, lubricants, binders, and disintegrating agents.

In certain embodiments, a pharmaceutical agent comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present embodiments comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present embodiments comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present embodiments comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present embodiments comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

Certain compounds used in pharmaceutical agent of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present embodiments is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical agent comprising one or more compounds of the present embodiments is useful for treating a condition or disorder in a mammal, such as a human. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present embodiments is administered in the form of a dosage unit (e.g., tablet, capsule, bolus, etc.). In certain embodiments, such dosage units comprise a compound or composition provided herein, such as a compound or composition comprising Formula (I), (II), (III), or (IV), in a dose from about 1 µg/kg of body weight to about 50 mg/kg of body weight, and from about 2 µg/kg of body weight to about 25 mg/kg of body weight, from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present embodiments is prepared for oral administration. In certain of such embodiments, a pharmaceutical agent is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g., in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the present embodiments and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, New Jersey), hydrophilic ointment (USP) and Lubriderm™, available from Pfizer (Morris Plains, New Jersey).

In certain embodiments, the formulation, route of administration and dosage for a pharmaceutical agent of the present embodiments can be chosen in view of a particular patient's condition. In certain embodiments, a pharmaceutical agent is administered as a single dose. In certain embodiments, a pharmaceutical agent is administered as a series of two or more doses administered over one or more days.

In certain embodiments, a pharmaceutical agent of the present embodiments is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present embodiments. In certain embodiments, a daily dosage regimen is administered as a single daily dose. In certain embodiments, a daily dosage regimen is administered as two, three, four, or more than four doses.

In certain embodiments, a pharmaceutical agent of the present embodiments is administered by continuous intravenous infusion. In certain of such embodiments, from 0.1 mg to 500 mg of a composition of the present embodiments is administered per day.

In certain embodiments, a pharmaceutical agent of the present embodiments is administered for a period of continuous therapy. For example, a pharmaceutical agent of the present embodiments may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration of compound in a patient. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC). In certain embodiments, pharmaceutical agents of the present embodiments are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present embodiments.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Certain Therapeutic Methods

Some compounds and compositions provided herein, such as compounds and/or compositions comprising Formula (I), (II), (III), and (IV) are useful for the treatment of a variety of diseases and disorders. Examples of diseases and disorders include inflammatory disorders, cell proliferative disorders, and immune-related disorders, and disorders associated with IRAK-mediated signal transduction.

Inflammation of tissues and organs occurs in a wide range of disorders and diseases and in certain variations results from activation of the cytokine family of receptors. Example inflammatory disorders associated with activation of IRAK kinases and/or disorders IRAK-mediated signal transduction include skin disorders, respiratory disorders, and other disorders with an allergic component. These disorders are treated or prevented by modulation of IRAK activity, for example, by administration of certain compounds and/or compositions provided herein. In some embodiments, methods of treating a subject in need thereof include administering an effective amount of a compound or composition provided herein. Some embodiments include treating a disorder responsive to inhibition of IRAK-mediated signal transduction.

Example skin disorders include dermatitis, cutaneous eosinophilias, Lichen planus, urticaria, psoriasis, pruritus, angioedemas, chronic skin ulcers, conjunctivitis, vasculitides, or erythemas. Examples of respiratory disorders include asthma, rhinitis, chronic obstructive pulmonary disease, bronchitis, nasal polyposis, nasal congestion, farmer's lung, fibroid lung and cough. Other example diseases that may be treated with the compounds and compositions provided herein include osteoarthritis, rheumatoid arthritis, multiple sclerosis, corneal ulcers, uveitis, pain and inflammatory bowel disease. More example disorders include diabetes, obesity, allergic disease, cancer, and sepsis.

In some embodiments, the compounds and compositions provided herein can be administered in combination with an additional active agent. Examples of other active agents include anti-inflammatory agents, analgesic agents, such as: opiate agonists; lipoxygenase inhibitors; cyclooxygenase inhibitors, such as cyclooxygenase-2 inhibitors; interleukin inhibitors, such as interleukin-1 receptor antagonist; NMDA antagonists; inhibitors of nitric oxide or inhibitors of the synthesis of nitric oxide; a non-steroidal anti-inflammatory agent; or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sulindac, tenidap, and the like. In some embodiments, the instant compounds and/or compoistions may be administered with: a potentiator such as caffeine, an H2-antagonist (e.g., ranitidine), simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextromethorphan; a diuretic; and a sedating or non-sedating antihistamine.

More examples of additional active agents include (a) VLA-4 antagonists; (b) corticosteroids, such as beclomethasone, methylprednisolone, betamethasone, prednisone, prednisolone, dexamethasone, fluticasone and hydrocortisone, and corticosteroid analogs such as budesonide; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxepinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivative (e.g., diflunisal and flufenisal), oxicams (e.g., isoxicam, piroxicam, sudoxicam and tenoxicam), salicylates (e.g., acetyl salicylic acid, sulfasalazine and analogs, mesalamine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) interleukin inhibitors, such as interleukin-I (IL-I) inhibitors, and chemokine receptor antagonists; j) cholesterol lowering agents such as HMG-CoA reductase inhibitors (lovastatin, simvastatin, pravastatin, fluvastatin, atorvastatin and other statins), bile acid sequestrants (e.g., cholestyramine and colestipol), nicotinic acid (niacin), fibric acid derivatives (gemfibrozil, clofibrate, fenofibrate and benzafibrate), probucol and nitroglycerin; (k) anti-diabetic agents such as insulin, sulfonylureas (e.g., glyburide, meglinatide), biguanides, e.g., metformin (Glucophage®), α-glucosidase inhibitors (acarbose), thiazolidinone compounds, e.g., rosiglitazone (Avandia®), troglitazone (Rezulin®) and pioglitazone (Actos®); (l) preparations of interferon beta (interferon β-1 α, interferon β-1 β; (m) gold compounds such as auranofin and aurothioglucose, (n) etanercept (Enbrel®), (o) antibody therapies such as orthoclone (OKT3), dacli-zumab (Zenapax®), basiliximab (Simulect®), infliximab (Remicade®) and D2E6 TNF antibody, (p) lubricants or emollients such as petrolatum and lanolin, (q) keratolytic agents, (r) vitamin D3 derivatives, e.g., calcipotriene or calcipotriol (Dovonex®), (s) PUVA, (t) anthralin (Dritho-creme®), (u) etretinate (Tegison®) and isotretinoin, (v) multiple sclerosis therapeutic agents such as β-1 β (Betaseron®), interferon β-1 α (Avonex®), azathioprine (Imurek®, Imuran®), glatiramer acetate (Copaxone®), a glucocorticoid (e.g., prednisolone) and cyclophosphamide and (w) β3 adrenergic receptor agonists, leptin or derivatives thereof, and neuropeptide Y (e.g., NPY5) antagonists; (x) other compounds such as 5-aminosalicylic acid and prodrugs thereof; (y) DNA-alkylating agents (e.g., cyclophosphamide, ifosfamide), antimetabolites (e.g., azathioprine, 6-mercaptopurine, methotrexate, a folate antagonist, and 5-fluorouracil, a pyrimidine antagonist), microtubule disruptors (e.g., vincristine, vinblastine, paclitaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, and hormone therapy (e.g., tamoxifen, and flutamide).

In still other particular embodiments, compounds and compositions provided herein are administered for the treatment of rheumatoid arthritis, wherein the compounds are administered either alone or in combination with a second therapeutic agent selected from methotrexate, sulfasalazine, a COX-2 inhibitor, hydroxychloroquine, cyclosporine A, D-penicillamine, infliximab, etanercept, auranofin and aurothioglucose.

In yet other particular embodiments, the present compounds are administered for the treatment of inflammatory bowel disease wherein the compound of the invention is used alone or in combination with a second therapeutic agent selected from sulfasalazine and analogs (e.g., olsalazine) mesalamine, corticosteroids (e.g., prednisone, prednisolone) and analogs (e.g., budesonide), azathioprine, 6-mercaptopurine, cyclosporine A, methotrextate, infliximab, or an IL-1 inhibitor.

In other particular embodiments, the present methods are directed to the treatment of multiple sclerosis using a compound of the invention either alone or in combination with a second therapeutic agent selected from interferon β-1β, interferon β-1α, azathioprine, glatiramer acetate, a glucocorticoid (e.g., prednisolone), and cyclophosphamide.

EXAMPLES

The following examples, including experiments and results achieved, are provided for illustrative purposes only and are not to be construed as limiting the present invention. Where chemical structures depict atoms having an unfilled valency, it is to be understood that the valency is satisfied with one or more hydrogen atoms.

Example 1

Synthesis of N-(4-(hydroxymethyl)pyridin-2-yl)-6-(pyridin-4-yl)benzo [d]thiazol-2-amine (Compound 101, Structure 4 in Scheme I, $R^1$=CH$_2$OH, $R^4$=4-pyridyl)

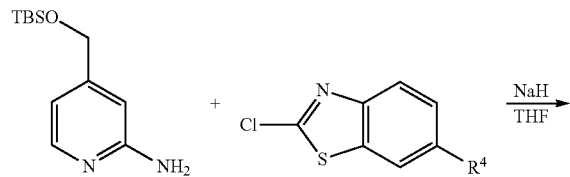

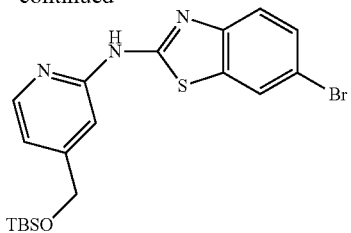

To a solution of 4-(((tert-butyldimethylsilyl)oxy)methyl) pyridin-2-amine (1.92 g, 8.0 mmol, 1 eq.) in anhydrous tetrahydrofuran (THF) (100 mL) was added NaH (2.25 g, 56.0 mmol, 7.0 eq) at 0° C., after stirring at room temperature for 30 min, a solution of 6-bromo-2-chlorobenzo[d] thiazole (2.0 g, 8.1 mmol, 1 eq) in THF (20 mL) was added dropwise. Then the reaction mixture was heated to 65° C. for 2 hours. After cooling, water was added, the organic layer was separated and the aqueous was extracted with EtOAc, dried and concentrated to give 6-bromo-N-(4-(((tert-butyldimethylsilyl)oxy)methyl)pyridin-2-yl)benzo[d]thiazol-2-amine (1.5 g, 37%) which was used directly without further purification. $^1$H NMR (500 MHz, CDCl$_3$) δ 8.03 (d, J=9.0, 1H); 6.87 (d, J=2.6, 1H); 6.64 (dd, J=9.0, 2.6, 1H); 4.58 (t, J=5.2, 1H); 3.67 (s, 3H); 3.21 (td, J=7.1, 5.2, 2H); 2.31 (t, J=7.5, 2H); 1.70-1.59 (m, 4H); 1.46-1.29 (m, 10H).

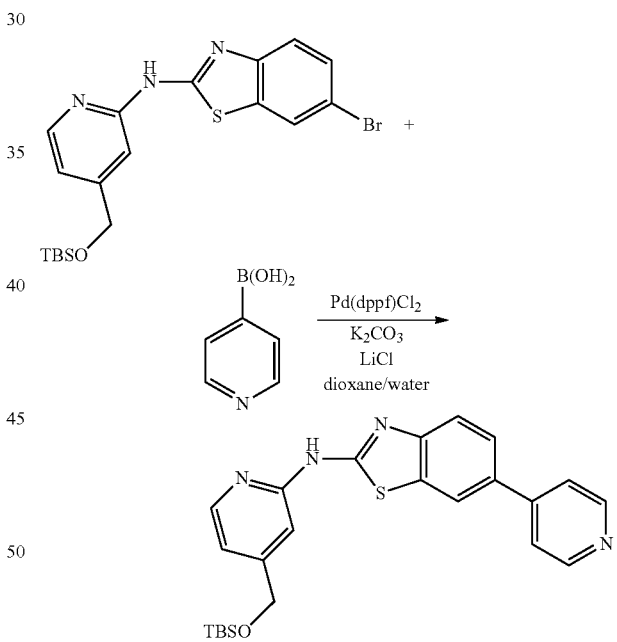

To a 10 mL microwave tube was added 6-bromo-N-(4-(((tert-butyldimethylsilyl)oxy)methyl)pyridin-2-yl)benzo[d] thiazol-2-amine (400 mg, 1.03 mmol), pyridine-4-boronic acid (185 mg, 1.5 eq), K$_2$CO$_3$ (425 mg, 3.09 mmol, 3 eq), Pd(dppf)Cl$_2$, (25 mg, 0.03 mmol, 0.03 eq), LiCl (130 mg, 3.09 mmol, 3 eq) and 3 mL of dioxane/H$_2$O(4:1). The mixture was stirred at 140° C. under microwave condition for 1 h. After cooling to room temperature (rt), the mixture was concentrated in vacuo and the residue was purified by flash chromatography to give 125 mg of N-(4-((((tert-butyldimethylsilyl)oxy)methyl)pyridin-2-yl)-6-(pyridin-4-yl)benzo [d]thiazol-2-amine.

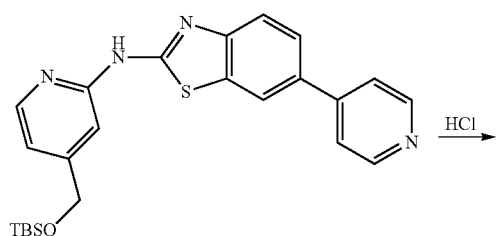

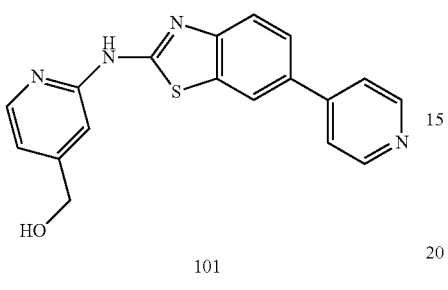

101

N-(4-4(Tert-butyldimethylsilyl)oxy)methyppyridin-2-yl)-6-(pyridin-4-yl)benzo[d]thiazol-2-amine (1.8 g, 3.34 mmol, 1 eq.) was dissolved in 6 N HCl/MeOH (30 mL), and the suspension was stirred at room temperature for 2 hours. After completion of the reaction, the solvent was evaporated and the residue was purified by chromatography to give 1.2 g of N-(4-(hydroxymethyl)pyridin-2-yl)-6-(pyridin-4-yl) benzo [d]thiazol-2-amine 101. $^1$HNMR (DMSO-$d_6$, 400 MHz) δ 8.95 (d, 2H), 8.75 (s, 1H), 8.45 (d, 2H), 8.35 (d, 1H), 8.11 (d, 1H), 7.84 (d, 1H), 7.22 (s, 1H), 7.00 (d, 1H), 4.60 (s, 2H). MS (ES-API): MH$^+$=335.0. HPLC $t_R$=2.20 min.

Example 2

Synthesis of 6-(pyridin-4-yl)-N-(4-(pyrrolidin-1-ylmethyl)pyridin-2-yl)benzo[d]thiazol-2-amine (Compound 102, Structure 4 in Scheme I, R$^1$=CH$_2$-pyrrolidin-1-yl, R$^4$=4-pyridyl)

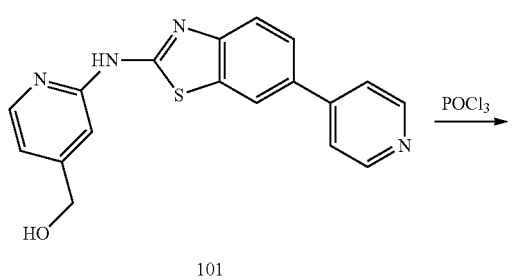

(2-((6-(Pyridin-4-yl)benzo[d]thiazol-2-yl)amino)pyridin-4-yl)methanol 101 (0.12 g, 0.36 mmol, 1 eq.) was dissolved in POCl3 (3 mL) under N2, and the suspension was stirred at 110° C. for 2 hours. After cooling, POCl3 was evaporated under reduced pressure and the residue was basified with sat. Na2CO3 solution, then extracted with DCM, dried and concentrated in vacuo to afford N-(4-(chloromethyppyridin-2-yl)-6-(pyridin-4-yl)benzo[d]thiazol-2-amine (80 mg, 63%) which was used directly in the next step.

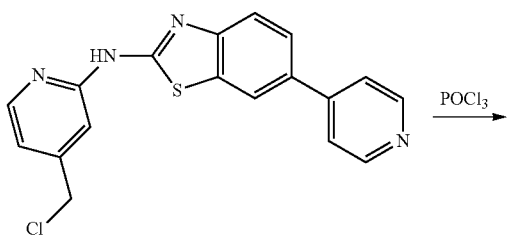

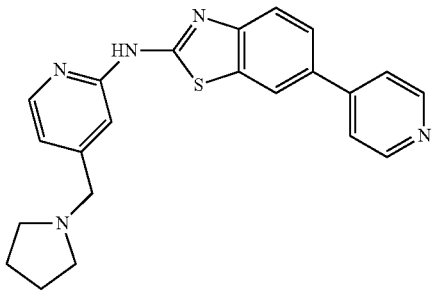

102

A solution of N-(4-(chloromethyl)pyridin-2-yl)-6-(pyridin-4-yl)benzo[d]thiazol-2-amine (80 mg, 0.23 mmol, 1 eq.) in 1 mL dioxane was treated with 15 mg of pyrrolidine and 20 mg DIEA. The reaction mixture was stirred at 140° C. under microwave condition for 1 h. After cooling to rt, the mixture was concentrated in vacuo. The residue was washed with EtOH to afford 6-(pyridin-4-yl)-N-(4-(pyrrolidin-1-ylmethyl)pyridin-2-yl)benzo[d]thiazol-2-amine 102 without further purification (67 mg). $^1$HNMR (CD$_3$OD, 400 MHz) δ8.83 (d, 2H), 8.60 (m, 1H), 8.54 (m, 1H), 8.46 (m, 2H), 8.10 (m, 1H), 7.92 (d, 1H), 7.52 (s, 1H), 3.37 (d, 1H), 4.53 (s, 2H), 3.62 (br s, 2H), 3.25 (m, 2H overlapping with signal from CD$_3$OD), 2.22 (m, 2H), 2.09 (m, 2H). MS (ES-API): MH$^+$=388.1. HPLC $t_R$=2.16 min.

Examples 3-332

Compounds 103-439 were prepared in a similar fashion as described in Examples 1-2 and their structures, names, and found molecular mass ion numbers are summarized in Table 1 (Example: E.g.; Compound: Cmpd).

TABLE 1

| E.g. | Structure | Cmpd | Name | [M + H]+ |
|---|---|---|---|---|
| 3 | 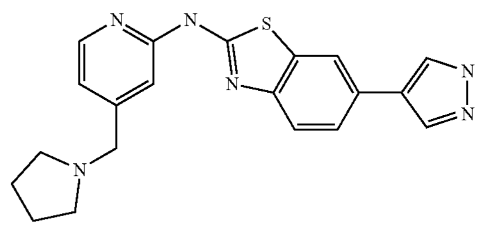 [SMILES: c1cc(CN2CCCC2)cc(Nc2nc3ccc(-c4cn[nH]c4)cc3s2)n1] | 103 | 6-(1H-pyrazol-4-yl)-N-(4-(pyrrolidin-1-ylmethyl)-pyridin-2-yl)benzo[d]-thiazol-2-amine | 377.1 |
| 4 | 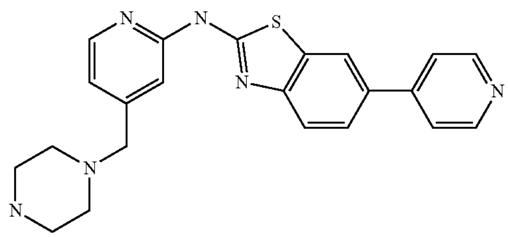 [SMILES: c1cc(-c2ccc3nc(Nc4cc(CN5CCNCC5)ccn4)sc3c2)ccn1] | 104 | N-(4-(piperazin-1-yl-methyl)pyridin-2-yl)-6-(pyridin-4-yl)benzo[d]-thiazol-2-amine | 403.1 |
| 5 | 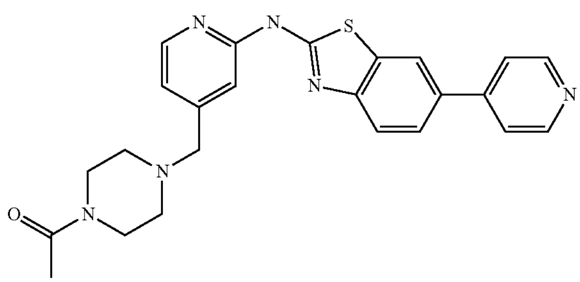 [SMILES: CC(=O)N1CCN(Cc2ccnc(Nc3nc4ccc(-c5ccncc5)cc4s3)c2)CC1] | 105 | 1-(4-((2-((6-(pyridin-4-yl)benzo[d]thiazol-2-yl)-amino)pyridin-4-yl)-methyl)piperazin-1-yl)-ethanone | 445.1 |
| 6 | 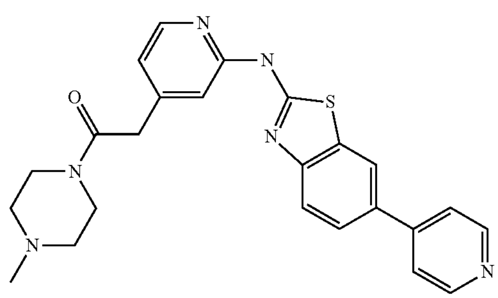 [SMILES: CN1CCN(C(=O)Cc2ccnc(Nc3nc4ccc(-c5ccncc5)cc4s3)c2)CC1] | 106 | 1-(4-methylpiperazin-1-yl)-2-(2-((6-(pyridin-4-yl)benzo[d]thiazol-2-yl)-amino)pyridin-4-yl)-ethanone | 445.1 |
| 7 | 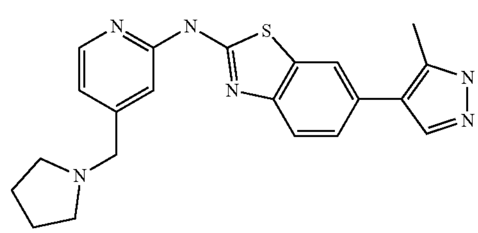 [SMILES: Cc1[nH]ncc1-c1ccc2nc(Nc3cc(CN4CCCC4)ccn3)sc2c1] | 107 | 6-(5-methyl-1H-pyrazol-4-yl)-N-(4-(pyrrolidin-1-ylmethyl)pyridin-2-yl)-benzo[d]thiazol-2-amine | 391.1 |
| 8 | 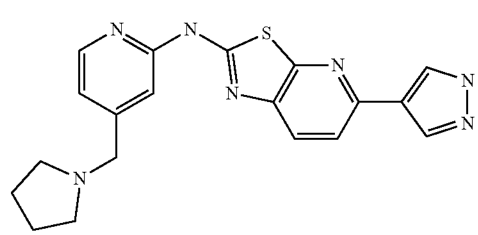 [SMILES: c1cc(CN2CCCC2)cc(Nc2nc3ccc(-c4cn[nH]c4)nc3s2)n1] | 108 | 5-(1H-pyrazol-4-yl)-N-(4-(pyrrolidin-1-ylmethyl)-pyridin-2-yl)thiazolo-[5,4-b]pyridin-2-amine | 378.1 |

TABLE 1-continued

| E.g. | Cmpd | Name | [M + H]⁺ |
|---|---|---|---|
| 9 | 109 | N-(4-morpholinopyridin-2-yl)-6-(1H-pyrazol-4-yl)benzo[d]thiazol-2-amine | 379.1 |
| 10 | 110 | N-(4-morpholinopyridin-2-yl)-5-(1H-pyrazol-4-yl)thiazolo[5,4-b]pyridin-2-amine | 380.1 |
| 11 | 111 | (2-((6-(1H-pyrazol-4-yl)-benzo[d]thiazol-2-yl)-amino)pyridin-4-yl)-methanol | 324.0 |
| 12 | 112 | N-(4-(4-(2-methoxyethyl)-piperazin-1-yl)pyridin-2-yl)-5-(1H-pyrazol-4-yl)-thiazolo[5,4-b]pyridin-2-amine | 437.1 |
| 13 | 113 | N-(4-((dimethylamino)-methyl)pyridin-2-yl)-5-(1H-pyrazol-4-yl)thiazolo-[5,4-b]pyridin-2-amine | 352.0 |
| 14 | 114 | N-(4-(4-(2-methoxyethyl)-piperazin-1-yl)-pyridin-2-yl)-5-(pyridin-4-yl)thiazolo-[5,4-b]pyridin-2-amine | 448.1 |

TABLE 1-continued

| E.g. | Structure | Cmpd | Name | [M + H]+ |
|---|---|---|---|---|
| 15 | 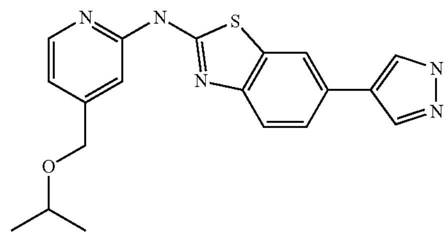 [SMILES: CC(C)OCc1ccnc(Nc2nc3ccc(-c4cn[nH]c4)cc3s2)c1] | 115 | N-(4-(isopropoxymethyl)-pyridin-2-yl)-6-(1H-pyrazol-4-yl)benzo[d]-thiazol-2-amine | 366.0 |
| 16 | 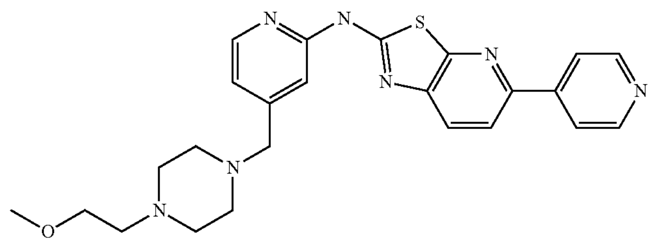 [SMILES: COCCN1CCN(Cc2ccnc(Nc3nc4ccc(-c5ccncc5)nc4s3)c2)CC1] | 116 | N-(4-((4-(2-methoxyethyl)-piperazin-1-yl)methyl)-pyridin-2-yl)-5-(pyridin-4-yl)thiazolo[5,4-b]pyridin-2-amine | 462.2 |
| 17 | 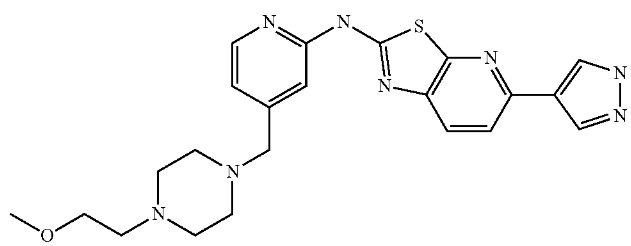 [SMILES: COCCN1CCN(Cc2ccnc(Nc3nc4ccc(-c5cn[nH]c5)nc4s3)c2)CC1] | 117 | N-(4-((4-(2-methoxyethyl)-piperazin-1-yl)methyl)-pyridin-2-yl)-5-(1H-pyrazol-4-yl)thiazolo-[5,4-b]pyridin-2-amine | 451.2 |
| 18 | 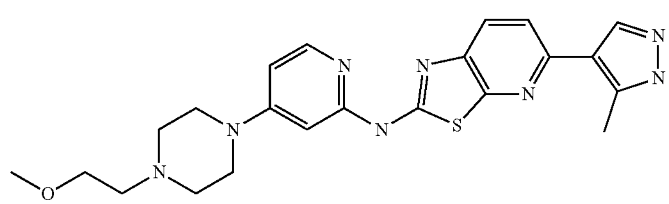 [SMILES: COCCN1CCN(c2ccnc(Nc3nc4ccc(-c5cn[nH]c5C)nc4s3)c2)CC1] | 118 | N-(4-(4-(2-methoxyethyl)-piperazin-1-yl)pyridin-2-yl)-5-(5-methyl-1H-pyrazol-4-yl)thiazolo-[5,4-b]pyridin-2-amine | 451.2 |
| 19 | 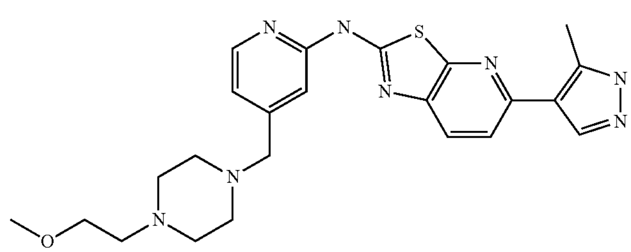 | 119 | N-(4-((4-(2-methoxyethyl)-piperazin-1-yl)methyl)-pyridin-2-yl)-5-(5-methyl-1H-pyrazol-4-yl)thiazolo-[5,4-b]pyridin-2-amine | 465.2 |
| 20 | 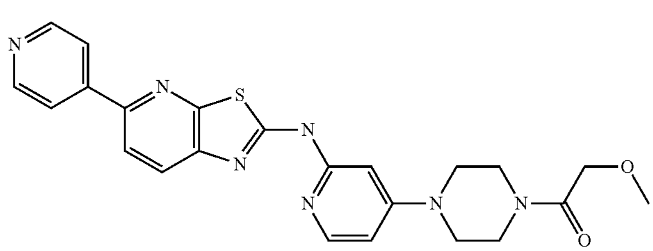 | 120 | 2-methoxy-1-(4-(2-((5-(pyridin-4-yl)thiazolo-[5,4-b]pyridin-2-yl)-amino)pyridin-4-yl)-piperazin-1-yl)ethanone | 462.1 |

US 11,773,110 B2

TABLE 1-continued

| E.g. | Structure | Cmpd | Name | [M + H]+ |
|---|---|---|---|---|
| 21 | 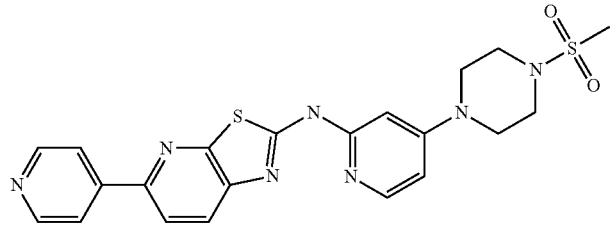 [SMILES: CS(=O)(=O)N1CCN(c2ccnc(Nc3nc4ccc(-c5ccncc5)nc4s3)c2)CC1] | 121 | N-(4-(4-(methylsulfonyl)-piperazin-1-yl)pyridin-2-yl)-5-(pyridin-4-yl)thiazolo-[5,4-b]pyridin-2-amine | 468.1 |
| 22 | 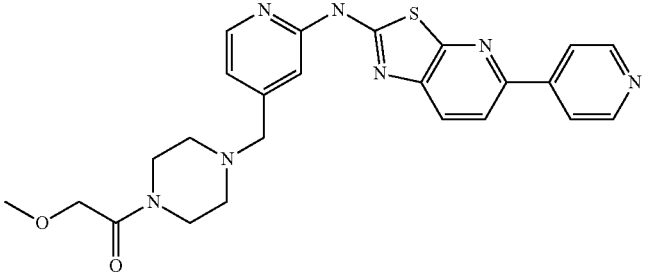 [SMILES: COCC(=O)N1CCN(Cc2ccnc(Nc3nc4ccc(-c5ccncc5)nc4s3)c2)CC1] | 122 | 2-methoxy-1-(4-((2-((5-(pyridin-4-yl)thiazolo[5,4-b]pyridin-2-yl)amino)-pyridin-4-yl)methyl)-piperazin-1-yl)ethanone | 476.2 |
| 23 | 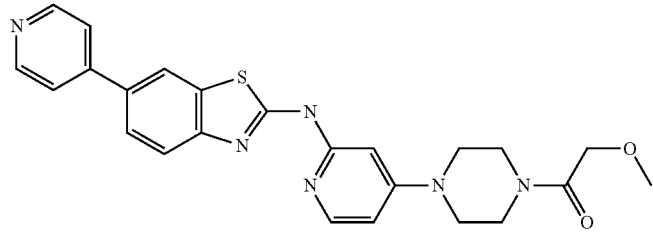 | 123 | 2-methoxy-1-(4-(2-((6-(pyridin-4-yl)benzo[d]-thiazol-2-yl)amino)-pyridin-4-yl)piperazin-1-yl)ethanone | 461.1 |
| 24 | 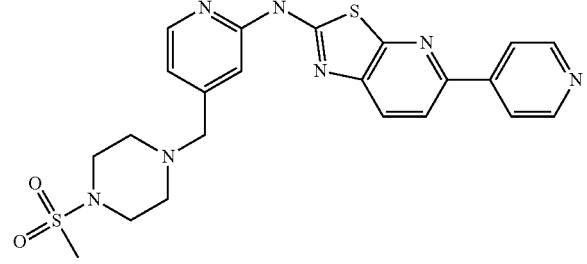 [SMILES: CS(=O)(=O)N1CCN(Cc2ccnc(Nc3nc4ccc(-c5ccncc5)nc4s3)c2)CC1] | 124 | N-(4-((4-(methylsulfonyl)-piperazin-1-yl)methyl)-pyridin-2-yl)-5-(pyridin-4-yl)thiazolo[5,4-b]-pyridin-2-amine | 482.1 |
| 25 | 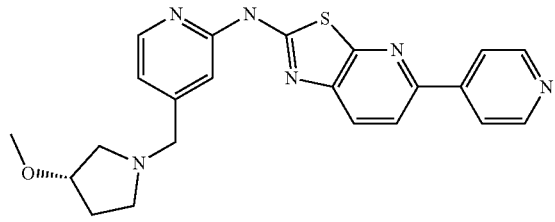 [SMILES: CO[C@H]1CCN(Cc2ccnc(Nc3nc4ccc(-c5ccncc5)nc4s3)c2)C1] | 125 | (S)-N-(4-((3-methoxy-pyrrolidin-1-yl)methyl)-pyridin-2-yl)-5-(pyridin-4-yl)thiazolo[5,4-b]-pyridin-2-amine | 419.1 |
| 26 | 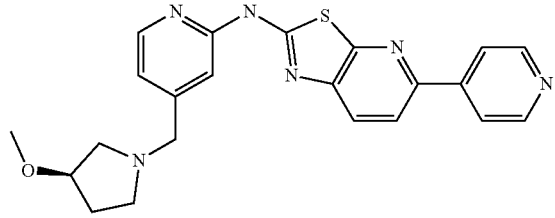 [SMILES: CO[C@@H]1CCN(Cc2ccnc(Nc3nc4ccc(-c5ccncc5)nc4s3)c2)C1] | 126 | (R)-N-(4-((3-methoxy-pyrrolidin-1-yl)methyl)-pyridin-2-yl)-5-(pyridin-4-yl)thiazolo[5,4-b]-pyridin-2-amine | 419.1 |

TABLE 1-continued

| E.g. | Structure | Cmpd | Name | [M + H]+ |
|---|---|---|---|---|
| 27 | 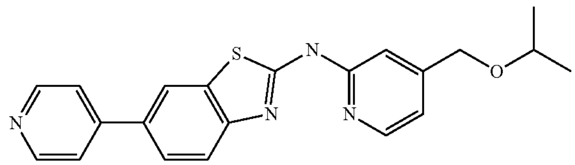 [SMILES: CC(C)OCc1ccnc(Nc2nc3ccc(-c4ccncc4)cc3s2)c1] | 127 | N-(4-(isopropoxymethyl)-pyridin-2-yl)-6-(pyridin-4-yl)benzo[d]thiazol-2-amine | 377.2 |
| 28 | 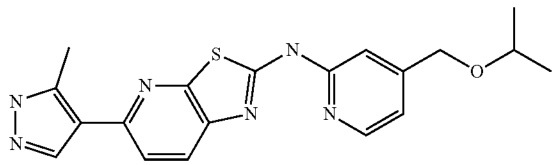 [SMILES: Cc1[nH]ncc1-c1ccc2nc(Nc3cc(COC(C)C)ccn3)sc2n1] | 128 | N-(4-(isopropoxymethyl)-pyridin-2-yl)-5-(5-methyl-1H-pyrazol-4-yl)thiazolo-[5,4-b]pyridin-2-amine | 381.1 |
| 29 | 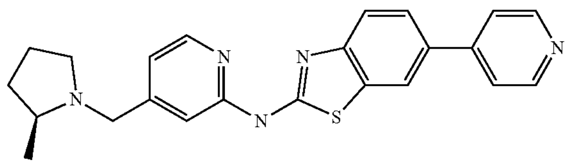 [SMILES: C[C@H]1CCCN1Cc1ccnc(Nc2nc3ccc(-c4ccncc4)cc3s2)c1] | 129 | (S)-N-(4-((2-methyl-pyrrolidin-1-yl)methyl)-pyridin-2-yl)-6-(pyridin-4-yl)benzo[d]thiazol-2-amine | 402.1 |
| 30 | 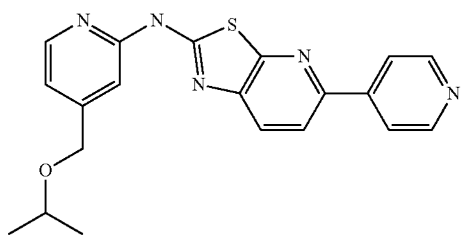 [SMILES: CC(C)OCc1ccnc(Nc2nc3ccc(-c4ccncc4)nc3s2)c1] | 130 | N-(4-(isopropoxymethyl)-pyridin-2-yl)-5-(pyridin-4-yl)thiazolo[5,4-b]pyridin-2-amine | 378.1 |
| 31 | 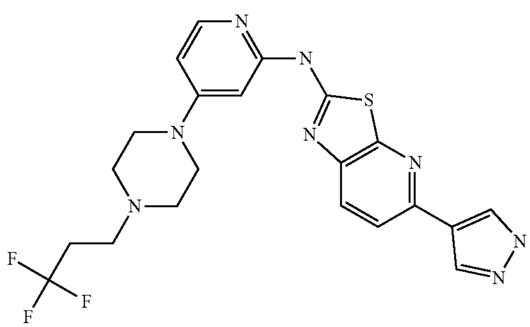 [SMILES: FC(F)(F)CCN1CCN(c2ccnc(Nc3nc4ccc(-c5cn[nH]c5)nc4s3)c2)CC1] | 131 | 5-(1H-pyrazol-4-yl)-N-(4-(4-(3,3,3-trifluoropropyl)-piperazin-1-yl)pyridin-2-yl)thiazolo[5,4-b]pyridin-2-amine | 475.2 |
| 32 | 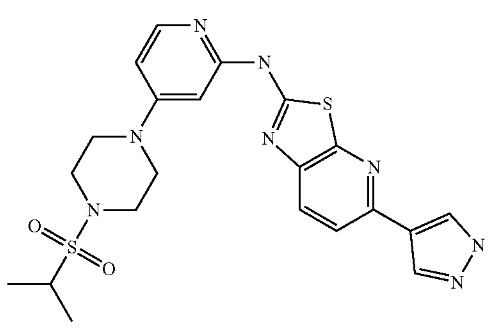 [SMILES: CC(C)S(=O)(=O)N1CCN(c2ccnc(Nc3nc4ccc(-c5cn[nH]c5)nc4s3)c2)CC1] | 132 | N-(4-(4-(isopropylsulfonyl)piperazin-1-yl)-pyridin-2-yl)-5-(1H-pyrazol-4-yl)thiazolo-[5,4-b]pyridin-2-amine | 485.1 |

TABLE 1-continued

| E.g. | Structure | Cmpd | Name | [M + H]+ |
|---|---|---|---|---|
| 33 | 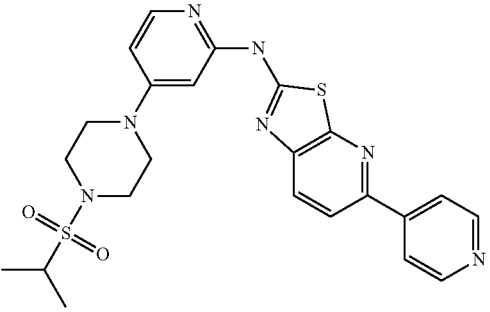 [SMILES: CC(C)S(=O)(=O)N1CCN(c2ccnc(Nc3nc4ccc(-c5ccncc5)nc4s3)c2)CC1] | 133 | N-(4-(4-(isopropylsulfonyl)piperazin-1-yl)-pyridin-2-yl)-5-(pyridin-4-yl)thiazolo[5,4-b]-pyridin-2-amine | 496.0 |
| 34 | 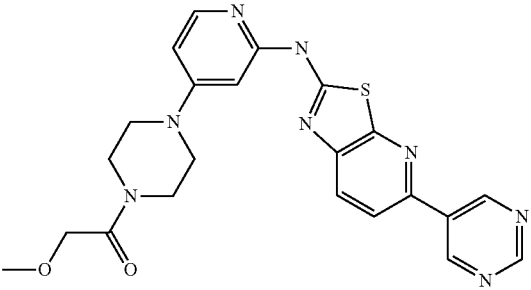 [SMILES: COCC(=O)N1CCN(c2ccnc(Nc3nc4ccc(-c5cncnc5)nc4s3)c2)CC1] | 134 | 2-methoxy-1-(4-(2-((5-(pyrimidin-5-yl)thiazolo-[5,4-b]pyridin-2-yl)-amino)pyridin-4-yl)-piperazin-1-yl)ethanone | 463.1 |
| 35 | 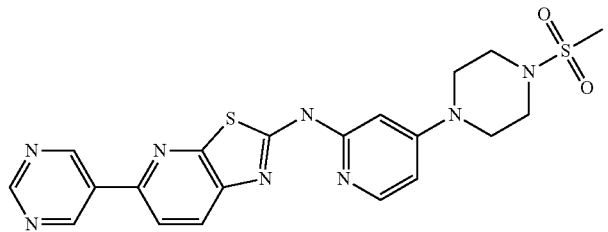 [SMILES: CS(=O)(=O)N1CCN(c2ccnc(Nc3nc4ccc(-c5cncnc5)nc4s3)c2)CC1] | 135 | N-(4-(4-(methylsulfonyl)-piperazin-1-yl)pyridin-2-yl)-5-(pyrimidin-5-yl)-thiazolo[5,4-b]pyridin-2-amine | 469.1 |
| 36 | 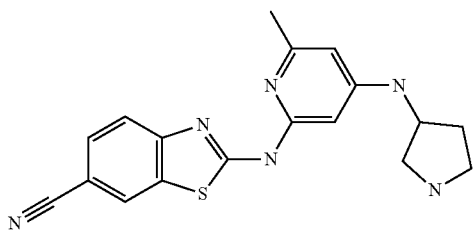 [SMILES: Cc1cc(NC2CCNC2)cc(Nc2nc3ccc(C#N)cc3s2)n1] | 136 | 2-((6-methyl-4-(pyrrolidin-3-ylamino)pyridin-2-yl)-amino)benzo[d]thiazole-6-carbonitrile | 351.1 |
| 37 | 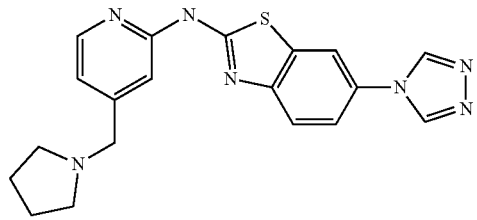 [SMILES: c1cc(CN2CCCC2)cc(Nc2nc3ccc(-n4cnnc4)cc3s2)n1] | 137 | N-(4-(pyrrolidin-1-ylmethyl)pyridin-2-yl)-6-(4H-1,2,4-triazol-4-yl)-benzo[d]thiazol-2-amine | 378.1 |
| 38 | 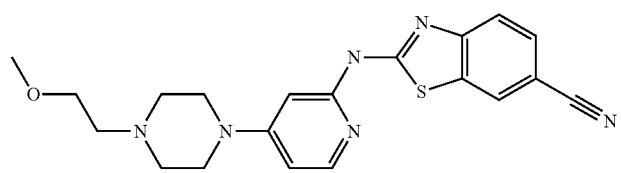 [SMILES: COCCN1CCN(c2ccnc(Nc3nc4ccc(C#N)cc4s3)c2)CC1] | 143 | 2-((4-(4-(2-methoxyethyl)-piperazin-1-yl)pyridin-2-yl)amino)benzo[d]thiazole-6-carbonitrile | 394.95 |

TABLE 1-continued

| E.g. | Cmpd | Name | [M + H]+ |
|---|---|---|---|
| 39 | 144 | 5-(5-methyl-1H-pyrazol-4-yl)-N-(4-((tetrahydro-2H-pyran-4-yl)oxy)pyridin-2-yl)thiazolo[5,4-b]pyridin-2-amine | 409.1 |
| 40 | 146 | N-(4-(4-(2-methoxyethyl)-piperazin-1-yl)pyridin-2-yl)-5-(pyridazin-4-yl)-thiazolo[5,4-b]pyridin-2-amine | 449.1 |
| 41 | 147 | 1-(4-(2-((5-ethylthiazolo-[5,4-b]pyridin-2-yl)amino)-pyridin-4-yl)piperazin-1-yl)-2-methoxyethanone | 413.1 |
| 42 | 148 | 1-((2-((5-(pyridin-4-yl)-thiazolo[5,4-b]pyridin-2-yl)amino)pyridin-4-yl)-methyl)pyrrolidin-2-one | 403.1 |
| 43 | 149 | 1-((2-((5-(1H-pyrazol-4-yl)thiazolo[5,4-b]pyridin-2-yl)amino)pyridin-4-yl)methyl)pyrrolidin-2-one | 392.1 |
| 44 | 150 | 2-methoxy-1-(4-(2-((5-(pyridin-4-yl)thiazolo[5,4-b]pyridin-2-yl)amino)-pyridin-4-yl)piperidin-1-yl)ethanone | 461.1 |
| 45 | 151 | N2-(benzo[d]thiazol-2-yl)-N4-(bicyclo[2.2.1]heptan-2-yl)-N6-((R)-pyrrolidin-3-yl)-1,3,5-triazine-2,4,6-triamine | |

TABLE 1-continued

| E.g. | Structure | Cmpd | Name | [M + H]+ |
|---|---|---|---|---|
| 46 | 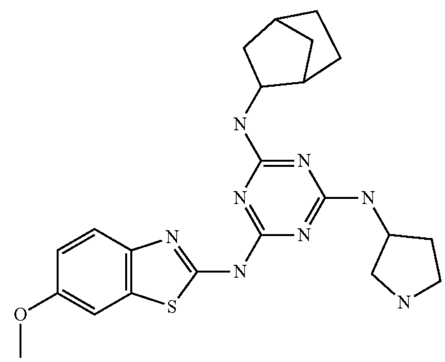 [SMILES: COc1ccc2nc(Nc3nc(NC4CCNC4)nc(NC4CC5CCC4C5)n3)sc2c1] | 152 | $N^2$-(bicyclo[2.2.1]heptan-2-yl)-$N^4$-(6-methoxybenzo[d]thiazol-2-yl)-$N^6$-(pyrrolidin-3-yl)-1,3,5-triazine-2,4,6-triamine | |
| 47 | 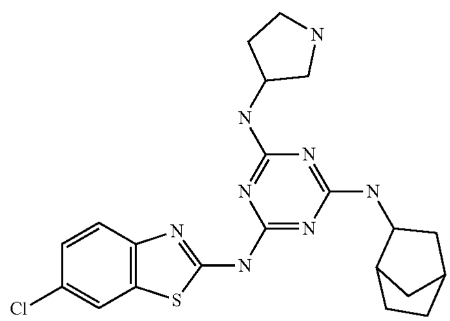 [SMILES: Clc1ccc2nc(Nc3nc(NC4CCNC4)nc(NC4CC5CCC4C5)n3)sc2c1] | 153 | $N^2$-(bicyclo[2.2.1]heptan-2-yl)-$N^4$-(6-chlorobenzo[d]thiazol-2-yl)-$N^6$-(pyrrolidin-3-yl)-1,3,5-triazine-2,4,6-triamine | |
| 48 | 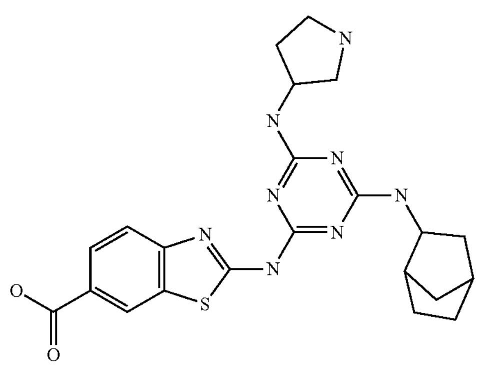 [SMILES: O=C(O)c1ccc2nc(Nc3nc(NC4CCNC4)nc(NC4CC5CCC4C5)n3)sc2c1] | 154 | 2-((4-(bicyclo[2.2.1]heptan-2-ylamino)-6-(pyrrolidin-3-ylamino)-1,3,5-triazin-2-yl)amino)benzo[d]thiazole-6-carboxylic acid | |
| 49 | 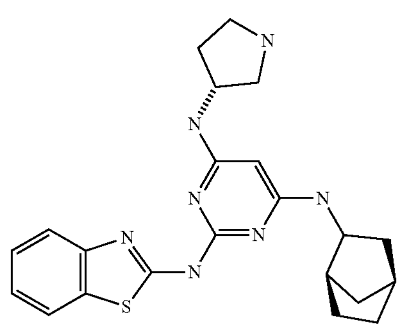 | 155 | $N^2$-(benzo[d]thiazol-2-yl)-$N^4$-((1R,4S)-bicyclo-[2.2.1]heptan-2-yl)-$N^6$-((R)-pyrrolidin-3-yl)-pyrimidine-2,4,6-triamine | |
| 50 | 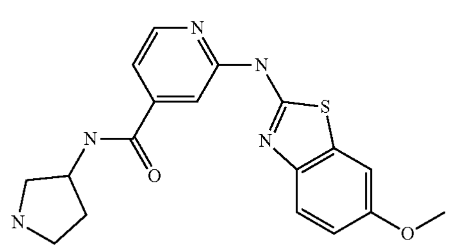 [SMILES: COc1ccc2nc(Nc3cc(C(=O)NC4CCNC4)ccn3)sc2c1] | 156 | 2-((6-methoxybenzo[d]thiazol-2-yl)amino)-N-(pyrrolidin-3-yl)-isonicotinamide | 370.1 |

TABLE 1-continued

| E.g. | Cmpd | Name | [M + H]⁺ |
|---|---|---|---|
| 51 | 157 | 2-((6-cyanobenzo[d]-thiazol-2-yl)amino)-N-(pyrrolidin-3-yl)iso-nicotinamide | 365.0 |
| 52 | 158 | 2-((6-chlorobenzo[d]-thiazol-2-yl)amino)-N-(pyrrolidin-3-yl)-iso-nicotinamide | 374.0 |
| 53 | 159 | (R)-2-((2-((4-methylamino)-6-(pyrrolidin-3-ylamino)-1,3,5-triazin-2-yl)amino)-benzo[d]thiazol-6-yl)oxy)-ethanol | |
| 54 | 160 | (S)-2-((6-methoxybenzo-[d]thiazol-2-yl)amino)-N-(pyrrolidin-3-yl)iso-nicotinamide | 370.0 |
| 55 | 161 | (S)-2-((6-cyanobenzo-[d]thiazol-2-yl)amino)-N-(pyrrolidin-3-yl)iso-nicotinamide | 365.0 |
| 56 | 162 | (R)-2-((6-cyanobenzo-[d]thiazol-2-yl)amino)-N-(pyrrolidin-3-yl)iso-nicotinamide | 365.0 |

TABLE 1-continued

| E.g. | Structure | Cmpd | Name | [M + H]+ |
|---|---|---|---|---|
| 57 | 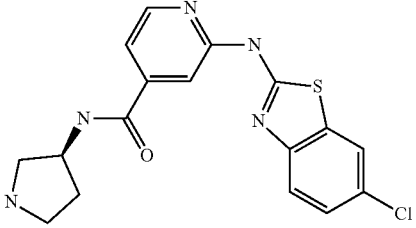 | 163 | (S)-2-((6-chlorobenzo-[d]thiazol-2-yl)amino)-N-(pyrrolidin-3-yl)iso-nicotinamide | 373.9 |
| 58 | 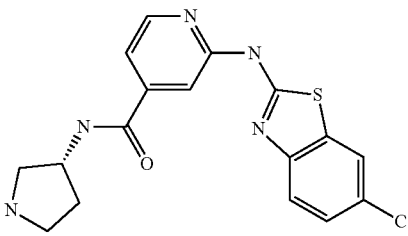 | 164 | (R)-2-((6-chlorobenzo-[d]thiazol-2-yl)amino)-N-(pyrrolidin-3-yl)iso-nicotinamide | 374.0 |
| 59 | 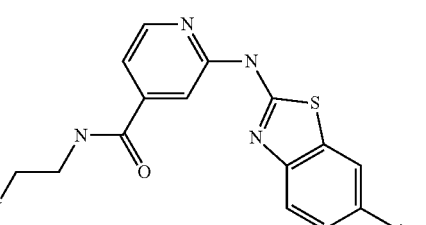 | 165 | N-(2-aminoethyl)-2-((6-cyanobenzo[d]thiazol-2-yl)amino)isonicotinamide | 339.0 |
| 60 | 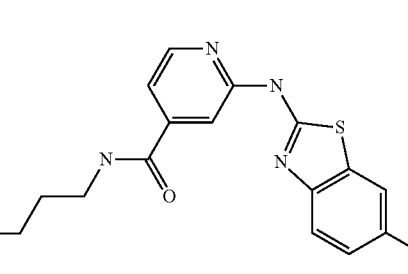 | 166 | N-(4-aminobutyl)-2-((6-cyanobenzo[d]thiazol-2-yl)amino)isonicotinamide | 367.1 |
| 61 | 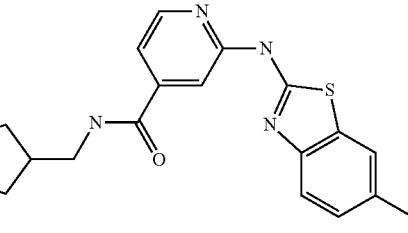 | 167 | 2-((6-cyanobenzo[d]thiazol-2-yl)amino)-N-(pyrrolidin-3-ylmethyl)isonicotinamide | 379.1 |
| 62 | 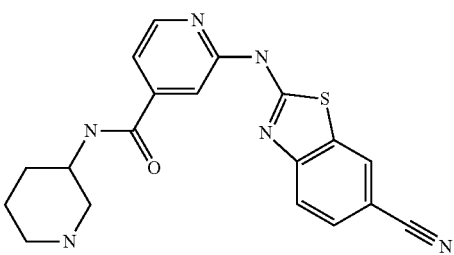 [SMILES: N#Cc1ccc2nc(Nc3cc(C(=O)NC4CCCNC4)ccn3)sc2c1] | 168 | 2-((6-cyanobenzo[d]thiazol-2-yl)amino)-N-(piperidin-3-yl)isonicotinamide | 379.1 |

TABLE 1-continued

| E.g. | Cmpd | Name | [M + H]+ |
|---|---|---|---|
| 63 | 169 | 2-((6-cyanobenzo[d]thiazol-2-yl)amino)-N-(pyrrolidin-2-ylmethyl)isonicotinamide | 379.0 |
| 64 | 170 | 2-((4-(3-aminopiperidine-1-carbonyl)pyridin-2-yl)amino)benzo[d]thiazole-6-carbonitrile | 379.0 |
| 65 | 171 | $N^2$-(6-methoxybenzo[d]thiazol-2-yl)-$N^4$-(pyrrolidin-3-yl)-pyridine-2,4-diamine | 342.0 |
| 66 | 172 | $N^2$-(6-chlorobenzo[d]thiazol-2-yl)-$N^4$-(pyrrolidin-3-yl)pyridine-2,4-diamine | 346.0 |
| 67 | 173 | (S)-2-((6-bromobenzo[d]thiazol-2-yl)amino)-N-(pyrrolidin-3-yl)isonicotinamide | 418.0 |
| 68 | 174 | (S)-2-((6-cyanobenzo[d]thiazol-2-yl)amino)-N-methyl-N-(pyrrolidin-3-yl)isonicotinamide | 379.0 |

TABLE 1-continued

| E.g. | Cmpd | Name | [M + H]⁺ |
|---|---|---|---|
| 69 | 175 | 2-((4-(pyrrolidin-3-ylamino)pyridin-2-yl)amino)benzo[d]thiazole-6-carbonitrile | 337.1 |
| 70 | 176 | (S)-2-((6-(pyridin-4-yl)benzo[d]thiazol-2-yl)amino)-N-(pyrrolidin-3-yl)isonicotinamide | 417.1 |
| 71 | 177 | (S)-2-((6-(pyridin-3-yl)benzo[d]thiazol-2-yl)amino)-N-(pyrrolidin-3-yl)isonicotinamide | 417.1 |
| 72 | 178 | (S)-2-((6-(1-methyl-1H-pyrazol-4-yl)benzo[d]thiazol-2-yl)amino)-N-(pyrrolidin-3-yl)isonicotinamide | 420.1 |
| 73 | 179 | (S)-2-((6-(1H-pyrazol-4-yl)benzo[d]thiazol-2-yl)amino)-N-(pyrrolidin-3-yl)isonicotinamide | 406.2 |

TABLE 1-continued

| E.g. | Structure | Cmpd | Name | [M + H]⁺ |
|---|---|---|---|---|
| 74 | 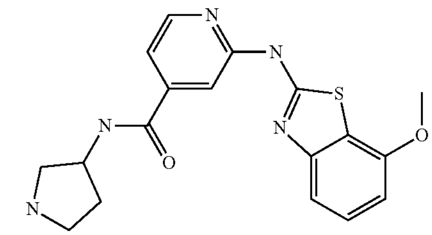 [SMILES: COc1cccc2nc(Nc3cc(C(=O)NC4CCNC4)ccn3)sc12] | 180 | 2-((7-methoxybenzo[d]-thiazol-2-yl)amino)-N-(pyrrolidin-3-yl)iso-nicotinamide | 370.0 |
| 75 | 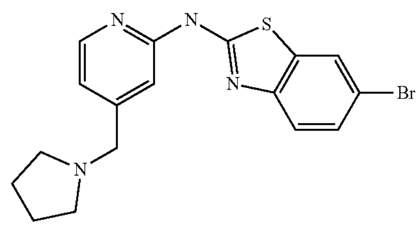 [SMILES: Brc1ccc2nc(Nc3cc(CN4CCCC4)ccn3)sc2c1] | 181 | 6-bromo-N-(4-(pyrrolidin-1-ylmethyl)pyridin-2-yl)-benzo[d]thiazol-2-amine | 391.0 |
| 76 | 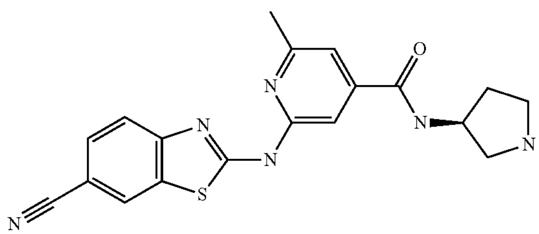 [SMILES: Cc1cc(C(=O)N[C@H]2CCNC2)cc(Nc2nc3ccc(C#N)cc3s2)n1] | 182 | (S)-2-((6-cyanobenzo[d]-thiazol-2-yl)amino)-6-methyl-N-(pyrrolidin-3-yl)isonicotinamide | 379.1 |
| 77 | 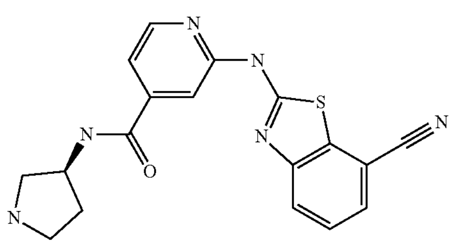 [SMILES: N#Cc1cccc2nc(Nc3cc(C(=O)N[C@H]4CCNC4)ccn3)sc12] | 183 | (S)-2-((7-cyanobenzo-[d]thiazol-2-yl)amino)-N-(pyrrolidin-3-yl)iso-nicotinamide | 365.0 |
| 78 | 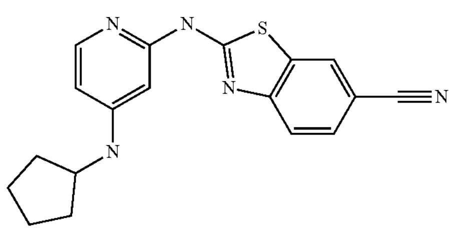 [SMILES: N#Cc1ccc2nc(Nc3cc(NC4CCCC4)ccn3)sc2c1] | 184 | 2-((4-(cyclopentylamino)-pyridin-2-yl)amino)benzo-[d]thiazole-6-carbonitrile | 336.0 |
| 79 | 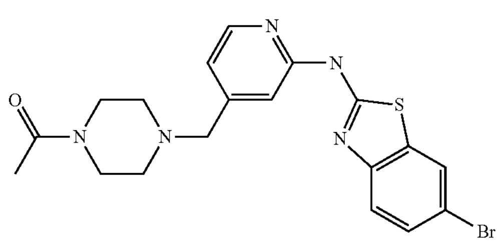 [SMILES: CC(=O)N1CCN(Cc2ccnc(Nc3nc4ccc(Br)cc4s3)c2)CC1] | 185 | 1-(4-((2-((6-bromobenzo-[d]thiazol-2-yl)amino)-pyridin-4-yl)methyl)-piperazin-1-yl)ethanone | 445.9 |

TABLE 1-continued

| E.g. | Cmpd | Name | [M + H]+ |
|---|---|---|---|
| 80 | 186 | 1-(4-((2-((6-(1H-pyrazol-4-yl)benzo[d]thiazol-2-yl)amino)pyridin-4-yl)methyl)piperazin-1-yl)ethanone | |
| 81 | 187 | N-(4-(piperidin-1-ylmethyl)pyridin-2-yl)-6-(1H-pyrazol-4-yl)benzo[d]thiazol-2-amine | |
| 82 | 188 | 2-((5-methyl-4-(pyrrolidin-3-ylamino)pyridin-2-yl)amino)benzo[d]thiazole-6-carbonitrile | 351.1 |
| 83 | 189 | 6-(pyridin-3-yl)-N-(4-(pyrrolidin-1-ylmethyl)pyridin-2-yl)benzo[d]thiazol-2-amine | |
| 84 | 190 | 1-((2-((6-bromobenzo[d]thiazol-2-yl)amino)pyridin-4-yl)methyl)piperidin-4-ol | |
| 85 | 191 | 2-(((2-((6-bromobenzo[d]thiazol-2-yl)amino)pyridin-4-yl)methyl)(methyl)amino)ethanol | |

TABLE 1-continued

| E.g. | Cmpd | Name | [M + H]⁺ |
|---|---|---|---|
| 86 | 192 | 6-bromo-N-(4-((dimethyl-amino)methyl)pyridin-2-yl)benzo[d]thiazol-2-amine | |
| 87 | 193 | 6-((6-(1H-pyrazol-4-yl)-benzo[d]thiazol-2-yl)-amino)-N-(pyrrolidin-3-yl)picolinamide | 406.1 |
| 88 | 194 | 6-(1H-pyrazol-5-yl)-N-(4-(pyrrolidin-1-ylmethyl)-pyridin-2-yl)benzo[d]-thiazol-2-amine | |
| 89 | 195 | 2-((4-((2-aminopropyl)-amino)pyridin-2-yl)-amino)benzo[d]thiazole-6-carbonitrile | 325.1 |
| 90 | 196 | 2-((4-((1-aminopropan-2-yl)amino)pyridin-2-yl)amino)benzo[d]-thiazole-6-carbonitrile | 325.1 |
| 91 | 197 | N-((2-((6-(pyridin-4-yl)-benzo[d]thiazol-2-yl)-amino)pyridin-4-yl)-methyl)methanesulfon-amide | 412.1 |

TABLE 1-continued

| E.g. | Cmpd | Name | [M + H]+ |
|---|---|---|---|
| 92 | 198 | N-(4-(piperidin-1-ylmethyl)pyridin-2-yl)-6-(pyridin-4-yl)benzo[d]thiazol-2-amine | 402.1 |
| 93 | 199 | N-(4-((dimethylamino)methyl)pyridin-2-yl)-6-(pyridin-4-yl)benzo[d]thiazol-2-amine | 362.1 |
| 94 | 200 | 4-((6-(1H-pyrazol-4-yl)benzo[d]thiazol-2-yl)amino)-N-(pyrrolidin-3-yl)picolinamide | 406.1 |
| 95 | 201 | 6-(6-methoxypyridin-3-yl)-N-(4-(pyrrolidin-1-ylmethyl)pyridin-2-yl)benzo[d]thiazol-2-amine | 418.2 |
| 96 | 202 | N-(4-(4-methylpiperazin-1-yl)pyridin-2-yl)-6-(pyridin-4-yl)benzo[d]thiazol-2-amine | 403.1 |
| 97 | 203 | 6-(pyrimidin-5-yl)-N-(4-(pyrrolidin-1-ylmethyl)pyridin-2-yl)benzo[d]thiazol-2-amine | 389.1 |

TABLE 1-continued

| E.g. | Cmpd | Name | [M + H]⁺ |
|---|---|---|---|
| 98 | 204 | N-(4-((4-methylpiperazin-1-yl)methyl)pyridin-2-yl)-6-(pyridin-4-yl)benzo[d]thiazol-2-amine | 417.1 |
| 99 | 205 | 6-(2-methylpyridin-4-yl)-N-(4-(pyrrolidin-1-yl-methyl)pyridin-2-yl)-benzo[d]thiazol-2-amine | 402.1 |
| 100 | 206 | 2-(2-((6-(pyridin-4-yl)-benzo[d]thiazol-2-yl)-amino)pyridin-4-yl)acetic acid | 363.0 |
| 101 | 207 | 1,1-dimethyl-3-((2-((6-(pyridin-4-yl)benzo[d]-thiazol-2-yl)amino)-pyridin-4-yl)methyl)urea | 405.1 |
| 102 | 208 | 6-(3-methoxypyridin-4-yl)-N-(4-(pyrrolidin-1-ylmethyl)pyridin-2-yl)-benzo[d]thiazol-2-amine | 418.1 |
| 103 | 209 | 6-(2-methoxypyridin-4-yl)-N-(4-(pyrrolidin-1-yl-methyl)pyridin-2-yl)benzo-[d]thiazol-2-amine | 418.1 |

TABLE 1-continued

| E.g. | Cmpd | Name | [M + H]⁺ |
|---|---|---|---|
| 104 | 210 | 6-(2-chloropyridin-4-yl)-N-(4-(pyrrolidin-1-ylmethyl)pyridin-2-yl)benzo[d]thiazol-2-amine | 422.0 |
| 105 | 211 | 6-(3-methylpyridin-4-yl)-N-(4-(pyrrolidin-1-yl-methyl)pyridin-2-yl)-benzo[d]thiazol-2-amine | 402.1 |
| 106 | 212 | 2-(2-((6-(pyridin-4-yl)-benzo[d]thiazol-2-yl)-amino)pyridin-4-yl)-N-(2-(pyrrolidin-1-yl)ethyl)-acetamide | 459.1 |
| 107 | 213 | N-(4-((methylamino)-methyl)pyridin-2-yl)-6-(pyridin-4-yl)benzo[d]-thiazol-2-amine | 348.1 |
| 108 | 214 | 3-(2-((4-(pyrrolidin-1-ylmethyl)pyridin-2-yl)amino)benzo[d]-thiazol-6-yl)benzonitrile | 412.1 |
| 109 | 215 | N-(4-morpholinopyridin-2-yl)-6-(pyridin-4-yl)-benzo[d]thiazol-2-amine | 390.1 |

TABLE 1-continued

| E.g. | Cmpd | Name | [M + H]+ |
|---|---|---|---|
| 110 | 216 | N-(4-((3-methoxy-pyrrolidin-1-yl)methyl)-pyridin-2-yl)-6-(pyridin-4-yl)benzo[d]thiazol-2-amine | 418.1 |
| 111 | 217 | N-(4-((4-(methylsulfonyl)-piperazin-1-yl)methyl)-pyridin-2-yl)-6-(pyridin-4-yl)benzo[d]thiazol-2-amine | 481.0 |
| 112 | 218 | 6-(2-methoxypyrimidin-5-yl)-N-(4-(pyrrolidin-1-ylmethyl)pyridin-2-yl)-benzo[d]thiazol-2-amine | 419.1 |
| 113 | 219 | 3-(piperidin-1-yl)-N-((2-((6-(pyridin-4-yl)benzo-[d]thiazol-2-yl)amino)-pyridin-4-yl)methyl)-propanamide | 473.2 |
| 114 | 220 | 6-(benzo[c][1,2,5]oxa-diazol-5-yl)-N-(4-(pyrrolidin-1-ylmethyl)-pyridin-2-yl)benzo[d]-thiazol-2-amine | 429.1 |
| 115 | 221 | 1-methyl-4-(2-((6-(pyridin-4-yl)benzo[d]thiazol-2-yl)amino)pyridin-4-yl)-piperazin-2-one | 417.1 |

TABLE 1-continued

| E.g. | Cmpd | Name | [M + H]⁺ |
|---|---|---|---|
| 116 | 222 | 2-(4-(2-((6-(pyridin-4-yl)-benzo[d]thiazol-2-yl)-amino)pyridin-4-yl)-piperazin-1-yl)ethanol | 433.1 |
| 117 | 223 | N-methyl-4-((2-((6-(pyridin-4-yl)benzo[d]-thiazol-2-yl)amino)-pyridin-4-yl)methyl)-piperazine-1-carboxamide | 460.2 |
| 118 | 224 | Methyl 2-(2-((6-(pyridin-4-yl)benzo[d]thiazol-2-yl)amino)pyridin-4-yl)-acetate | 377.1 |
| 119 | 225 | 2-(methyl(2-((6-(pyridin-4-yl)benzo[d]thiazol-2-yl)amino)pyridin-4-yl)amino)ethanol | 378.1 |
| 120 | 226 | 1-((2-((6-(pyridin-4-yl)-benzo[d]thiazol-2-yl)-amino)pyridin-4-yl)-methyl)pyrrolidin-3-ol | 404.1 |
| 121 | 227 | N-(4-((4-methylpiperazin-1-yl)methyl)pyridin-2-yl)-6-(pyrimidin-5-yl)benzo-[d]thiazol-2-amine | 418.2 |

TABLE 1-continued

| E.g. | Cmpd | Name | [M + H]+ |
|---|---|---|---|
| 123 | 228 | 2-((2-((6-(pyridin-4-yl)-benzo[d]thiazol-2-yl)-amino)pyridin-4-yl)-amino)ethanol | 364.1 |
| 124 | 229 | 7-methyl-6-(pyridin-4-yl)-N-(4-(pyrrolidin-1-ylmethyl)pyridin-2-yl)-benzo[d]thiazol-2-amine | 402.1 |
| 125 | 230 | 5-methyl-6-(pyridin-4-yl)-N-(4-(pyrrolidin-1-yl-methyl)pyridin-2-yl)benzo-[d]thiazol-2-amine | 402.1 |
| 126 | 231 | N-(pyridin-2-yl)-6-(pyridin-4-yl)benzo[d]thiazol-2-amine | 305.0 |
| 127 | 232 | 6-(2-aminopyrimidin-5-yl)-N-(4-(pyrrolidin-1-ylmethyl)pyridin-2-yl)-benzo[d]thiazol-2-amine | 404.1 |
| 128 | 233 | 2-(2-((6-(pyridin-4-yl)-benzo[d]thiazol-2-yl)-amino)pyridin-4-yl)-1-(pyrrolidin-1-yl)ethanone | 416.1 |
| 129 | 234 | N-(4-(pyrrolidin-1-yl-methyl)pyridin-2-yl)-6-(2-(trifluoromethyl)-pyridin-4-yl)benzo[d]-thiazol-2-amine | 456.1 |

TABLE 1-continued

| E.g. | Cmpd | Name | [M + H]⁺ |
|---|---|---|---|
| 130 | 235 | 1-methyl-N-((2-((6-(pyridin-4-yl)benzo[d]-thiazol-2-yl)amino)-pyridin-4-yl)methyl)-pyrrolidine-2-carboxamide | 445.1 |
| 131 | 236 | 5-(pyridin-4-yl)-N-(4-(pyrrolidin-1-ylmethyl)-pyridin-2-yl)thiazolo-[5,4-b]pyridin-2-amine | 389.1 |
| 132 | 237 | 5-(pyrimidin-5-yl)-N-(4-(pyrrolidin-1-ylmethyl)-pyridin-2-yl)thiazolo-[5,4-b]pyridin-2-amine | 390.1 |
| 133 | 238 | N-(4-(aminomethyl)-pyridin-2-yl)-6-(pyrimidin-5-yl)benzo[d]thiazol-2-amine | 335.1 |
| 134 | 239 | N-methyl-2-(2-((6-(pyridin-4-yl)benzo[d]-thiazol-2-yl)amino)pyridin-4-yl)acetamide | 376.1 |
| 135 | 240 | N-(2-hydroxyethyl)-2-(2-((6-(pyridin-4-yl)benzo-[d]thiazol-2-yl)amino)-pyridin-4-yl)acetamide | 406.0 |

TABLE 1-continued

| E.g. | Cmpd | Name | [M + H]+ |
|------|------|------|----------|
| 136 | 242 | N-(4-(pyrrolidin-1-yl-methyl)pyridin-2-yl)-6-(1H-1,2,4-triazol-1-yl)-benzo[d]thiazol-2-amine | 378.1 |
| 137 | 243 | 1-(3-hydroxypyrrolidin-1-yl)-2-(2-((6-(pyridin-4-yl)benzo[d]thiazol-2-yl)amino)pyridin-4-yl)-ethanone | 432.0 |
| 138 | 244 | N-((2-((6-(pyrimidin-5-yl)benzo[d]thiazol-2-yl)amino)pyridin-4-yl)-methyl)methanesulfonamide | 413.0 |
| 139 | 245 | N-(4-morpholinopyridin-2-yl)-6-(4H-1,2,4-triazol-4-yl)benzo[d]thiazol-2-amine | 380.1 |
| 140 | 246 | N-(4-(4-methylpiperazin-1-yl)pyridin-2-yl)-6-(4H-1,2,4-triazol-4-yl)benzo-[d]thiazol-2-amine | 393.2 |

TABLE 1-continued

| E.g. | Cmpd | Name | [M + H]+ |
|---|---|---|---|
| 141 | 247 | N-(4-(piperazin-1-yl)-pyridin-2-yl)-6-(pyridin-4-yl)benzo[d]thiazol-2-amine | 389.1 |
| 142 | 248 | N-(4-(4-methylpiperazin-1-yl)pyridin-2-yl)-5-(1H-pyrazol-4-yl)thiazolo[5,4-b]pyridin-2-amine | 393.0 |
| 143 | 249 | N-(4-(piperazin-1-yl)-pyridin-2-yl)-5-(1H-pyrazol-4-yl)thiazolo-[5,4-b]pyridin-2-amine | 379.1 |
| 144 | 250 | 6-(1H-imidazol-1-yl)-N-(4-(pyrrolidin-1-ylmethyl)-pyridin-2-yl)benzo[d]-thiazol-2-amine | 377.2 |
| 145 | 251 | 6-(5-methyl-1H-pyrazol-4-yl)-N-(4-morpholino-pyridin-2-yl)benzo[d]-thiazol-2-amine | 393.1 |

TABLE 1-continued

| E.g. | Structure | Cmpd | Name | [M + H]+ |
|---|---|---|---|---|
| 146 | 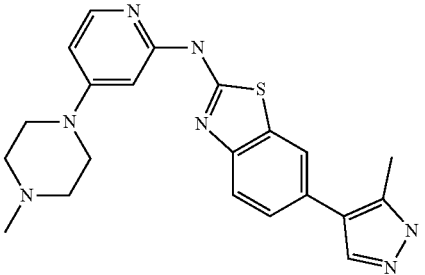 [SMILES: Cc1[nH]ncc1-c1ccc2nc(Nc3cc(N4CCN(C)CC4)ccn3)sc2c1] | 252 | 6-(5-methyl-1H-pyrazol-4-yl)-N-(4-(4-methyl-piperazin-1-yl)pyridin-2-yl)benzo[d]thiazol-2-amine | 406.1 |
| 147 | 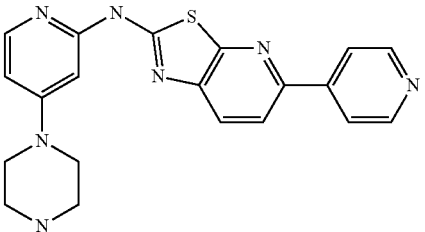 [SMILES: c1cc(-c2ccc3nc(Nc4cc(N5CCNCC5)ccn4)sc3n2)ccn1] | 253 | N-(4-(piperazin-1-yl)-pyridin-2-yl)-5-(pyridin-4-yl)thiazolo[5,4-b]-pyridin-2-amine | 390.1 |
| 148 | 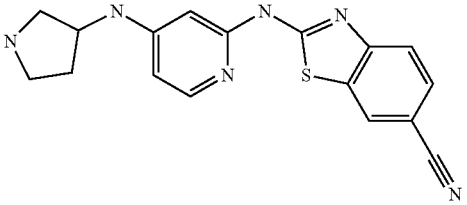 [SMILES: N#Cc1ccc2nc(Nc3cc(NC4CCNC4)ccn3)sc2c1] | 254 | N-(4-(pyrrolidin-3-ylamino)pyridin-2-yl)-6-cyanobenzo[d]thiazol-2-amine | |
| 149 | 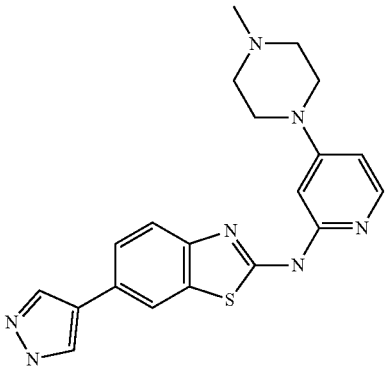 [SMILES: CN1CCN(c2ccnc(Nc3nc4ccc(-c5cn[nH]c5)cc4s3)c2)CC1] | 255 | N-(4-(4-methylpiperazin-1-yl)pyridin-2-yl)-6-(1H-pyrazol-4-yl)benzo[d]-thiazol-2-amine | 392.1 |
| 150 | 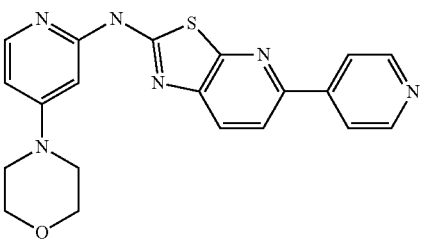 | 256 | N-(4-morpholinopyridin-2-yl)-5-(pyridin-4-yl)-thiazolo[5,4-b]pyridin-2-amine | 391.0 |

TABLE 1-continued

| E.g. | Cmpd | Name | [M + H]+ |
|---|---|---|---|
| 151 | 257 | N-(4-(4-methylpiperazin-1-yl)pyridin-2-yl)-5-(pyridin-4-yl)thiazolo-[5,4-b]pyridin-2-amine | 404.0 |
| 152 | 258 | N-(4-(piperazin-1-yl)-pyridin-2-yl)-6-(1H-pyrazol-4-yl)benzo[d]-thiazol-2-amine | 378.0 |
| 153 | 259 | 6-(pyridazin-4-yl)-N-(4-(pyrrolidin-1-ylmethyl)-pyridin-2-yl)benzo[d]-thiazol-2-amine | 389.0 |
| 154 | 260 | N-(4-((methylamino)-methyl)pyridin-2-yl)-6-(1H-pyrazol-4-yl)benzo-[d]thiazol-2-amine | 337.0 |
| 155 | 261 | N-(4-((dimethylamino)-methyl)pyridin-2-yl)-6-(1H-pyrazol-4-yl)benzo-[d]thiazol-2-amine | 351.1 |
| 156 | 262 | N-(pyrazin-2-yl)-6-(pyridin-4-yl)benzo[d]-thiazol-2-amine | 306.0 |
| 157 | 263 | N-(4-(azetidin-1-ylmethyl)-pyridin-2-yl)-6-(1H-pyrazol-4-yl)benzo[d]-thiazol-2-amine | 363.0 |

TABLE 1-continued

| E.g. | Structure | Cmpd | Name | [M + H]+ |
|---|---|---|---|---|
| 158 | 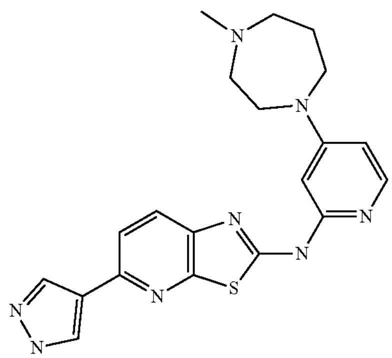 [SMILES: CN1CCCN(c2ccnc(Nc3nc4ccc(-c5cn[nH]c5)nc4s3)c2)CC1] | 264 | N-(4-(4-methyl-1,4-diazepan-1-yl)pyridin-2-yl)-5-(1H-pyrazol-4-yl)thiazolo[5,4-b]pyridin-2-amine | 407.1 |
| 159 | 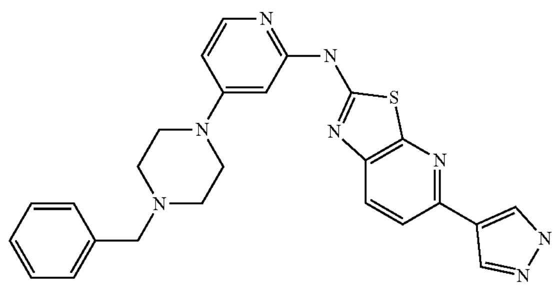 [SMILES: c1ccc(CN2CCN(c3ccnc(Nc4nc5ccc(-c6cn[nH]c6)nc5s4)c3)CC2)cc1] | 265 | N-(4-(4-benzylpiperazin-1-yl)pyridin-2-yl)-5-(1H-pyrazol-4-yl)thiazolo-[5,4-b]pyridin-2-amine | 469.1 |
| 160 | 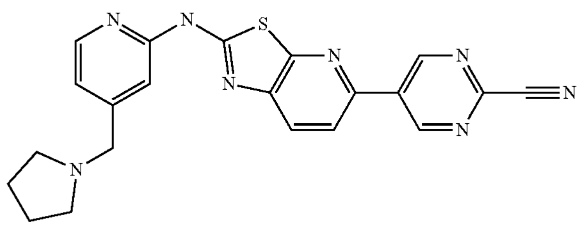 | 266 | 5-(2-((4-(pyrrolidin-1-ylmethyl)pyridin-2-yl)-amino)thiazolo[5,4-b]-pyridin-5-yl)pyrimidine-2-carbonitrile | 415.0 |
| 161 | 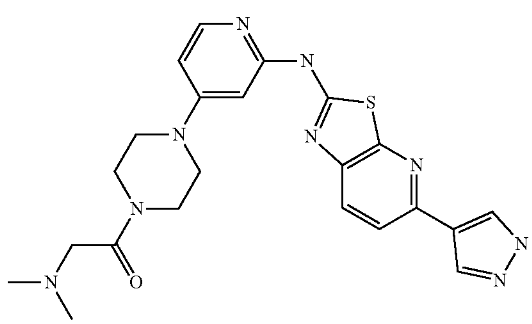 [SMILES: CN(C)CC(=O)N1CCN(c2ccnc(Nc3nc4ccc(-c5cn[nH]c5)nc4s3)c2)CC1] | 267 | 1-(4-(2-((5-(1H-pyrazol-4-yl)thiazolo[5,4-b]-pyridin-2-yl)amino)-pyridin-4-yl)piperazin-1-yl)-2-(dimethylamino)-ethanone | 464.0 |
| 162 | 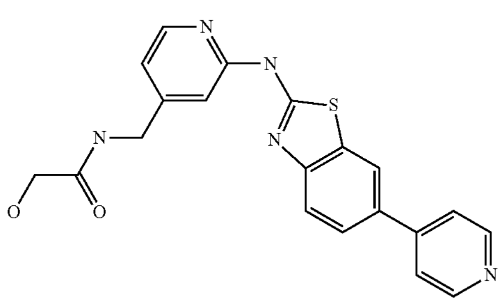 [SMILES: O=C(CO)NCc1ccnc(Nc2nc3ccc(-c4ccncc4)cc3s2)c1] | 268 | 2-hydroxy-N-((2-((6-(pyridin-4-yl)benzo[d]-thiazol-2-yl)amino)-pyridin-4-yl)methyl)-acetamide | 392.0 |

TABLE 1-continued

| E.g. | Structure | Cmpd | Name | [M + H]+ |
|---|---|---|---|---|
| 163 | 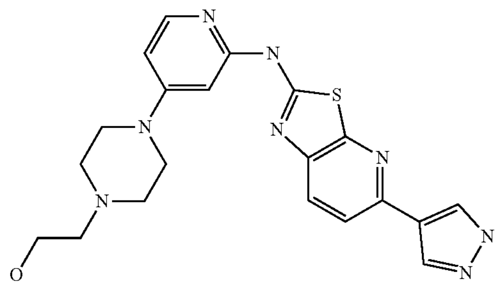 [SMILES: OCCN1CCN(c2ccnc(Nc3nc4ccc(-c5cn[nH]c5)nc4s3)c2)CC1] | 269 | 2-(4-(2-((5-(1H-pyrazol-4-yl)thiazolo[5,4-b]pyridin-2-yl)amino)pyridin-4-yl)-piperazin-1-yl)ethanol | 423.1 |
| 164 | 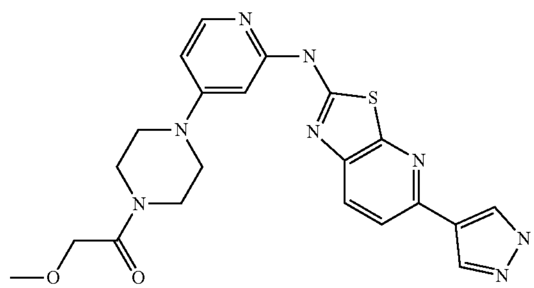 [SMILES: COCC(=O)N1CCN(c2ccnc(Nc3nc4ccc(-c5cn[nH]c5)nc4s3)c2)CC1] | 270 | 1-(4-(2-((5-(1H-pyrazol-4-yl)thiazolo[5,4-b]-pyridin-2-yl)amino)-pyridin-4-yl)piperazin-1-yl)-2-methoxyethanone | 451.1 |
| 165 | 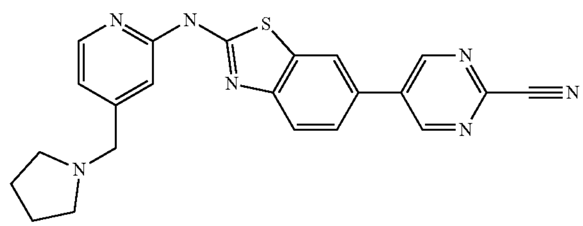 [SMILES: N#Cc1ncc(-c2ccc3nc(Nc4cc(CN5CCCC5)ccn4)sc3c2)cn1] | 271 | 5-(2-((4-(pyrrolidin-1-ylmethyl)pyridin-2-yl)-amino)benzo[d]thiazol-6-yl)pyrimidine-2-carbonitrile | 414.0 |
| 166 | 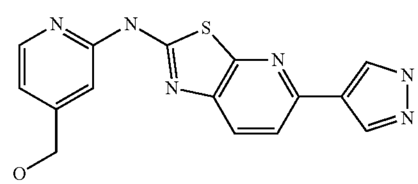 | 272 | (2-((5-(1H-pyrazol-4-yl)thiazolo[5,4-b]-pyridin-2-yl)amino)-pyridin-4-yl)methanol | 325.0 |
| 167 | 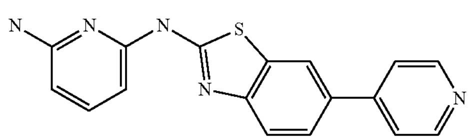 [SMILES: Nc1cccc(Nc2nc3ccc(-c4ccncc4)cc3s2)n1] | 273 | N²-(6-(pyridin-4-yl)-benzo[d]thiazol-2-yl)-pyridine-2,6-diamine | 320.0 |
| 168 | 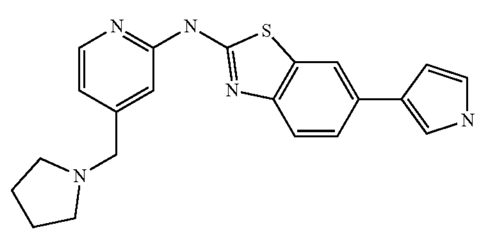 [SMILES: c1cc(CN2CCCC2)cc(Nc2nc3ccc(-c4cc[nH]c4)cc3s2)n1] | 274 | 6-(1H-pyrrol-3-yl)-N-(4-(pyrrolidin-1-ylmethyl)pyridin-2-yl)benzo[d]thiazol-2-amine | 376.1 |

TABLE 1-continued

| E.g. | Structure | Cmpd | Name | [M + H]+ |
|---|---|---|---|---|
| 169 | 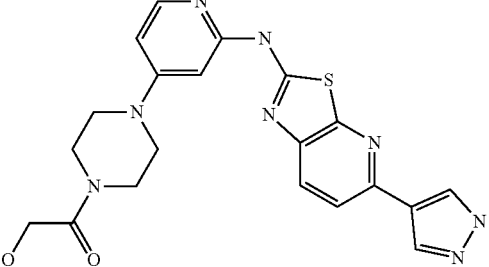 | 275 | 1-(4-(2-((5-(1H-pyrazol-4-yl)thiazolo[5,4-b]-pyridin-2-yl)amino)-pyridin-4-yl)piperazin-1-yl)-2-hydroxyethanone | 437.1 |
| 170 | 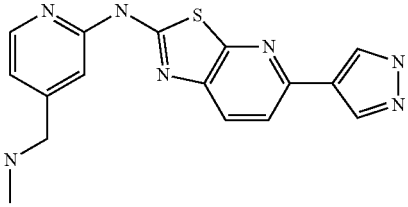 [SMILES: CNCc1ccnc(Nc2nc3ccc(-c4cn[nH]c4)nc3s2)c1] | 276 | N-(4-((methylamino)-methyl)pyridin-2-yl)-5-(1H-pyrazol-4-yl)thiazolo-[5,4-b]pyridin-2-amine | 338.0 |
| 171 | 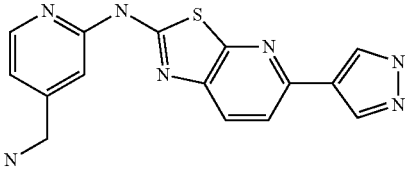 [SMILES: NCc1ccnc(Nc2nc3ccc(-c4cn[nH]c4)nc3s2)c1] | 277 | N-(4-(aminomethyl)-pyridin-2-yl)-5-(1H-pyrazol-4-yl)thiazolo-[5,4-b]pyridin-2-amine | 324.0 |
| 172 | 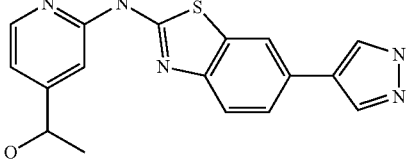 | 278 | 1-(2-((6-(1H-pyrazol-4-yl)benzo[d]thiazol-2-yl)amino)pyridin-4-yl)-ethanol | 338.0 |
| 173 | 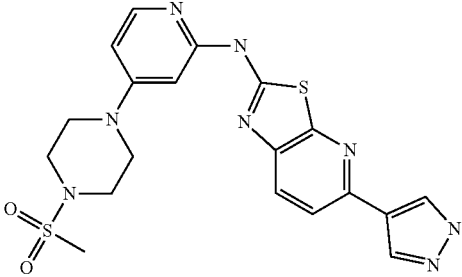 | 279 | N-(4-(4-(methylsulfonyl)-piperazin-1-yl)pyridin-2-yl)-5-(1H-pyrazol-4-yl)-thiazolo[5,4-b]pyridin-2-amine | 457.1 |
| 174 | 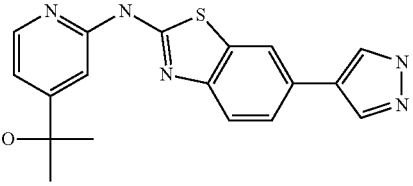 [SMILES: CC(C)(O)c1ccnc(Nc2nc3ccc(-c4cn[nH]c4)cc3s2)c1] | 280 | 2-(2-((6-(1H-pyrazol-4-yl)benzo[d]thiazol-2-yl)amino)pyridin-4-yl)-propan-2-ol | 352.0 |
| 175 | 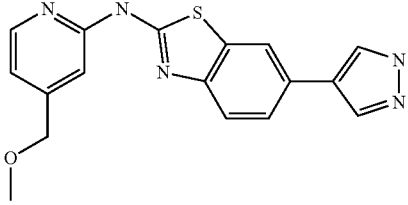 [SMILES: COCc1ccnc(Nc2nc3ccc(-c4cn[nH]c4)cc3s2)c1] | 281 | N-(4-(methoxymethyl)-pyridin-2-yl)-6-(1H-pyrazol-4-yl)benzo[d]-thiazol-2-amine | 338.0 |

TABLE 1-continued

| E.g. | Cmpd | Name | [M + H]+ |
|---|---|---|---|
| 176 | 282 | 1-(4-(2-((5-(1H-pyrazol-4-yl)thiazolo[5,4-b]-pyridin-2-yl)amino)-pyridin-4-yl)piperazin-1-yl)-3-(dimethylamino)-propan-1-one | 478.2 |
| 177 | 283 | (2-((5-(1H-pyrazol-4-yl)-thiazolo[5,4-b]pyridin-2-yl)amino)-3-fluoropyridin-4-yl)methanol | 343.0 |
| 178 | 284 | 1-(4-(2-((5-(1H-pyrazol-4-yl)thiazolo[5,4-b]-pyridin-2-yl)amino)-pyridin-4-yl)piperazin-1-yl)-3-(pyrrolidin-1-yl)-propan-1-one | 504.2 |
| 179 | 285 | N-(4-((dimethylamino)-methyl)pyridin-2-yl)-6-(5-methyl-1H-pyrazol-4-yl)benzo[d]thiazol-2-amine | 365.1 |
| 180 | 286 | 6-(5-methyl-1H-pyrazol-4-yl)-N-(4-((methyl-amino)methyl)pyridin-2-yl)benzo[d]thiazol-2-amine | 351.1 |
| 181 | 287 | N-(4-(aminomethyl)-pyridin-2-yl)-6-(5-methyl-1H-pyrazol-4-yl)benzo[d]thiazol-2-amine | 337.0 |

TABLE 1-continued

| E.g. | Structure | Cmpd | Name | [M + H]⁺ |
|---|---|---|---|---|
| 182 | 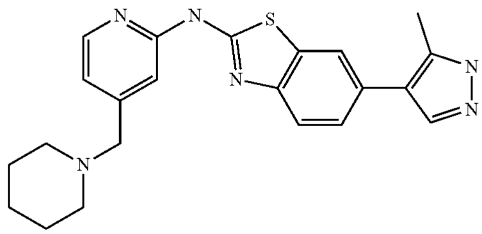 [SMILES: Cc1[nH]ncc1-c1ccc2nc(Nc3cc(CN4CCCCC4)ccn3)sc2c1] | 288 | 6-(5-methyl-1H-pyrazol-4-yl)-N-(4-(piperidin-1-ylmethyl)pyridin-2-yl)-benzo[d]thiazol-2-amine | 405.1 |
| 183 | 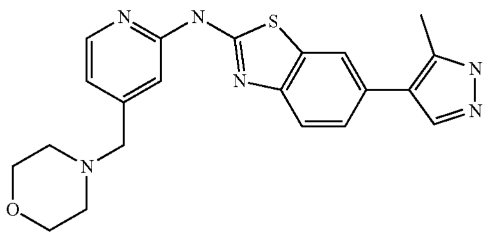 [SMILES: Cc1[nH]ncc1-c1ccc2nc(Nc3cc(CN4CCOCC4)ccn3)sc2c1] | 289 | 6-(5-methyl-1H-pyrazol-4-yl)-N-(4-(morpholino-methyl)pyridin-2-yl)-benzo[d]thiazol-2-amine | 407.2 |
| 184 | 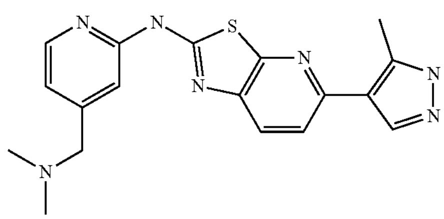 | 290 | N-(4-((dimethylamino)-methyl)pyridin-2-yl)-5-(5-methyl-1H-pyrazol-4-yl)thiazolo[5,4-b]-pyridin-2-amine | 366.1 |
| 185 | 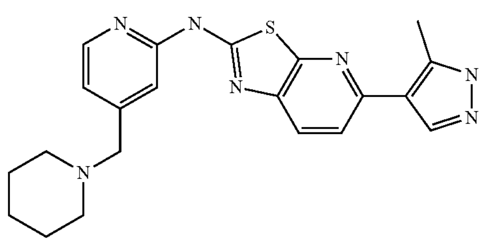 [SMILES: Cc1[nH]ncc1-c1ccc2nc(Nc3cc(CN4CCCCC4)ccn3)sc2n1] | 291 | 5-(5-methyl-1H-pyrazol-4-yl)-N-(4-(piperidin-1-ylmethyl)pyridin-2-yl)thiazolo[5,4-b]pyridin-2-amine | 406.1 |
| 186 | 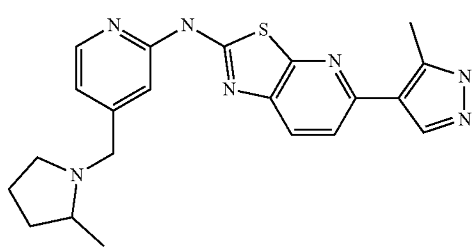 [SMILES: Cc1[nH]ncc1-c1ccc2nc(Nc3cc(CN4CCCC4C)ccn3)sc2n1] | 292 | 5-(5-methyl-1H-pyrazol-4-yl)-N-(4-((2-methyl-pyrrolidin-1-yl)methyl)-pyridin-2-yl)thiazolo-[5,4-b]pyridin-2-amine | 406.1 |
| 187 | 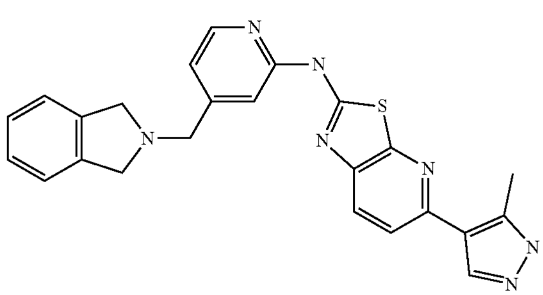 [SMILES: Cc1[nH]ncc1-c1ccc2nc(Nc3cc(CN4Cc5ccccc5C4)ccn3)sc2n1] | 293 | N-(4-(isoindolin-2-yl-methyl)pyridin-2-yl)-5-(5-methyl-1H-pyrazol-4-yl)thiazolo[5,4-b]-pyridin-2-amine | 440.1 |

TABLE 1-continued

| E.g. | Structure | Cmpd | Name | [M + H]+ |
|---|---|---|---|---|
| 188 | 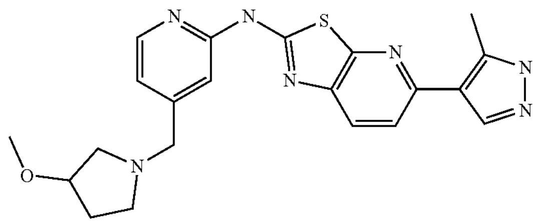 | 294 | N-(4-((3-methoxy-pyrrolidin-1-yl)methyl)-pyridin-2-yl)-5-(5-methyl-1H-pyrazol-4-yl)thiazolo[5,4-b]-pyridin-2-amine | 422.2 |
| 189 | 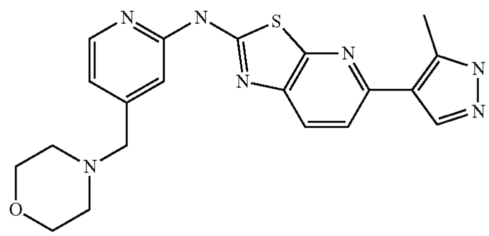 [SMILES: Cc1[nH]ncc1-c1ccc2nc(Nc3cc(CN4CCOCC4)ccn3)sc2n1] | 295 | 5-(5-methyl-1H-pyrazol-4-yl)-N-(4-(morpholino-methyl)pyridin-2-yl)-thiazolo[5,4-b]pyridin-2-amine | 408.1 |
| 190 | 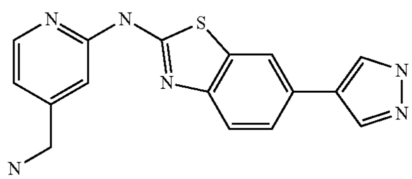 [SMILES: NCc1ccnc(Nc2nc3ccc(-c4cn[nH]c4)cc3s2)c1] | 296 | N-(4-(aminomethyl)-pyridin-2-yl)-6-(1H-pyrazol-4-yl)benzo[d]-thiazol-2-amine | 323.1 |
| 191 | 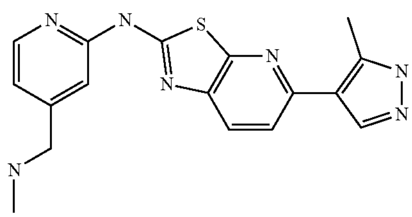 [SMILES: CNCc1ccnc(Nc2nc3ccc(-c4cn[nH]c4C)nc3s2)c1] | 297 | 5-(5-methyl-1H-pyrazol-4-yl)-N-(4-((methyl-amino)methyl)pyridin-2-yl)thiazolo[5,4-b]-pyridin-2-amine | 352.1 |
| 192 | 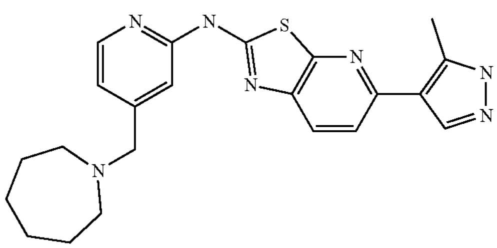 [SMILES: Cc1[nH]ncc1-c1ccc2nc(Nc3cc(CN4CCCCCC4)ccn3)sc2n1] | 298 | N-(4-(azepan-1-ylmethyl)-pyridin-2-yl)-5-(5-methyl-1H-pyrazol-4-yl)thiazolo-[5,4-b]pyridin-2-amine | 420.1 |
| 193 | 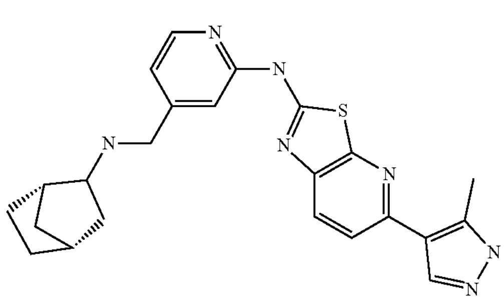 [SMILES: Cc1[nH]ncc1-c1ccc2nc(Nc3cc(CNC4C[C@@H]5CC[C@H]4C5)ccn3)sc2n1] | 299 | N-(4-(((1S,4R)-bicyclo-[2.2.1]heptan-2-ylamino)-methyl)pyridin-2-yl)-5-(5-methyl-1H-pyrazol-4-yl)thiazolo[5,4-b]-pyridin-2-amine | 432.2 |

TABLE 1-continued

| E.g. | Structure | Cmpd | Name | [M + H]⁺ |
|---|---|---|---|---|
| 194 | 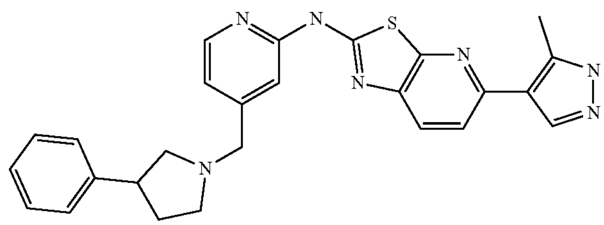 | 300 | 5-(5-methyl-1H-pyrazol-4-yl)-N-(4-((3-phenyl-pyrrolidin-1-yl)methyl)-pyridin-2-yl)thiazolo-[5,4-b]pyridin-2-amine | 468.1 |
| 195 | 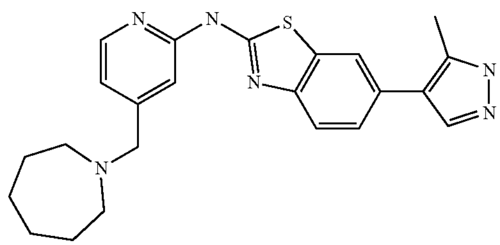 [SMILES: Cc1[nH]ncc1-c1ccc2nc(Nc3cc(CN4CCCCCC4)ccn3)sc2c1] | 301 | N-(4-(azepan-1-ylmethyl)-pyridin-2-yl)-6-(5-methyl-1H-pyrazol-4-yl)benzo[d]-thiazol-2-amine | 419.2 |
| 196 | 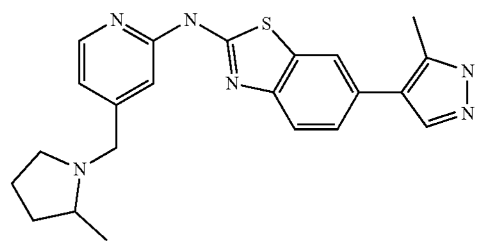 [SMILES: Cc1[nH]ncc1-c1ccc2nc(Nc3cc(CN4CCCC4C)ccn3)sc2c1] | 302 | 6-(5-methyl-1H-pyrazol-4-yl)-N-(4-((2-methyl-pyrrolidin-1-yl)methyl)-pyridin-2-yl)benzo[d]-thiazol-2-amine | 405.2 |
| 197 | 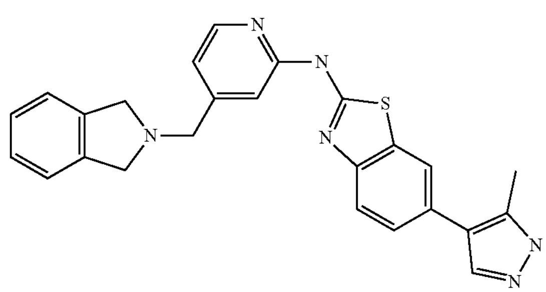 [SMILES: Cc1[nH]ncc1-c1ccc2nc(Nc3cc(CN4Cc5ccccc5C4)ccn3)sc2c1] | 303 | N-(4-(isoindolin-2-yl-methyl)pyridin-2-yl)-6-(5-methyl-1H-pyrazol-4-yl)benzo[d]thiazol-2-amine | 439.1 |
| 198 | 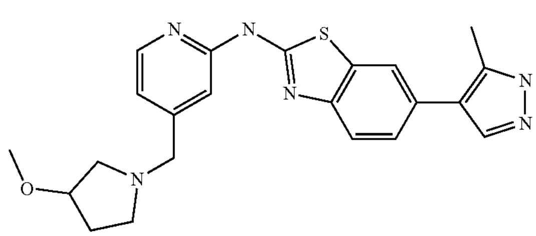 [SMILES: COC1CCN(Cc2ccnc(Nc3nc4ccc(-c5cn[nH]c5C)cc4s3)c2)C1] | 304 | N-(4-((3-methoxy-pyrrolidin-1-yl)methyl)-pyridin-2-yl)-6-(5-methyl-1H-pyrazol-4-yl)benzo[d]thiazol-2-amine | 421.2 |
| 199 | 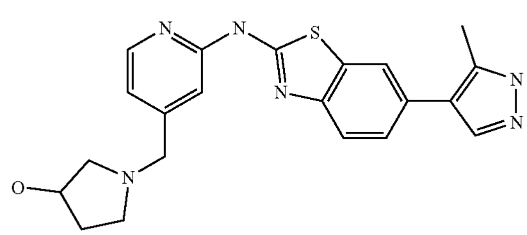 [SMILES: Cc1[nH]ncc1-c1ccc2nc(Nc3cc(CN4CCC(O)C4)ccn3)sc2c1] | 305 | 1-((2-((6-(5-methyl-1H-pyrazol-4-yl)benzo[d]-thiazol-2-yl)amino)-pyridin-4-yl)methyl)-pyrrolidin-3-ol | 407.1 |

TABLE 1-continued

| E.g. | Cmpd | Name | [M + H]+ |
|---|---|---|---|
| 200 | 306 | N-(4-(azetidin-1-yl-methyl)pyridin-2-yl)-5-(5-methyl-1H-pyrazol-4-yl)thiazolo[5,4-b]-pyridin-2-amine | 378.1 |
| 201 | 307 | 1-((2-((5-(5-methyl-1H-pyrazol-4-yl)thiazolo-[5,4-b]pyridin-2-yl)-amino)pyridin-4-yl)-methyl)pyrrolidin-3-ol | 408.1 |
| 202 | 308 | N-(4-(azetidin-1-yl-methyl)pyridin-2-yl)-6-(5-methyl-1H-pyrazol-4-yl)benzo[d]thiazol-2-amine | 377.1 |
| 203 | 309 | 6-(5-methyl-1H-pyrazol-4-yl)-N-(4-((3-phenyl-pyrrolidin-1-yl)methyl)-pyridin-2-yl)benzo[d]-thiazol-2-amine | 467.1 |
| 204 | 310 | N-(4-((4-(2-methoxy-ethyl)piperazin-1-yl)-methyl)pyridin-2-yl)-6-(5-methyl-1H-pyrazol-4-yl)benzo[d]thiazol-2-amine | 464.1 |
| 205 | 311 | N-(4-((4-(2-methoxy-ethyl)piperazin-1-yl)-methyl)pyridin-2-yl)-6-(pyridin-4-yl)benzo[d]-thiazol-2-amine | 461.2 |

TABLE 1-continued

| E.g. | Structure | Cmpd | Name | [M + H]+ |
|---|---|---|---|---|
| 206 | 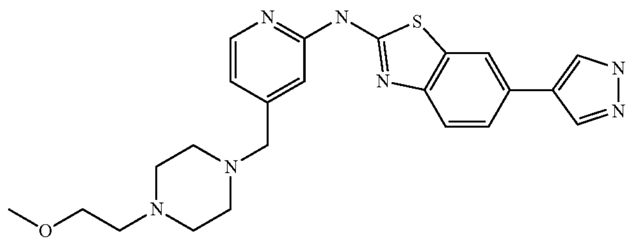 | 312 | N-(4-((4-(2-methoxy-ethyl)piperazin-1-yl)-methyl)pyridin-2-yl)-6-(1H-pyrazol-4-yl)-benzo[d]thiazol-2-amine | 450.2 |
| 207 | 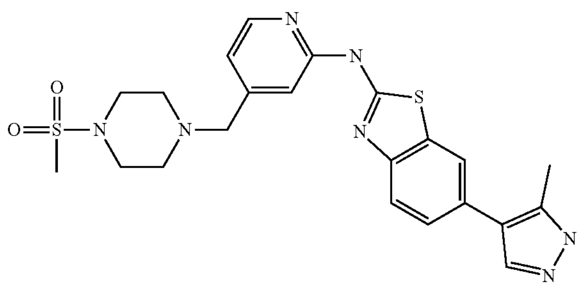 [SMILES: Cc1[nH]ncc1-c1ccc2nc(Nc3cc(CN4CCN(S(C)(=O)=O)CC4)ccn3)sc2c1] | 313 | 6-(5-methyl-1H-pyrazol-4-yl)-N-(4-((4-(methylsulfonyl)-piperazin-1-yl)methyl)-pyridin-2-yl)benzo[d]-thiazol-2-amine | 484.0 |
| 208 | 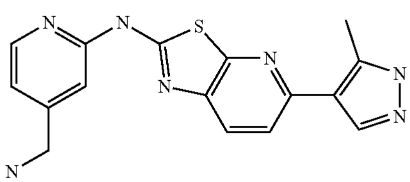 [SMILES: Cc1[nH]ncc1-c1ccc2nc(Nc3cc(CN)ccn3)sc2n1] | 314 | N-(4-(aminomethyl)-pyridin-2-yl)-5-(5-methyl-1H-pyrazol-4-yl)thiazolo[5,4-b]-pyridin-2-amine | 338.1 |
| 209 | 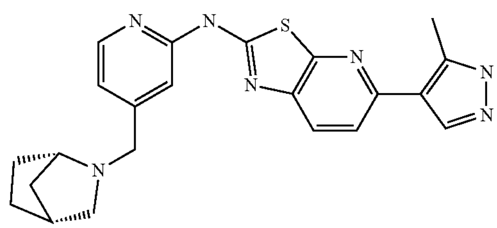 [SMILES: Cc1[nH]ncc1-c1ccc2nc(Nc3cc(CN4C[C@@H]5CC[C@H]4C5)ccn3)sc2n1] | 315 | N-(4-(((1S,4R)-2-azabicyclo[2.2.1]-heptan-2-ylmethyl)-pyridin-2-yl)-5-(5-methyl-1H-pyrazol-4-yl)thiazolo[5,4-b]-pyridin-2-amine | 418.1 |
| 210 | 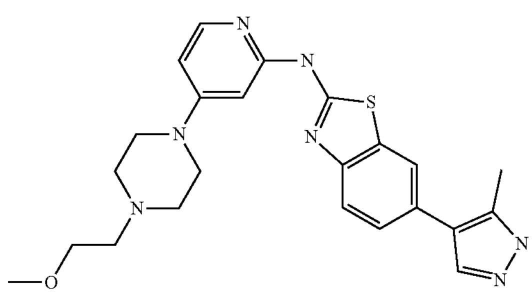 [SMILES: COCCN1CCN(c2ccnc(Nc3nc4ccc(-c5cn[nH]c5C)cc4s3)c2)CC1] | 316 | N-(4-(4-(2-methoxy-ethyl)piperazin-1-yl)pyridin-2-yl)-6-(5-methyl-1H-pyrazol-4-yl)benzo[d]thiazol-2-amine | 450.1 |
| 211 | 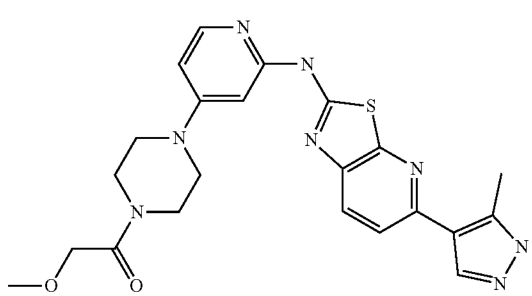 | 317 | 2-methoxy-1-(4-(2-((6-(5-methyl-1H-pyrazol-4-yl)thiazolo[5,4-b]-pyridin-2-yl)amino)-pyridin-4-yl)piperazin-1-yl)ethanone | 465.0 |

TABLE 1-continued

| E.g. | Cmpd | Name | [M + H]+ |
|---|---|---|---|
| 212 | 318 | N-(4-((1S,4R)-2-azabicyclo[2.2.1]heptan-2-ylmethyl)pyridin-2-yl)-6-(5-methyl-1H-pyrazol-4-yl)benzo[d]thiazol-2-amine | |
| 213 | 319 | N-(4-(((1S,4R)-bicyclo-[2.2.1]heptan-2-ylamino)-methyl)pyridin-2-yl)-6-(5-methyl-1H-pyrazol-4-yl)benzo[d]thiazol-2-amine | |
| 214 | 320 | N-(4-(4-(2-methoxy-ethyl)piperazin-1-yl)-pyridin-2-yl)-6-(1H-pyrazol-4-yl)benzo[d]-thiazol-2-amine | 436.1 |
| 215 | 321 | N-(4-((3,3-dimethyl-pyrrolidin-1-yl)methyl)-pyridin-2-yl)-5-(5-methyl-1H-pyrazol-4-yl)thiazolo[5,4-b]pyridin-2-amine | 420.2 |
| 216 | 322 | N-(4-(4-(2-methoxy-ethyl)piperazin-1-yl)pyridin-2-yl)-6-(pyridin-4-yl)benzo[d]-thiazol-2-amine | 447.1 |
| 217 | 323 | 5-(5-methyl-1H-pyrazol-4-yl)-N-(4-(4-(methyl-sulfonyl)piperazin-1-yl)pyridin-2-yl)thiazolo-[5,4-b]pyridin-2-amine | 471.1 |

TABLE 1-continued

| E.g. | Structure | Cmpd | Name | [M + H]+ |
|---|---|---|---|---|
| 218 | 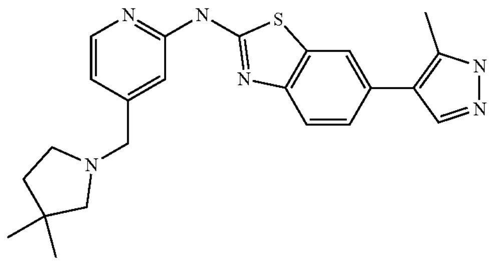 [SMILES: Cc1[nH]ncc1-c1ccc2nc(Nc3cc(CN4CCC(C)(C)C4)ccn3)sc2c1] | 324 | N-(4-((3,3-dimethyl-pyrrolidin-1-yl)methyl)-pyridin-2-yl)-6-(5-methyl-1H-pyrazol-4-yl)benzo[d]thiazol-2-amine | 419.2 |
| 219 | 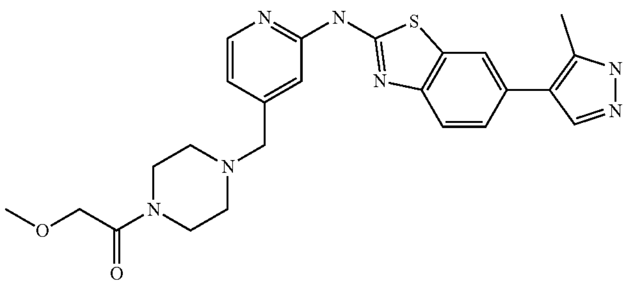 | 325 | 2-methoxy-1-(4-((2-((6-(5-methyl-1H-pyrazol-4-yl)benzo[d]thiazol-2-yl)amino)pyridin-4-yl)methyl)piperazin-1-yl)ethanone | 478.2 |
| 220 | 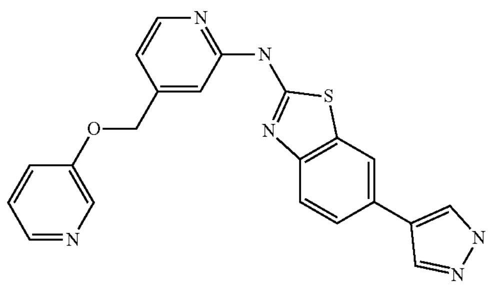 [SMILES: c1cncc(OCc2ccnc(Nc3nc4ccc(-c5cn[nH]c5)cc4s3)c2)c1] | 326 | 6-(1H-pyrazol-4-yl)-N-(4-((pyridin-3-yloxy)-methyl)pyridin-2-yl)-benzo[d]thiazol-2-amine | 401.0 |
| 221 | 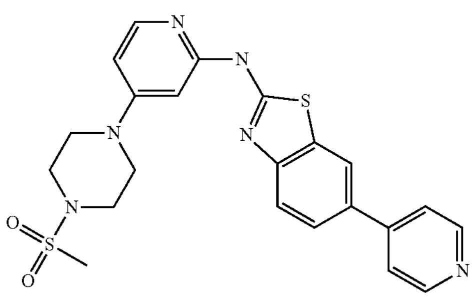 [SMILES: CS(=O)(=O)N1CCN(c2ccnc(Nc3nc4ccc(-c5ccncc5)cc4s3)c2)CC1] | 327 | N-(4-(4-(methylsulfonyl)-piperazin-1-yl)pyridin-2-yl)-6-(pyridin-4-yl)-benzo[d]thiazol-2-amine | 467.1 |
| 222 | 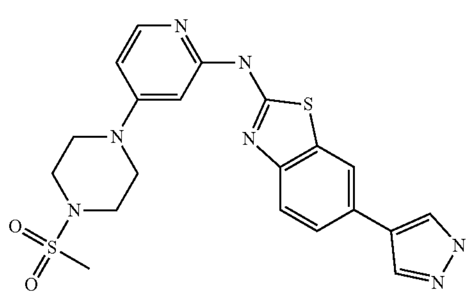 [SMILES: CS(=O)(=O)N1CCN(c2ccnc(Nc3nc4ccc(-c5cn[nH]c5)cc4s3)c2)CC1] | 328 | N-(4-(4-(methylsulfonyl)-piperazin-1-yl)pyridin-2-yl)-6-(1H-pyrazol-4-yl)benzo[d]thiazol-2-amine | 456.1 |

TABLE 1-continued

| E.g. | Cmpd | Name | [M + H]+ |
|---|---|---|---|
| 223 | 329 | N-(4-((4-(methylsulfonyl)-piperazin-1-yl)methyl)-pyridin-2-yl)-6-(1H-pyrazol-4-yl)benzo[d]-thiazol-2-amine | 470.1 |
| 224 | 330 | N-(4-((4-(methylsulfonyl)-piperazin-1-yl)methyl)-pyridin-2-yl)-5-(1H-pyrazol-4-yl)thiazolo-[5,4-b]pyridin-2-amine | 471.1 |
| 225 | 331 | 2-methoxy-1-(4-(2-((6-(5-methyl-1H-pyrazol-4-yl)benzo[d]thiazol-2-yl)amino)pyridin-4-yl)-piperazin-1-yl)ethanone | 464.2 |
| 226 | 332 | 2-methoxy-1-(4-((2-((6-(pyridin-4-yl)benzo[d]-thiazol-2-yl)amino)-pyridin-4-yl)methyl)-piperazin-1-yl)ethanone | 475.2 |
| 227 | 334 | 1-(4-((2-((6-(1H-pyrazol-4-yl)benzo[d]thiazol-2-yl)amino)pyridin-4-yl)methyl)piperazin-1-yl)-2-methoxyethanone | 464.2 |

TABLE 1-continued

| E.g. | Cmpd | Name | [M + H]+ |
|---|---|---|---|
| 228 | 335 | 2-methoxy-1-(4-((2-((5-(5-methyl-1H-pyrazol-4-yl)thiazolo[5,4-b]pyridin-2-yl)amino)pyridin-4-yl)methyl)piperazin-1-yl)ethanone | 479.2 |
| 229 | 336 | 1-(4-((2-((5-(1H-pyrazol-4-yl)thiazolo[5,4-b]pyridin-2-yl)amino)pyridin-4-yl)methyl)piperazin-1-yl)-2-methoxyethanone | 465.2 |
| 230 | 337 | 6-(5-methyl-1H-pyrazol-4-yl)-N-(4-(4-(methylsulfonyl)piperazin-1-yl)pyridin-2-yl)benzo[d]thiazol-2-amine | 470.1 |
| 231 | 338 | 1-(4-(2-((6-(1H-pyrazol-4-yl)benzo[d]thiazol-2-yl)amino)pyridin-4-yl)piperazin-1-yl)-2-methoxyethanone | 450.1 |
| 232 | 339 | 4-(2-((5-(1H-pyrazol-4-yl)thiazolo[5,4-b]pyridin-2-yl)amino)pyridin-4-yl)-1-methylpiperazin-2-one | 407.1 |

TABLE 1-continued

| E.g. | Cmpd | Name | [M + H]⁺ |
|---|---|---|---|
| 233 | 340 | 5-(5-methyl-1H-pyrazol-4-yl)-N-(4-((4-(methylsulfonyl)piperazin-1-yl)methyl)pyridin-2-yl)thiazolo[5,4-b]pyridin-2-amine | 485.1 |
| 234 | 341 | 6-(5-methyl-1H-pyrazol-4-yl)-N-(4-(piperazin-1-yl)pyridin-2-yl)benzo[d]-thiazol-2-amine | |
| 235 | 342 | 1-((2-((6-(1H-pyrazol-4-yl)benzo[d]thiazol-2-yl)amino)pyridin-4-yl)methyl)pyrrolidin-3-ol | 393.1 |
| 236 | 343 | (R)-6-(5-methyl-1H-pyrazol-4-yl)-N-(4-((2-methylpyrrolidin-1-yl)methyl)pyridin-2-yl)benzo[d]thiazol-2-amine | 405.1 |
| 237 | 344 | (R)-5-(5-methyl-1H-pyrazol-4-yl)-N-(4-((2-methylpyrrolidin-1-yl)methyl)pyridin-2-yl)thiazolo[5,4-b]-pyridin-2-amine | 406.1 |
| 238 | 345 | (S)-N-(4-((3-methoxypyrrolidin-1-yl)methyl)-pyridin-2-yl)-6-(5-methyl-1H-pyrazol-4-yl)benzo[d]thiazol-2-amine | 421.1 |

TABLE 1-continued

| E.g. | Cmpd | Name | [M + H]+ |
|---|---|---|---|
| 239 | 346 | (R)-N-(4-((3-methoxy-pyrrolidin-1-yl)methyl)-pyridin-2-yl)-6-(5-methyl-1H-pyrazol-4-yl)benzo[d]thiazol-2-amine | 421.1 |
| 240 | 347 | (S)-N-(4-((3-methoxy-pyrrolidin-1-yl)methyl)-pyridin-2-yl)-5-(5-methyl-1H-pyrazol-4-yl)thiazolo[5,4-b]-pyridin-2-amine | 422.1 |
| 241 | 348 | (R)-N-(4-((2-methyl-pyrrolidin-1-yl)methyl)-pyridin-2-yl)-5-(pyridin-4-yl)thiazolo[5,4-b]-pyridin-2-amine | 403.2 |
| 242 | 349 | N-(4-(isopropoxymethyl)-pyridin-2-yl)-5-(1H-pyrazol-4-yl)thiazolo-[5,4-b]pyridin-2-amine | 367.0 |
| 243 | 350 | (S)-6-(5-methyl-1H-pyrazol-4-yl)-N-(4-((2-methylpyrrolidin-1-yl)methyl)pyridin-2-yl)benzo[d]thiazol-2-amine | 405.1 |
| 244 | 351 | (R)-N-(4-((3-methoxy-pyrrolidin-1-yl)methyl)-pyridin-2-yl)-5-(5-methyl-1H-pyrazol-4-yl)thiazolo-[5,4-b]pyridin-2-amine | 422.1 |
| 245 | 352 | (R)-N-(4-((2-methyl-pyrrolidin-1-yl)methyl)-pyridin-2-yl)-6-(pyridin-4-yl)benzo[d]thiazol-2-amine | 402.1 |

TABLE 1-continued

| E.g. | Cmpd | Name | [M + H]+ |
|---|---|---|---|
| 246 | 353 | (S)-N-(4-((2-methyl-pyrrolidin-1-yl)methyl)-pyridin-2-yl)-5-(pyridin-4-yl)thiazolo[5,4-b]-pyridin-2-amine | 403.1 |
| 247 | 354 | (S)-N-(4-((3-methoxy-pyrrolidin-1-yl)methyl)-pyridin-2-yl)-6-(pyridin-4-yl)benzo[d]thiazol-2-amine | 418.1 |
| 248 | 355 | (R)-N-(4-((3-methoxy-pyrrolidin-1-yl)methyl)-pyridin-2-yl)-6-(pyridin-4-yl)benzo[d]thiazol-2-amine | 418.1 |
| 249 | 356 | N-(4-((cyclopentyloxy)-methyl)pyridin-2-yl)-6-(1H-pyrazol-4-yl)benzo-[d]thiazol-2-amine | 392.1 |
| 250 | 357 | 6-(1H-pyrazol-4-yl)-N-(4-(((tetrahydro-2H-pyran-4-yl)oxy)methyl)-pyridin-2-yl)benzo[d]-thiazol-2-amine | 408.1 |
| 251 | 358 | (S)-5-(5-methyl-1H-pyrazol-4-yl)-N-(4-((2-methylpyrrolidin-1-yl)methyl)pyridin-2-yl)thiazolo[5,4-b]-pyridin-2-amine | 406.1 |

TABLE 1-continued

| E.g. | Structure | Cmpd | Name | [M + H]⁺ |
|---|---|---|---|---|
| 252 | 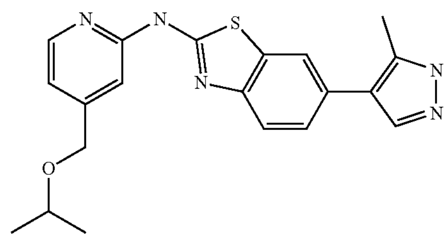 | 359 | N-(4-(isopropoxymethyl)-pyridin-2-yl)-6-(5-methyl-1H-pyrazol-4-yl)benzo-[d]thiazol-2-amine | 380.1 |
| 253 | 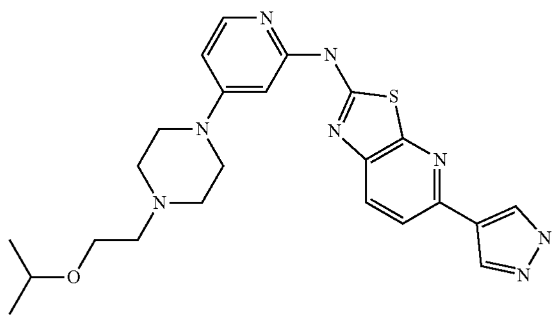 [SMILES: CC(C)OCCN1CCN(c2ccnc(Nc3nc4ccc(-c5cn[nH]c5)nc4s3)c2)CC1] | 360 | N-(4-(4-(2-isopropoxy-ethyl)piperazin-1-yl)-pyridin-2-yl)-5-(1H-pyrazol-4-yl)thiazolo-[5,4-b]pyridin-2-amine | 465.2 |
| 254 | 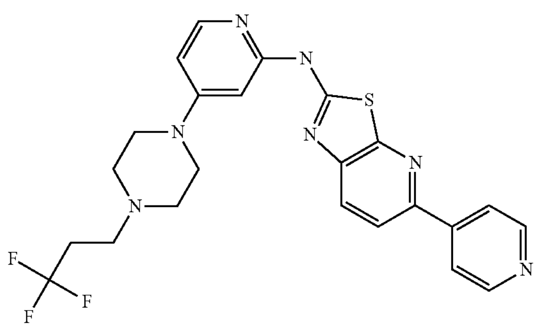 [SMILES: FC(F)(F)CCN1CCN(c2ccnc(Nc3nc4ccc(-c5ccncc5)nc4s3)c2)CC1] | 361 | 5-(pyridin-4-yl)-N-(4-(4-(3,3,3-trifluoropropyl)-piperazin-1-yl)pyridin-2-yl)thiazolo[5,4-b]-pyridin-2-amine | 486.2 |
| 255 | 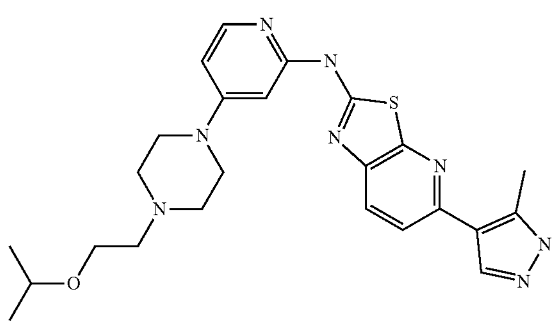 | 362 | N-(4-(4-(2-isopropoxy-ethyl)piperazin-1-yl)pyridin-2-yl)-5-(5-methyl-1H-pyrazol-4-yl)thiazolo[5,4-b]-pyridin-2-amine | 479.2 |
| 256 | 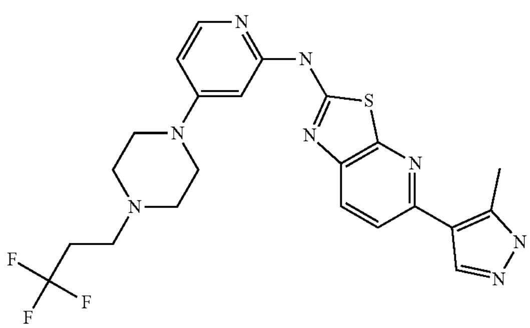 [SMILES: Cc1[nH]ncc1-c1ccc2nc(Nc3cc(N4CCN(CCC(F)(F)F)CC4)ccn3)sc2n1] | 363 | 5-(5-methyl-1H-pyrazol-4-yl)-N-(4-(4-(3,3,3-trifluoropropyl)piperazin-1-yl)pyridin-2-yl)thiazolo-[5,4-b]pyridin-2-amine | 489.0 |

TABLE 1-continued

| E.g. | Cmpd | Name | [M + H]+ |
|---|---|---|---|
| 257 | 364 | N-(4-(4-(2-isopropoxy-ethyl)piperazin-1-yl)-pyridin-2-yl)-5-(pyridin-4-yl)thiazolo[5,4-b]-pyridin-2-amine | 476.2 |
| 258 | 365 | N-(4-(4-(1-methoxy-propan-2-yl)piperazin-1-yl)pyridin-2-yl)-5-(5-methyl-1H-pyrazol-4-yl)thiazolo[5,4-b]pyridin-2-amine | 465.1 |
| 259 | 366 | 6-(5-methyl-1H-pyrazol-4-yl)-N-(4-(4-(3,3,3-trifluoropropyl)piperazin-1-yl)pyridin-2-yl)benzo-[d]thiazol-2-amine | 488.1 |
| 260 | 367 | (S)-N-(4-(3-methyl-4-(methylsulfonyl)piperazin-1-yl)pyridin-2-yl)-5-(pyridin-4-yl)thiazolo-[5,4-b]pyridin-2-amine | 482.1 |
| 261 | 368 | N-(4-(4-(2-isopropoxy-ethyl)piperazin-1-yl)-pyridin-2-yl)-6-(1H-pyrazol-4-yl)benzo[d]-thiazol-2-amine | 464.1 |

TABLE 1-continued

| E.g. | Cmpd | Name | [M + H]+ |
|---|---|---|---|
| 262 | 369 | N-(4-(4-(isopropyl-sulfonyl)piperazin-1-yl)pyridin-2-yl)-5-(5-methyl-1H-pyrazol-4-yl)thiazolo[5,4-b]-pyridin-2-amine | 499.2 |
| 263 | 370 | 2,2-dimethyl-1-(4-(2-((5-(5-methyl-1H-pyrazol-4-yl)thiazolo-[5,4-b]pyridin-2-yl)-amino)pyridin-4-yl)-piperazin-1-yl)propan-1-one | 477.1 |
| 264 | 371 | N-(4-(4-(2-isopropoxy-ethyl)piperazin-1-yl)-pyridin-2-yl)-6-(pyridin-4-yl)benzo[d]thiazol-2-amine | 475.2 |
| 265 | 372 | 6-(pyridin-4-yl)-N-(4-(4-(3,3,3-trifluoropropyl)-piperazin-1-yl)pyridin-2-yl)benzo[d]thiazol-2-amine | 485.1 |
| 266 | 373 | (S)-2-methoxy-1-(2-methyl-4-(2-((5-(5-methyl-1H-pyrazol-4-yl)thiazolo[5,4-b]pyridin-2-yl)amino)pyridin-4-yl)piperazin-1-yl)-ethanone | 479.2 |

TABLE 1-continued

| E.g. | Cmpd | Name | [M + H]+ |
|---|---|---|---|
| 267 | 374 | (S)-2-methoxy-1-(2-methyl-4-(2-((5-(pyridin-4-yl)thiazolo-[5,4-b]pyridin-2-yl)-amino)pyridin-4-yl)-piperazin-1-yl)ethanone | 476.1 |
| 268 | 375 | (S)-5-(5-methyl-1H-pyrazol-4-yl)-N-(4-(3-methyl-4-(methyl-sulfonyl)piperazin-1-yl)pyridin-2-yl)thiazolo-[5,4-b]pyridin-2-amine | 485 |
| 269 | 376 | (R)-N-(4-(4-(2-methoxyethyl)-3-methylpiperazin-1-yl)-pyridin-2-yl)-5-(5-methyl-1H-pyrazol-4-yl)thiazolo[5,4-b]-pyridin-2-amine | 465.1 |
| 270 | 377 | 6-(1H-pyrazol-4-yl)-N-(4-(4-(3,3,3-trifluoro-propyl)piperazin-1-yl)-pyridin-2-yl)benzo[d]-thiazol-2-amine | 474.1 |
| 271 | 378 | N-(4-(4-(2-isopropoxy-ethyl)piperazin-1-yl)-pyridin-2-yl)-6-(5-methyl-1H-pyrazol-4-yl)benzo[d]thiazol-2-amine | 478.2 |

TABLE 1-continued

| E.g. | Cmpd | Name | [M + H]+ |
|---|---|---|---|
| 272 | 379 | (R)-2-methoxy-1-(3-methyl-4-(2-((5-(5-methyl-1H-pyrazol-4-yl)thiazolo[5,4-b]-pyridin-2-yl)amino)-pyridin-4-yl)piperazin-1-yl)ethanone | 479.2 |
| 273 | 380 | (R)-N-(4-(2-methyl-4-(methylsulfonyl)piperazin-1-yl)pyridin-2-yl)-5-(pyridin-4-yl)thiazolo-[5,4-b]pyridin-2-amine | 482.1 |
| 274 | 381 | (S)-N-(4-(4-(2-methoxy-ethyl)-3-methylpiperazin-1-yl)pyridin-2-yl)-5-(5-methyl-1H-pyrazol-4-yl)thiazolo[5,4-b]pyridin-2-amine | 465.2 |
| 275 | 382 | (S)-N-(4-(4-(2-methoxy-ethyl)-3-methylpiperazin-1-yl)pyridin-2-yl)-5-(pyridin-4-yl)thiazolo-[5,4-b]pyridin-2-amine | 462.1 |
| 276 | 383 | (R)-N-(4-(4-(2-methoxy-ethyl)-3-methylpiperazin-1-yl)pyridin-2-yl)-5-(pyridin-4-yl)thiazolo-[5,4-b]pyridin-2-amine | 462.1 |

TABLE 1-continued

| E.g. | Cmpd | Name | [M + H]+ |
|---|---|---|---|
| 277 | 384 | 1-(4-(2-((5-(1H-pyrazol-4-yl)thiazolo[5,4-b]pyridin-2-yl)amino)-pyridin-4-yl)piperazin-1-yl)-2-isopropoxy-ethanone | 479.1 |
| 278 | 385 | 2-isopropoxy-1-(4-(2-((5-(5-methyl-1H-pyrazol-4-yl)thiazolo[5,4-b]pyridin-2-yl)amino)-pyridin-4-yl)piperazin-1-yl)ethanone | 493.1 |
| 279 | 386 | 2-isopropoxy-1-(4-(2-((5-(pyridin-4-yl)-thiazolo[5,4-b]pyridin-2-yl)amino)pyridin-4-yl)piperazin-1-yl)-ethanone | 490.1 |
| 280 | 387 | (R)-2-methoxy-1-(3-methyl-4-(2-((5-(pyridin-4-yl)thiazolo[5,4-b]-pyridin-2-yl)amino)-pyridin-4-yl)piperazin-1-yl)ethanone | 476.1 |
| 281 | 388 | (R)-5-(5-methyl-1H-pyrazol-4-yl)-N-(4-(2-methyl-4-(methyl-sulfonyl)piperazin-1-yl)pyridin-2-yl)thiazolo-[5,4-b]pyridin-2-amine | 485.1 |

TABLE 1-continued

| E.g. | Structure | Cmpd | Name | [M + H]+ |
|---|---|---|---|---|
| 282 | 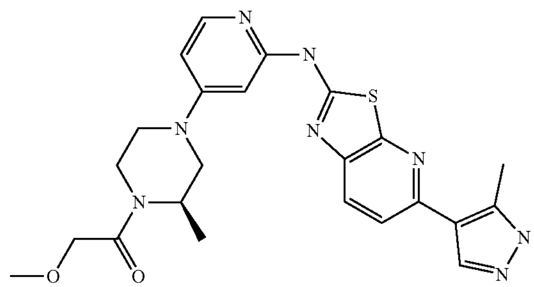 [SMILES: COCC(=O)N1CCN(c2ccnc(Nc3nc4ccc(-c5cn[nH]c5C)nc4s3)c2)C[C@H]1C] | 389 | (R)-2-methoxy-1-(2-methyl-4-(2-((5-(5-methyl-1H-pyrazol-4-yl)thiazolo[5,4-b]pyridin-2-yl)amino)-pyridin-4-yl)piperazin-1-yl)ethanone | 479.2 |
| 283 | 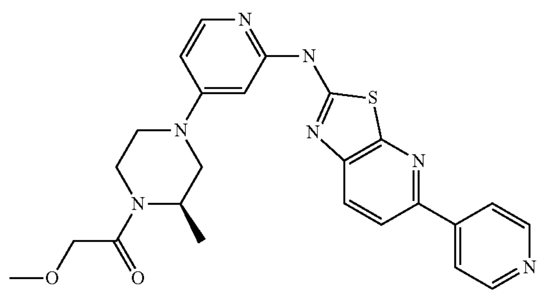 [SMILES: COCC(=O)N1CCN(c2ccnc(Nc3nc4ccc(-c5ccncc5)nc4s3)c2)C[C@H]1C] | 390 | (R)-2-methoxy-1-(2-methyl-4-(2-((5-(pyridin-4-yl)thiazolo-[5,4-b]pyridin-2-yl)-amino)pyridin-4-yl)-piperazin-1-yl)ethanone | 476.1 |
| 284 | 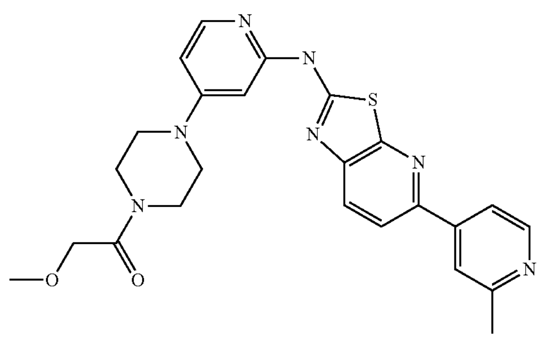 [SMILES: COCC(=O)N1CCN(c2ccnc(Nc3nc4ccc(-c5ccnc(C)c5)nc4s3)c2)CC1] | 391 | 2-methoxy-1-(4-(2-((5-(2-methylpyridin-4-yl)-thiazolo[5,4-b]pyridin-2-yl)amino)pyridin-4-yl)piperazin-1-yl)-ethanone | 476.1 |
| 285 | 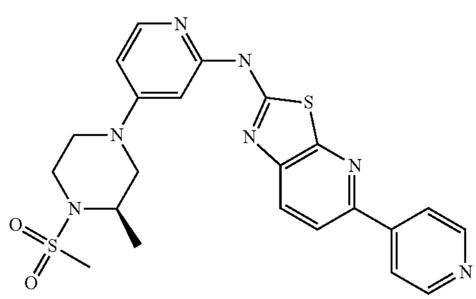 [SMILES: C[C@@H]1CN(c2ccnc(Nc3nc4ccc(-c5ccncc5)nc4s3)c2)CCN1S(C)(=O)=O] | 392 | (R)-N-(4-(3-methyl-4-(methylsulfonyl)piperazin-1-yl)pyridin-2-yl)-5-(pyridin-4-yl)thiazolo-[5,4-b]pyridin-2-amine | 482.0 |
| 286 | 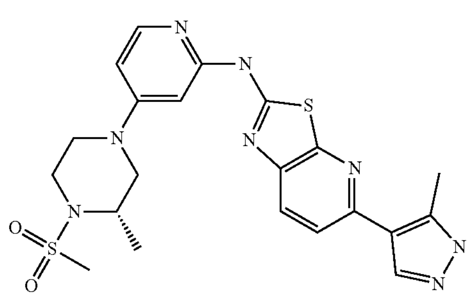 [SMILES: Cc1[nH]ncc1-c1ccc2nc(Nc3cc(N4CCN(S(C)(=O)=O)[C@@H](C)C4)ccn3)sc2n1] | 393 | (S)-5-(5-methyl-1H-pyrazol-4-yl)-N-(4-(3-methyl-4-(methyl-sulfonyl)piperazin-1-yl)pyridin-2-yl)thiazolo-[5,4-b]pyridin-2-amine | 485.1 |

TABLE 1-continued

| E.g. | Cmpd | Name | [M + H]⁺ |
|---|---|---|---|
| 287 | 394 | N-(4-(4-(2-methoxy-ethyl)piperazin-1-yl)-pyridin-2-yl)-5-(2-methylpyridin-4-yl)-thiazolo[5,4-b]pyridin-2-amine | 462.1 |
| 288 | 395 | 5-(2-methylpyridin-4-yl)-N-(4-(4-(methyl-sulfonyl)piperazin-1-yl)pyridin-2-yl)thiazolo-[5,4-b]pyridin-2-amine | 482.0 |
| 289 | 396 | 2-methoxy-1-(4-(2-((5-(pyridazin-4-yl)thiazolo-[5,4-b]pyridin-2-yl)-amino)pyridin-4-yl)-piperazin-1-yl)ethanone | 463.0 |
| 290 | 397 | N-(4-(4-(methylsulfonyl)-piperazin-1-yl)pyridin-2-yl)-5-(pyridazin-4-yl)-thiazolo[5,4-b]pyridin-2-amine | 469.1 |

US 11,773,110 B2

133                                                                 134

TABLE 1-continued

| E.g. | Structure | Cmpd | Name | [M + H]⁺ |
|---|---|---|---|---|
| 291 | 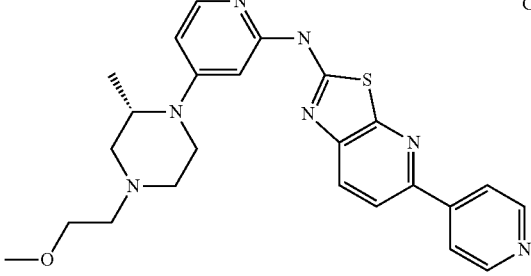 Chiral | 398 | (S)-N-(4-(4-(2-methoxy-ethyl)-2-methylpiperazin-1-yl)pyridin-2-yl)-5-(pyridin-4-yl)thiazolo-[5,4-b]pyridin-2-amine | 462.1 |
| 292 | 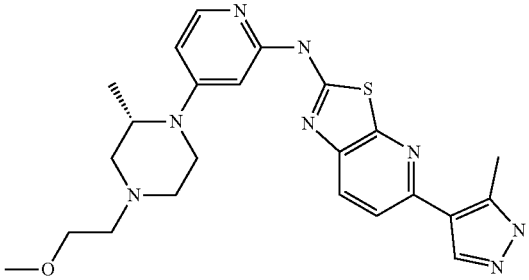 [SMILES: COCCN1CCN(c2ccnc(Nc3nc4ccc(-c5cn[nH]c5C)nc4s3)c2)[C@@H](C)C1] | 399 | (S)-N-(4-(4-(2-methoxy-ethyl)-2-methylpiperazin-1-yl)pyridin-2-yl)-5-(5-methyl-1H-pyrazol-4-yl)thiazolo[5,4-b]pyridin-2-amine | 465.1 |
| 293 | 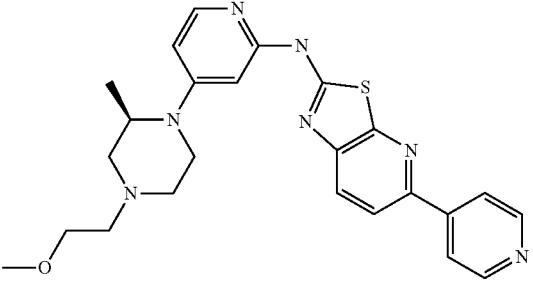 [SMILES: COCCN1CCN(c2ccnc(Nc3nc4ccc(-c5ccncc5)nc4s3)c2)[C@H](C)C1] | 400 | (R)-N-(4-(4-(2-methoxy-ethyl)-2-methylpiperazin-1-yl)pyridin-2-yl)-5-(pyridin-4-yl)thiazolo-[5,4-b]pyridin-2-amine | 462.1 |
| 294 | 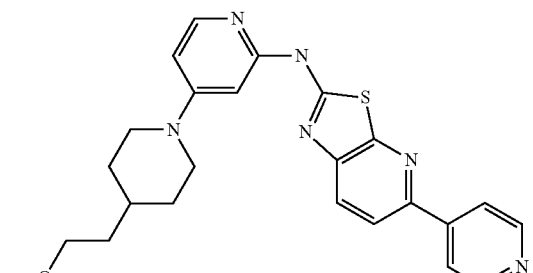 | 401 | N-(4-(4-(2-methoxy-ethyl)piperidin-1-yl)-pyridin-2-yl)-5-(pyridin-4-yl)thiazolo[5,4-b]-pyridin-2-amine | 447.1 |
| 295 | 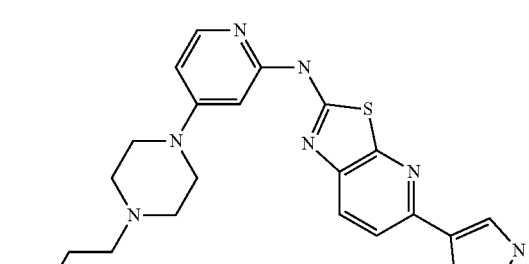 | 402 | N-(4-(4-(2-methoxy-ethyl)piperidin-1-yl)-pyridin-2-yl)-5-(1H-pyrazol-4-yl)thiazolo-[5,4-b]pyridin-2-amine | 436.1 |

TABLE 1-continued

| E.g. | Cmpd | Name | [M + H]+ |
|---|---|---|---|
| 296 | 403 | N4-(2-methoxyethyl)-N4-methyl-N2-5-(pyridin-4-yl)thiazolo[5,4-b]pyridin-2-yl)pyridine-2,4-diamine | 393.1 |
| 297 | 404 | N-(4-((1S,4S)-5-(2-methoxyethyl)-2,5-diazabicyclo[2.2.1]-heptan-2-yl)pyridin-2-yl)-5-(5-methyl-1H-pyrazol-4-yl)thiazolo-[5,4-b]pyridin-2-amine | 463.1 |
| 298 | 405 | 5-(5-methyl-1H-pyrazol-4-yl)-N-(4-(4-(pyridin-2-yl)piperazin-1-yl)pyridin-2-yl)thiazolo[5,4-b]-pyridin-2-amine | 470.2 |
| 299 | 406 | N-(4-(4-(2-methoxy-ethyl)piperazin-1-yl)-pyridin-2-yl)-5-(pyrimidin-5-yl)thiazolo-[5,4-b]pyridin-2-amine | 449.1 |
| 300 | 407 | N-(4-(4-(2-methoxy-ethyl)piperidin-1-yl)-pyridin-2-yl)-5-(5-methyl-1H-pyrazol-4-yl)thiazolo[5,4-b]-pyridin-2-amine | 450.1 |

TABLE 1-continued

| E.g. | Cmpd | Name | [M + H]+ |
|---|---|---|---|
| 301 | 408 | N4-(2-methoxyethyl)-N4-methyl-N2-(5-5-methyl-1H-pyrazol-4-yl)thiazolo[5,4-b]pyridin-2-yl)-pyridine-2,4-diamine | 396.1 |
| 302 | 409 | N2-(5-(1H-pyrazol-4-yl)-thiazolo[5,4-b]pyridin-2-yl)-N4-(2-methoxyethyl)-N4-methylpyridine-2,4-diamine | 382.0 |
| 303 | 410 | (R)-N-(4-(4-(2-methoxyethyl)-2-methylpiperazin-1-yl)pyridin-2-yl)-5-(5-methyl-1H-pyrazol-4-yl)thiazolo[5,4-b]pyridin-2-amine | 465.2 |
| 304 | 411 | (S)-N-(4-(2-methyl-4-(methylsulfonyl)piperazin-1-yl)pyridin-2-yl)-5-(pyridin-4-yl)thiazolo[5,4-b]pyridin-2-amine | 482.0 |
| 305 | 412 | (S)-5-(5-methyl-1H-pyrazol-4-yl)-N-(4-(2-methyl-4-(methylsulfonyl)piperazin-1-yl)pyridin-2-yl)thiazolo[5,4-b]pyridin-2-amine | 485.1 |
| 306 | 413 | 2-((4-morpholinopyridin-2-yl)amino)benzo[d]thiazole-6-carbonitrile | 337.9 |

TABLE 1-continued

| E.g. | Cmpd | Name | [M + H]+ |
|---|---|---|---|
| 307 | 414 | 2-((4-(pyrrolidine-1-carbonyl)pyridin-2-yl)amino)benzo[d]-thiazole-6-carbonitrile | 349.9 |
| 308 | 415 | (2-((5-bromothiazolo-[5,4-b]pyridin-2-yl)-amino)pyridin-4-yl)-(pyrrolidin-1-yl)-methanone | 403.78 |
| 309 | 416 | N-(4-(cyclopentyloxy)-pyridin-2-yl)-5-(pyridin-4-yl)thiazolo[5,4-b]-pyridin-2-amine | 390.0 |
| 310 | 417 | N-(4-(cyclopentyloxy)-pyridin-2-yl)-5-(5-methyl-1H-pyrazol-4-yl)thiazolo-[5,4-b]-pyridin-2-amine | 393.1 |
| 311 | 418 | 5-ethynyl-N-(4-(pyrrolidin-1-ylmethyl)-pyridin-2-yl)thiazolo-[5,4-b]pyridin-2-amine | 336.0 |

TABLE 1-continued

| E.g. | Structure | Cmpd | Name | [M + H]+ |
|---|---|---|---|---|
| 312 | 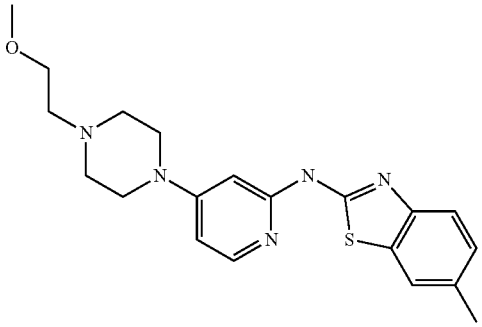 [SMILES: COCCN1CCN(c2ccnc(Nc3nc4ccc(C)cc4s3)c2)CC1] | 419 | N-(4-(4-(2-methoxy-ethyl)piperazin-1-yl)-pyridin-2-yl)-6-methyl-benzo[d]thiazol-2-amine | 384.02 |
| 313 | 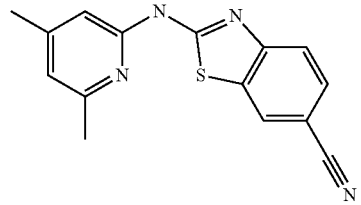 [SMILES: Cc1cc(C)nc(Nc2nc3ccc(C#N)cc3s2)c1] | 420 | 2-((4,6-dimethylpyridin-2-yl)amino)benzo[d]-thiazole-6-carbonitrile | 281.02 |
| 314 | 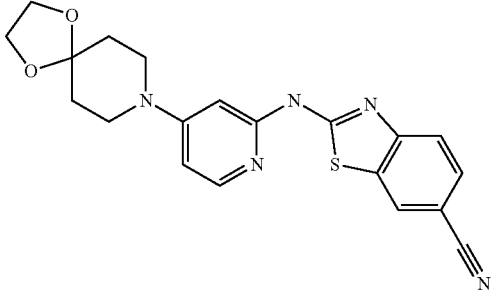 [SMILES: N#Cc1ccc2nc(Nc3cc(N4CCC5(CC4)OCCO5)ccn3)sc2c1] | 421 | 2-((4-(1,4-dioxa-8-azaspiro[4.5]decan-8-yl)pyridin-2-yl)amino)-benzo[d]thiazole-6-carbonitrile | 394.0 |
| 315 | 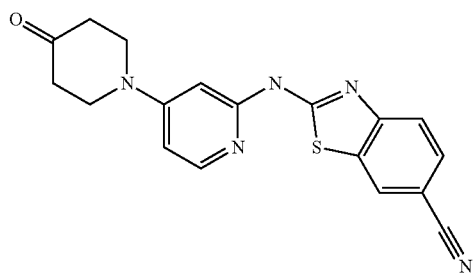 [SMILES: N#Cc1ccc2nc(Nc3cc(N4CCC(=O)CC4)ccn3)sc2c1] | 422 | 2-((4-(4-oxopiperidin-1-yl)pyridin-2-yl)-amino)benzo[d]thiazole-6-carbonitrile | 349.97 |
| 316 | 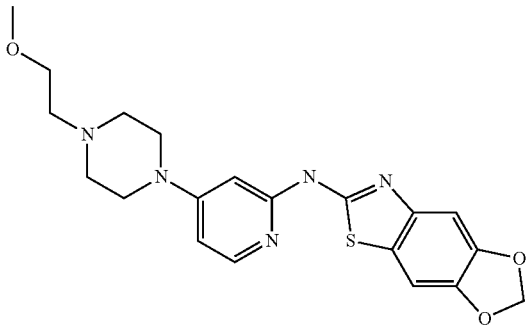 [SMILES: COCCN1CCN(c2ccnc(Nc3nc4cc5c(cc4s3)OCO5)c2)CC1] | 423 | N-(4-(4-(2-methoxyethyl)-piperazin-1-yl)pyridin-2-yl)[1,3]dioxolo[4',5':4,5]-benzo[1,2-d]thiazol-6-amine | 415.92 |

TABLE 1-continued

| E.g. | Structure | Cmpd | Name | [M + H]+ |
|---|---|---|---|---|
| 317 | 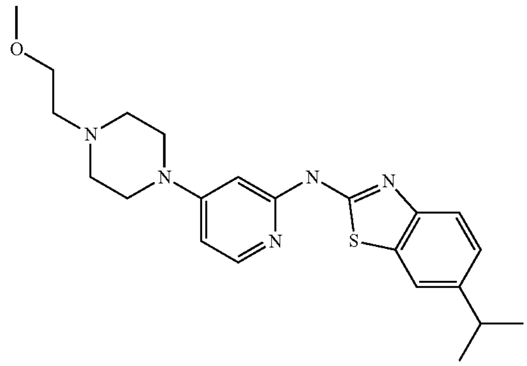 [SMILES: COCCN1CCN(c2ccnc(Nc3nc4ccc(C(C)C)cc4s3)c2)CC1] | 424 | 6-isopropyl-N-(4-(4-(2-methoxyethyl)piperazin-1-yl)pyridin-2-yl)benzo[d]-thiazol-2-amine | 412.01 |
| 318 | 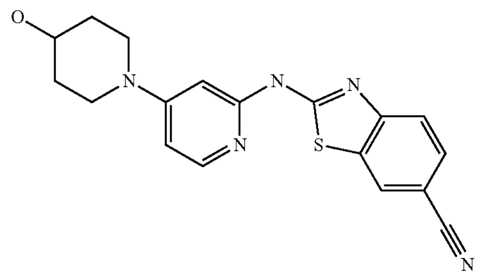 [SMILES: N#Cc1ccc2nc(Nc3cc(N4CCC(O)CC4)ccn3)sc2c1] | 425 | 2-((4-(4-hydroxy-piperidin-1-yl)pyridin-2-yl)amino)benzo[d]-thiazole-6-carbonitrile | 351.92 |
| 319 | 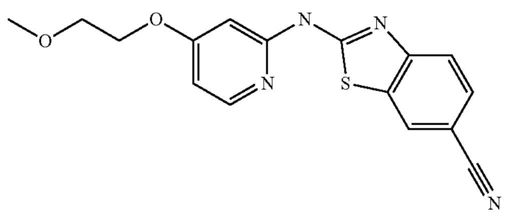 [SMILES: COCCOc1ccnc(Nc2nc3ccc(C#N)cc3s2)c1] | 426 | 2-((4-(2-methoxyethoxy)-pyridin-2-yl)amino)benzo-[d]thiazole-6-carbonitrile | 326.91 |
| 320 | 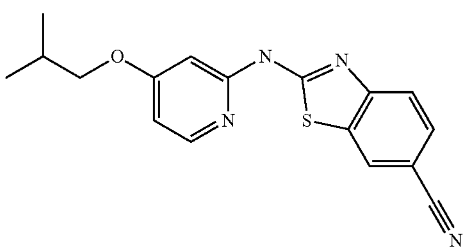 [SMILES: CC(C)COc1ccnc(Nc2nc3ccc(C#N)cc3s2)c1] | 427 | 2-((4-isobutoxypyridin-2-yl)amino)benzo[d]-thiazole-6-carbonitrile | 324.96 |
| 321 | 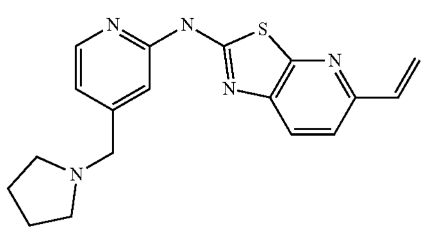 [SMILES: C=Cc1ccc2nc(Nc3cc(CN4CCCC4)ccn3)sc2n1] | 428 | N-(4-(pyrrolidin-1-ylmethyl)pyridin-2-yl)-5-vinylthiazolo[5,4-b]-pyridin-2-amine | |
| 322 | 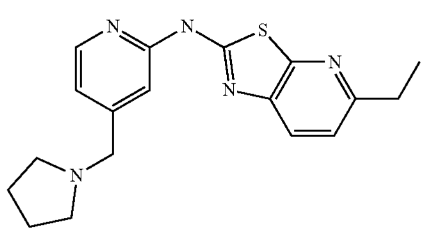 [SMILES: CCc1ccc2nc(Nc3cc(CN4CCCC4)ccn3)sc2n1] | 429 | 5-ethyl-N-(4-(pyrrolidin-1-ylmethyl)pyridin-2-yl)thiazolo[5,4-b]pyridin-2-amine | |

TABLE 1-continued

| E.g. | Cmpd | Name | [M + H]+ |
|---|---|---|---|
| 323 | 430 | 5-(pyridin-4-yl)-N-(4-((tetrahydro-2H-pyran-4-yl)oxy)pyridin-2-yl)-thiazolo[5,4-b]pyridin-2-amine | 406.1 |
| 324 | 431 | N-(4-ethylpyridin-2-yl)-6-(1H-imidazol-4-yl)-benzo[d]thiazol-2-amine | 321.92 |
| 325 | 432 | 1-(4-(2-((5-ethynyl-thiazolo[5,4-b]pyridin-2-yl)amino)pyridin-4-yl)piperazin-1-yl)-2-methoxyethanone | 409.0 |
| 326 | 433 | 4-(2-((5-(pyridin-4-yl)-thiazolo[5,4-b]pyridin-2-yl)amino)pyridin-4-yl)morpholin-3-one | 405.1 |
| 327 | 434 | 2-((4-ethylpyridin-2-yl)amino)benzo[d]-thiazole-6-carbonitrile | 280.95 |
| 328 | 435 | 1,1-dimethyl-3-(2-((5-(pyridin-4-yl)thiazolo-[5,4-b]pyridin-2-yl)-amino)pyridin-4-yl)urea | 392.1 |
| 329 | 436 | 5-(5-methyl-1H-pyrazol-4-yl)-N-(4-(4-(tetrahydro-2H-pyran-4-yl)piperazin-1-yl)pyridin-2-yl)thiazolo-[5,4-b]pyridin-2-amine | 477.1 |

TABLE 1-continued

| E.g. | Structure | Cmpd | Name | [M + H]+ |
|---|---|---|---|---|
| 330 | 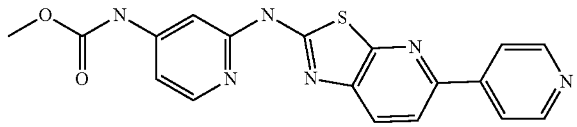 [SMILES: COC(=O)Nc1ccnc(Nc2nc3ccc(-c4ccncc4)nc3s2)c1] | 437 | Methyl (2-((5-(pyridin-4-yl)thiazolo[5,4-b]pyridin-2-yl)amino)pyridin-4-yl)carbamate | 379.1 |
| 331 | 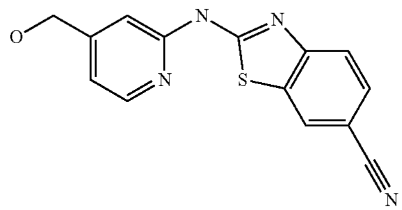 [SMILES: N#Cc1ccc2nc(Nc3cc(CO)ccn3)sc2c1] | 438 | 2-((4-(hydroxymethyl)-pyridin-2-yl)amino)-benzo[d]thiazole-6-carbonitrile | 283.0 |
| 332 | 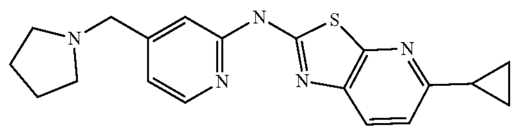 [SMILES: c1cc(CN2CCCC2)cc(Nc2nc3ccc(C4CC4)nc3s2)n1] | 439 | 5-cyclopropyl-N-(4-(pyrrolidin-1-ylmethyl)-pyridin-2-yl)thiazolo-[5,4-b]pyridin-2-amine | 352.1 |

Example 333

Synthesis of N-(4-ethylpyridin-2-yl)-6-(oxazol-5-yl) benzo[d]thiazol-2-amine (Compound 501, Structure 4 in Scheme II, $R^1$=ethyl, $R^4$=5-oxazolyl)

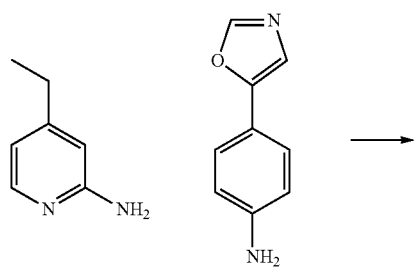

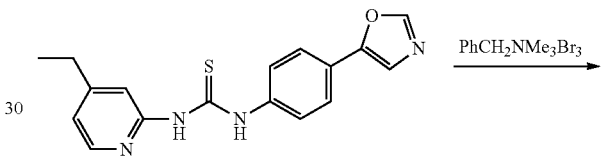

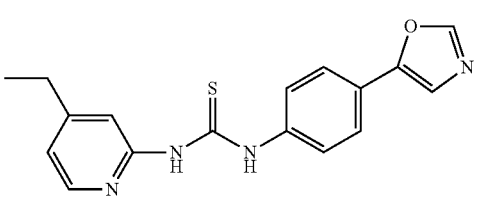

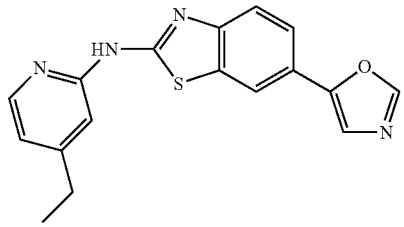

501

A mixture of 4-ethylpyridin-2-amine (100 mg, 0.821 mmol) and bis(1-benzotriazolyl)methanethione (250 mg, 0.891 mmol) were dissolved in 5 mL of anhydrous N,N-dimethylacetamide. The solution was stirred at room temperature for 1 hour. 4-(Oxazol-5-yl)aniline (130 mg, 0.821 mmol) was the added and the solution stirred at 50° C. for an additional hour. Water (15 mL) was then added and the resulting precipitate collected by vacuum filtration and dried under vacuum. The resulting tan powder was used without further purification. MS calculated for $C_{17}H_{16}N_4OS$: 325.1045; [M+H]+, found: 324.89.

1-(4-Ethylpyridin-2-yl)-3-(4-(oxazol-5-yl)phenyl)thiourea (0.27 g, 0.8 mmol) was dissolved in 5 mL of acetic acid. Benzyltrimethylammonium tribromide (320 mg, 0.821 mmol) was then added directly. The mixture was stirred at 50° C. for 1 hour. The mixture was cooled to 0° C. and diluted with 15 mL of water. The resulting solution was then made basic through addition of solid KOH pellets. The resulting precipitate was collected by vacuum filtration, washed with water and dried under vacuum to afford the crude product as a tan solid. A portion of the solid was purified by rp-HPLC affording 0.6 mg of N-(4-ethylpyridin-2-yl)-6-(oxazol-5-yl)benzo[d]thiazol-2-amine 501 as a yellow solid. MS calculated for $C_{17}H_{14}N_4OS$: 323.0888; [M+H]+, found: 322.93. $^1$H-NMR (400 MHz, MeOD) 8.25-8.23 (m, 2H), 8.17 (s, 1H), 7.75 (d, J=8.4, 1H), 7.66 (d, J=8.4, 1H) 7.50 (s, 1H), 6.97 (s, 1H), 6.88 (d, J=8.4, 1H), 2.68 (q, J=7.7, 2H), 1.28 (t, J=7.7, 3H).

Example 334

Synthesis of 6-(1H-pyrazol-4-yl)-N-(4-(pyrrolidin-1-ylmethyl)pyridin-2-yl)imidazo[1,2-a]pyridin-2-amine (Compound 493, structure 10 in Scheme III, R¹=CH₂—N-pyrrolidinyl, R⁴=4-pyrazolyl)

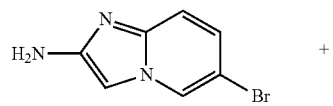

+

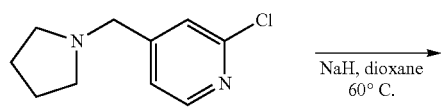

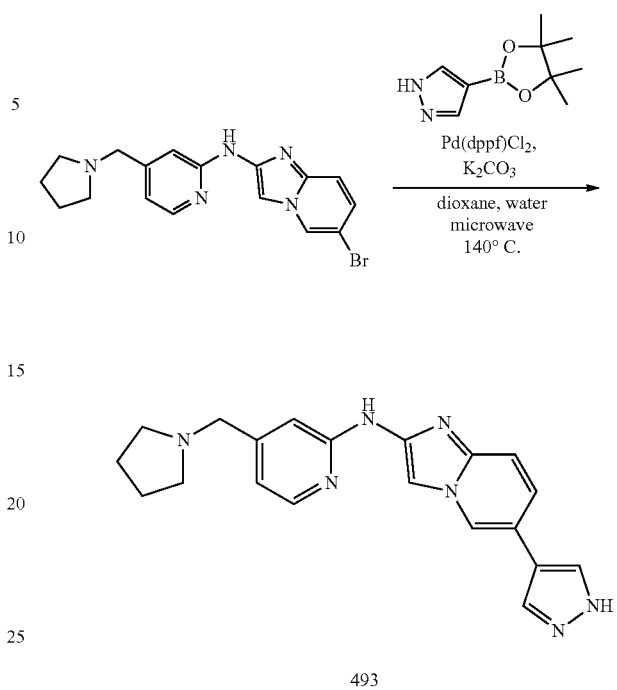

To a solution of 6-bromoimidazo[1,2-a]pyridin-2-amine (200 mg; 0.94 mmol) in dry THF (4 mL) was added NaH (90 mg; 3.76 mmol) in portions at 0° C. The reaction mixture was stirred at r.t. for half an hour. Then 2-chloro-4-(pyrrolidin-1-ylmethyl)pyridine (222 mg, 1.1 mmol) was added. The mixture was heated to 120° C. for 24 hrs. The mixture was quenched by addition of H₂O (20 mL) slowly at 0° C., extracted with DCM (30 mL×3). The combined organic phases were concentrated under reduced pressure and purified by column chromatography on silica (DCM:MeOH=15:1) to obtain 6-bromo-N-(4-(pyrrolidin-1-ylmethyl)pyridin-2-yl)imidazo[1,2-a]pyridin-2-amine (110 mg, yield 80%) as a brown solid.

To a solution of 6-bromo-N-(4-(pyrrolidin-1-ylmethyl)pyridin-2-yl)imidazo[1,2-a]pyridin-2-amine (50 mg, 0.13 mmol) in mixed dioxane/H₂O (2 mL/0.5 mL) was added the pinacol boronate ester (59.2 mg, 0.2 mmol), K₂CO₃ (55.6 mg, 0.4 mmol) and Pd(dppf)Cl₂ (10.8 mg, 0.013 mmol) under nitrogen atmosphere. The mixture reacted under microwave condition at 140° C. for 2 hrs. After cooling, the solvent was removed under reduced pressure, and the residue was purified by prep-TLC to afford 6-(1H-pyrazol-4-yl)-N-(4-(pyrrolidin-1-ylmethyl)pyridin-2-yl)imidazo[1,2-a]pyridin-2-amine 493 (8.5 mg, yield 17.7%). ¹H NMR (400 MHz MeOD) δ 8.93 (s, 1H), 8.47-8.45 (d, J=5.2, 1H), 8.12 (s, 2H), 8.06-8.03 (dd, J=9.2, 1H), 7.85-7.82 (dd, J=9.6, 1H), 7.14-7.11 (m, 2H), 4.43 (s, 2H), 3.55-3.30 (m, 4H), 2.14 (s, 4H).

Examples 335-352

Compounds 484-502 were prepared in a similar fashion as described in Examples 333-334 and their structures, names, and found molecular mass ion numbers are summarized in Table 2 (Example: E.g.; Compound: Cmpd).

TABLE 2

| E.g. | Structure | Cmpd | Name | [M + H]⁺ |
|---|---|---|---|---|
| 335 | 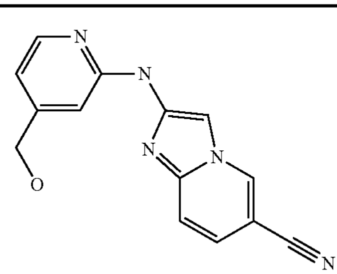 | 484 | 2-((4-(hydoxymethyl)pyridin-2-yl)amino)imidazo[1,2-a]pyridine-6-carbonitrile | |

TABLE 2-continued

| E.g. | Cmpd | Name | [M + H]+ |
|---|---|---|---|
| 336 | 485 | (S)-tert-butyl 3-(2-((6-cyanoimidazo[1,2-a]pyridin-2-yl)amino)isonicotinamido)pyrrolidine-1-carboxylate | 448.2 |
| 337 | 486 | (S)-2-((6-cyanoimidazo[1,2-a]pyridin-2-yl)amino)-N-(pyrrolidin-3-yl)isonicotinamide | 348.2 |
| 338 | 487 | 2-((4-(pyrrolidin-1-ylmethyl)pyridin-2-yl)amino)imidazo[1,2-a]pyridine-6-carbonitrile | 319.2 |
| 339 | 488 | 6-(pyridin-3-yl)-N-(4-(pyrrolidin-1-ylmethyl)pyridin-2-yl)imidazo[1,2-a]pyridin-2-amine | 371.1 |
| 340 | 489 | 1-(4-((2-((6-(pyridin-4-yl)imidazo[1,2-a]pyridin-2-yl)amino)pyridin-4-yl)methyl)piperazin-1-yl)ethanone | 428.1 |

TABLE 2-continued

| E.g. | Structure | Cmpd | Name | [M + H]+ |
|---|---|---|---|---|
| 341 | 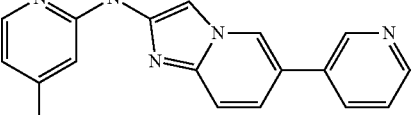 | 490 | 1-(4-((2-((6-(pyridin-3-yl)imidazo[1,2-a]pyridin-2-yl)amino)pyridin-4-yl)methyl)piperazin-1-yl)ethanone | 428.1 |
| 342 | 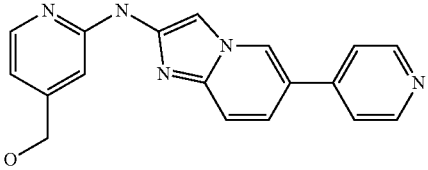 [SMILES: OCc1ccnc(Nc2cn3cc(-c4ccncc4)ccc3n2)c1] | 491 | (2-((6-(pyridin-4-yl)imidazo[1,2-a]pyridin-2-yl)amino)pyridin-4-yl)methanol | 318.1 |
| 343 | 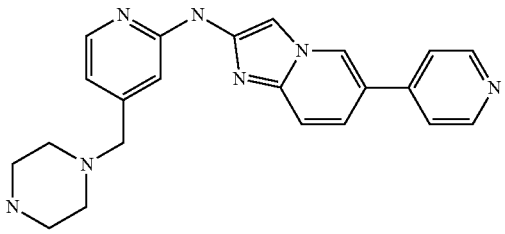 [SMILES: c1cc(-c2ccc3nc(Nc4cc(CN5CCNCC5)ccn4)cn3c2)ccn1] | 492 | N-(4-(piperazin-1-ylmethyl)pyridin-2-yl)-6-(pyridin-4-yl)imidazo[1,2-a]pyridin-2-amine | 386.1 |
| 345 | 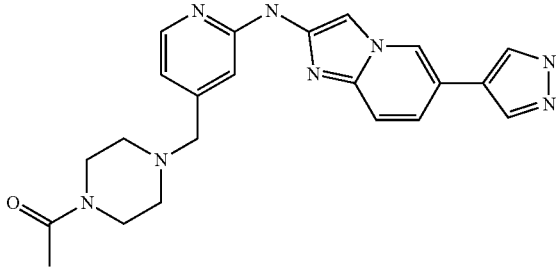 [SMILES: CC(=O)N1CCN(Cc2ccnc(Nc3cn4cc(-c5cn[nH]c5)ccc4n3)c2)CC1] | 494 | 1-(4-((2-((6-(1H-pyrazol-4-yl)imidazo[1,2-a]pyridin-2-yl)amino)pyridin-4-yl)methyl)piperazin-1-yl)ethanone | 417.7 |
| 346 | 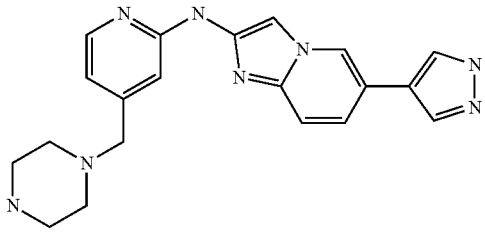 [SMILES: c1cc(CN2CCNCC2)cc(Nc2cn3cc(-c4cn[nH]c4)ccc3n2)n1] | 495 | N-(4-(piperazin-1-ylmethyl)pyridin-2-yl)-6-(1H-pyrazol-4-yl)imidazo[1,2-a]pyridin-2-amine | 375.1 |
| 347 | 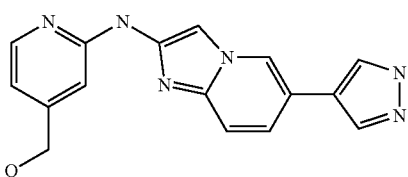 [SMILES: OCc1ccnc(Nc2cn3cc(-c4cn[nH]c4)ccc3n2)c1] | 496 | (2-((6-(1H-pyrazol-4-yl)imidazo[1,2-a]pyridin-2-yl)amino)pyridin-4-yl)methanol | 307.1 |

TABLE 2-continued

| E.g. | Structure | Cmpd | Name | [M + H]+ |
|---|---|---|---|---|
| 348 | 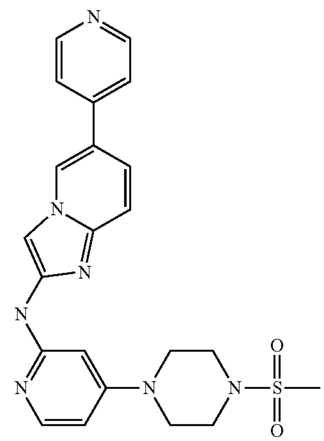 [SMILES: CS(=O)(=O)N1CCN(c2ccnc(Nc3cn4cc(-c5ccncc5)ccc4n3)c2)CC1] | 497 | N-(4-(4-(methylsulfonyl)piperazin-1-yl)pyridin-2-yl)-6-(pyridin-4-yl)imidazo[1,2-a]pyridin-2-amine | 450.1 |
| 349 | 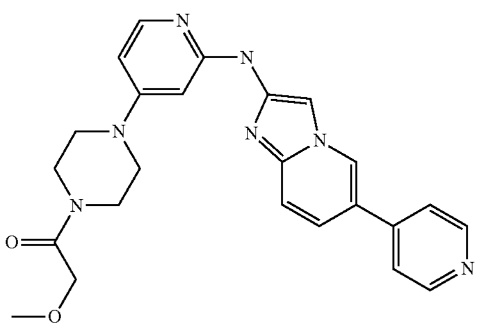 [SMILES: COCC(=O)N1CCN(c2ccnc(Nc3cn4cc(-c5ccncc5)ccc4n3)c2)CC1] | 498 | 2-methoxy-1-(4-(2-((6-(pyridin-4-yl)imidazo[1,2-a]pyridin-2-yl)amino)pyridin-4-yl)piperazin-1-yl)ethanone | 444.2 |
| 350 | 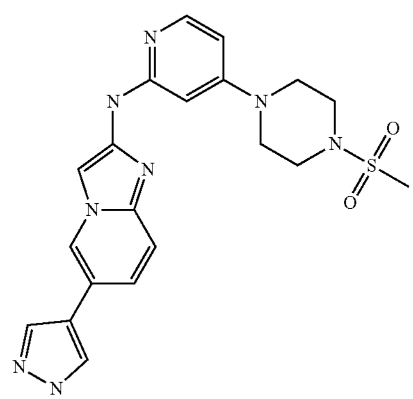 [SMILES: CS(=O)(=O)N1CCN(c2ccnc(Nc3cn4cc(-c5cn[nH]c5)ccc4n3)c2)CC1] | 499 | N-(4-(4-(methylsulfonyl)piperazin-1-yl)pyridin-2-yl)-6-(1H-pyrazol-4-yl)imidazo[1,2-a]pyridin-2-amine | 439.1 |
| 351 | 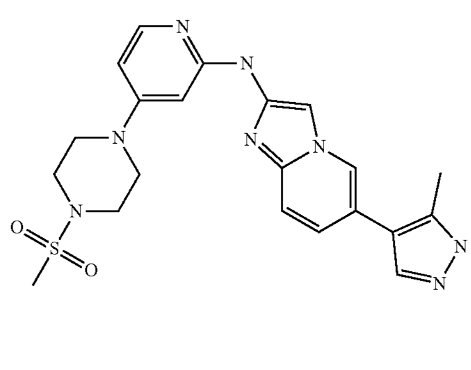 [SMILES: Cc1[nH]ncc1-c1ccc2nc(Nc3cc(N4CCN(S(C)(=O)=O)CC4)ccn3)cn2c1] | 500 | 6-(5-methyl-1H-pyrazol-4-yl)-N-(4-(4-(methylsulfonyl)piperazin-1-yl)pyridin-2-yl)imidazo[1,2-a]pyridin-2-amine | 453.1 |

TABLE 2-continued

| E.g. | Structure | Cmpd | Name | [M + H]+ |
|---|---|---|---|---|
| 352 | 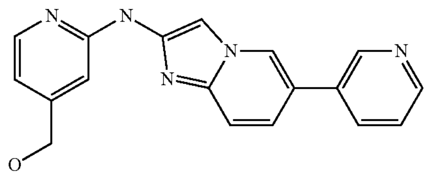 [SMILES: OCc1ccnc(Nc2cn3cc(-c4cccnc4)ccc3n2)c1] | 502 | (2-((6-(pyridin-3-yl)imidazo[1,2-a]pyridin-2-yl)amino)pyridin-4-yl)methanol | 318.0 |

Examples 353-430

Compounds 503-580 were prepared in a similar fashion as described in Examples 1-2 and 333-334, and their structures and names are summarized in Table 3 (Example: E.g.; Compound: Cmpd).

TABLE 3

| E.g. | Structure | Cmpd | Name |
|---|---|---|---|
| 353 | 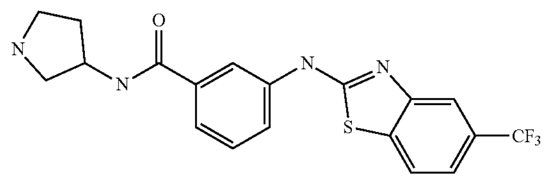 [SMILES: O=C(NC1CCNC1)c1cccc(Nc2nc3cc(C(F)(F)F)ccc3s2)c1] | 503 | 3-((5-trifluoromethylbenzo[d]thiazol-2-yl)amino)-N-(pyrrolidin-3-yl)benzamide |
| 354 | 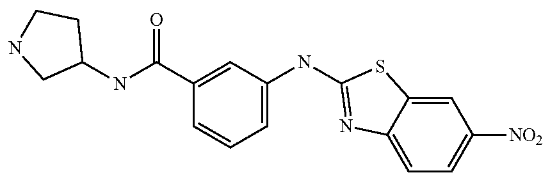 [SMILES: O=C(NC1CCNC1)c1cccc(Nc2nc3ccc([N+](=O)[O-])cc3s2)c1] | 504 | 3-((6-nitrobenzo[d]thiazol-2-yl)amino)-N-(pyrrolidin-3-yl)benzamide |
| 355 | 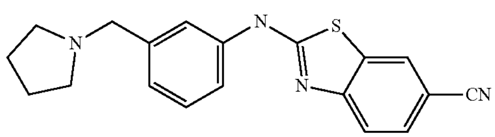 [SMILES: N#Cc1ccc2nc(Nc3cccc(CN4CCCC4)c3)sc2c1] | 505 | 2-(3-(pyrrolidin-1-ylmethyl)phenylamino)-6-cyanobenzo[d]thiazole |
| 356 | 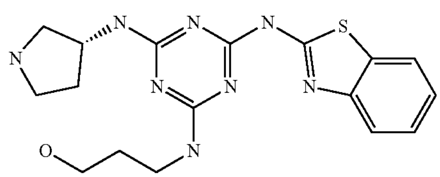 [SMILES: OCCCNc1nc(Nc2nc3ccccc3s2)nc(N[C@@H]2CCNC2)n1] | 506 | (R)-2-(benzo[d]thiazol-2-ylamino)-4-(3-hydroxypropylamino)-6-(pyrrolidin-3-ylamino)-1,3,5-triazine |
| 357 | 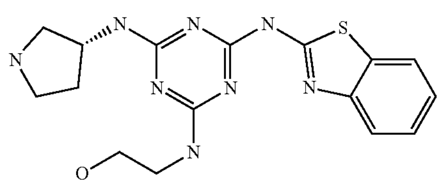 [SMILES: OCCNc1nc(Nc2nc3ccccc3s2)nc(N[C@@H]2CCNC2)n1] | 507 | (R)-2-(benzo[d]thiazol-2-ylamino)-4-(2-hydroxyethylamino)-6-(pyrrolidin-3-ylamino)-1,3,5-triazine |
| 358 | 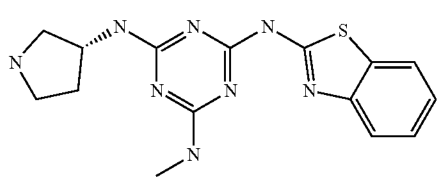 [SMILES: CNc1nc(Nc2nc3ccccc3s2)nc(N[C@@H]2CCNC2)n1] | 508 | (R)-2-(benzo[d]thiazol-2-ylamino)-4-methylamino-6-(pyrrolidin-3-ylamino)-1,3,5-triazine |

TABLE 3-continued

| E.g. | Structure | Cmpd | Name |
|---|---|---|---|
| 359 | 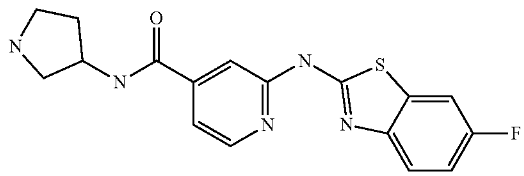 [SMILES: O=C(NC1CCNC1)c1ccnc(Nc2nc3ccc(O)cc3s2)c1] | 509 | 2-((6-fluorobenzo[d]thiazol-2-yl)amino)-N-(pyrrolidin-3-yl)isonicotinamide |
| 360 | 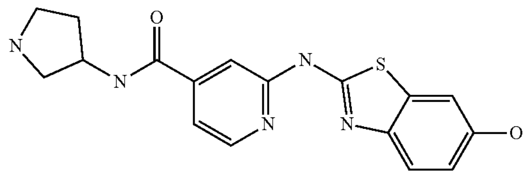 | 510 | 2-((6-hydroxybenzo[d]thiazol-2-yl)amino)-N-(pyrrolidin-3-yl)isonicotinamide |
| 361 | 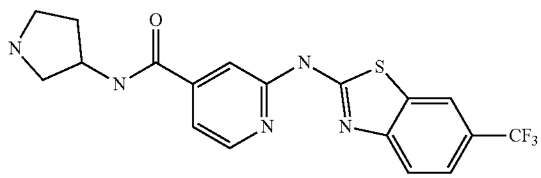 [SMILES: O=C(NC1CCNC1)c1ccnc(Nc2nc3ccc(C(F)(F)F)cc3s2)c1] | 511 | 2-((6-trifluoromethylbenzo[d]thiazol-2-yl)amino)-N-(pyrrolidin-3-yl)isonicolinamide |
| 362 | 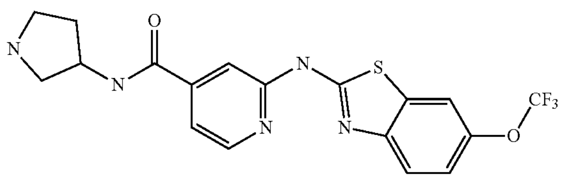 [SMILES: O=C(NC1CCNC1)c1ccnc(Nc2nc3ccc(OC(F)(F)F)cc3s2)c1] | 512 | 2-((6-trifluoromethoxybenzo[d]thiazol-2-yl)amino)-N-(pyrrolidin-3-yl)isonicotinamide |
| 363 | 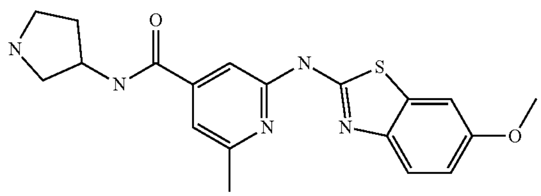 [SMILES: COc1ccc2nc(Nc3cc(C(=O)NC4CCNC4)cc(C)n3)sc2c1] | 513 | 2-((6-methoxybenzo[d]thiazol-2-yl)amino)-6-methyl-N-(pyrrolidin-3-yl)isonicolinamide |
| 364 | 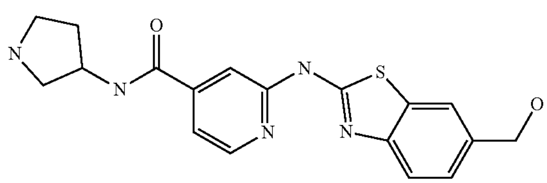 [SMILES: O=C(NC1CCNC1)c1ccnc(Nc2nc3ccc(CO)cc3s2)c1] | 514 | 2-((6-hydroxymethylbenzo[d]thiazol-2-yl)amino)-N-(pyrrolidin-3-yl)isonicolinamide |
| 365 | 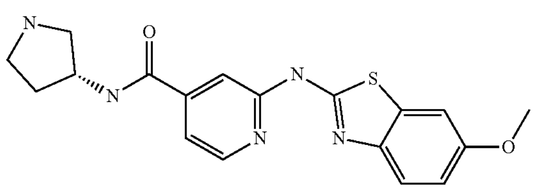 [SMILES: COc1ccc2nc(Nc3cc(C(=O)N[C@@H]4CCNC4)ccn3)sc2c1] | 515 | (R)-2-((6-methoxybenzo[d]thiazol-2-yl)amino)-N-(pyrrolidin-3-yl)isonicotinamide |
| 366 | 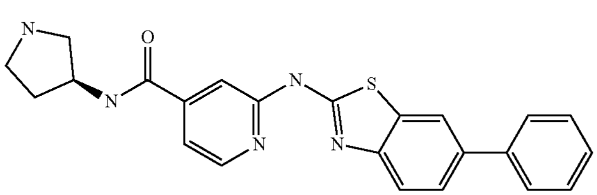 [SMILES: O=C(N[C@H]1CCNC1)c1ccnc(Nc2nc3ccc(-c4ccccc4)cc3s2)c1] | 516 | (S)-2-((6-phenylbenzo[d]thiazol-2-yl)amino)-N-(pyrrolidin-3-yl)isonicolinamide |

TABLE 3-continued

| E.g. | Cmpd | Name |
|---|---|---|
| 367 | 517 | (S)-2-((6-methylsulfonylbenzo[d]thiazol-2-yl)amino)-N-(pyrrolidin-3-yl)isonicotinamide |
| 368 | 518 | 2-((quinolin-2-yl)amino)-N-(pyrrolidin-3-yl)isonicotinamide |
| 369 | 519 | (S)-2-((6-cyanoquinolin-2-yl)amino)-N-(pyrrolidin-3-yl)isonicotinamide |
| 370 | 520 | (R)-2-((6-N-methyl-N-(2-methoxyethyl)benzo[d]thiazol-2-yl)amino)-N-(pyrrolidin-3-yl)isonicotinamide |
| 371 | 521 | (R)-2-((6-morpholinobenzo[d]thiazol-2-yl)amino)-N-(pyrrolidin-3-yl)isonicotinamide |
| 372 | 522 | 2-((6-(1H-pyrazol-4-yl)benzo[d]thiazol-2-yl)amino)-N-(pyrrolidin-3-yl)-4-pyrimidinecarboxamide |
| 373 | 523 | 5-((6-(1H-pyrazol-4-yl)benzo[d]thiazol-2-yl)amino)-N-(pyrrolidin-3-yl)nicotinamide |
| 374 | 524 | 2-((6-bromobenzo[d]thiazol-2-yl)amino)-4-(N-methyl-N-(2-methoxyethyl)aminomethyl)pyridine |
| 375 | 525 | 2-((6-bromobenzo[d]thiazol-2-yl)amino)-4-(morpholinomethyl)pyridine |

TABLE 3-continued

| E.g. | Structure | Cmpd | Name |
|---|---|---|---|
| 376 | 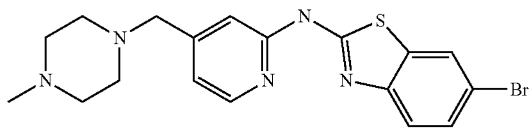 [SMILES: CN1CCN(Cc2ccnc(Nc3nc4ccc(Br)cc4s3)c2)CC1] | 526 | 2-((6-bromobenzo[d]thiazol-2-yl)amino)-4-(4-methylpiperazinomethyl)pyridine |
| 377 | 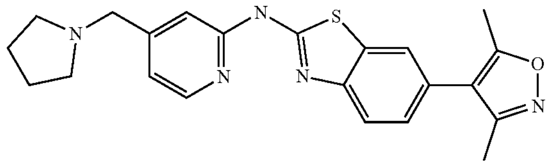 | 527 | 2-((6-(3,5-dimethylisoxazol-4-yl)benzo[d]thiazol-2-yl)amino)-4-(pyrrolidin-1-ylmethyl)pyridine |
| 378 | 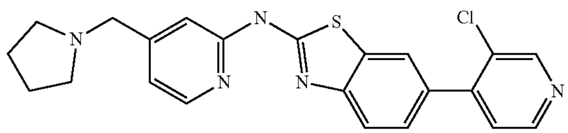 [SMILES: Clc1cnccc1-c1ccc2nc(Nc3cc(CN4CCCC4)ccn3)sc2c1] | 528 | 2-((6-(3-chloropyridin-4-yl)benzo[d]thiazol-2-yl)amino)-4-(pyrrolidin-1-ylmethyl)pyridine |
| 379 | 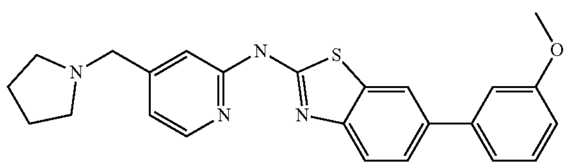 [SMILES: COc1cccc(-c2ccc3nc(Nc4cc(CN5CCCC5)ccn4)sc3c2)c1] | 529 | 2-((6-(3-methoxyphenyl)benzo[d]thiazol-2-yl)amino)-4-(pyrrolidin-1-ylmethyl)pyridine |
| 380 | 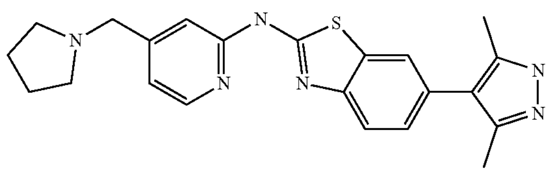 | 530 | 2-((6-(3,5-dimethylpyrazol-4-yl)benzo[d]thiazol-2-yl)amino)-4-(pyrrolidin-1-ylmethyl)pyridine |
| 381 | 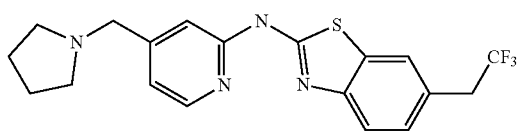 [SMILES: FC(F)(F)Cc1ccc2nc(Nc3cc(CN4CCCC4)ccn3)sc2c1] | 531 | 2-((6-(2,2,2-trifluoroethyl)benzo[d]thiazol-2-yl)amino)-4-(pyrrolidin-1-ylmethyl)pyridine |
| 382 | 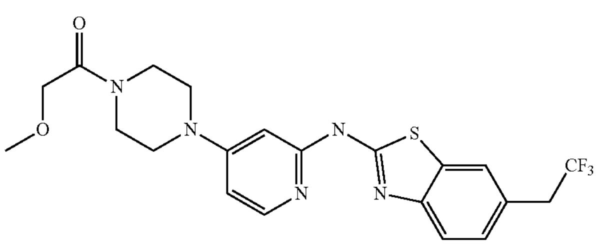 [SMILES: COCC(=O)N1CCN(c2ccnc(Nc3nc4ccc(CC(F)(F)F)cc4s3)c2)CC1] | 532 | 2-((6-(2,2,2-trifluoroethyl)benzo[d]thiazol-2-yl)amino)-4-(4-methoxyacetylpiperazin-1-yl)pyridine |
| 383 | 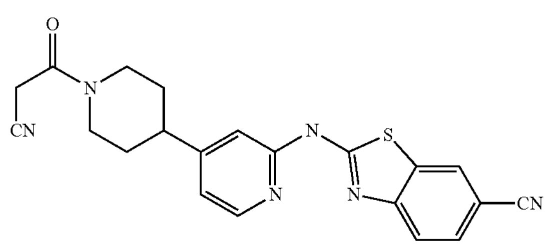 [SMILES: N#CCC(=O)N1CCC(c2ccnc(Nc3nc4ccc(C#N)cc4s3)c2)CC1] | 533 | 2-((6-cyanobenzo[d]thiazol-2-yl)amino)-4-(1-cyanoacetylpiperidin-4-yl)pyridine |

TABLE 3-continued

| E.g. | Cmpd | Name |
|---|---|---|
| 384 | 534 | 2-((6-cyanobenzo[d]thiazol-2-yl)amino)-4-(1-cyanomethylpiperidin-4-yl)pyridine |
| 385 | 535 | 2-((6-(imidazol-1-yl)benzo[d]thiazol-2-yl)amino)-4-hydroxymethylpyridine |
| 386 | 536 | 2-((6-cyanobenzo[d]thiazol-2-yl)amino)-4-(1-(4-methoxyphenyl)acetylpiperidin-4-yl)pyridine |
| 387 | 537 | 2-((6-cyanobenzo[d]thiazol-2-yl)amino)-4-(1-(3-cyclopentyl-1-oxopropyl)piperidin-4-yl)pyridine |
| 388 | 538 | 2-((6-cyanobenzo[d]thiazol-2-yl)amino)-4-(1-(1-oxopropyl)piperidin-4-yl)pyridine |
| 389 | 539 | 2-((6-cyanobenzo[d]thiazol-2-yl)amino)-4-(1-cyclopropylcarbonylpiperidin-4-yl)pyridine |
| 390 | 540 | 2-((6-cyanobenzo[d]thiazol-2-yl)amino)-4-(1-trifluoroacetylpiperidin-4-yl)pyridine |

TABLE 3-continued

| E.g. | Structure | Cmpd | Name |
|---|---|---|---|
| 391 | 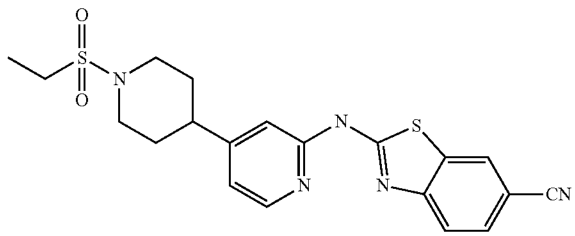 [SMILES: CCS(=O)(=O)N1CCC(c2ccnc(Nc3nc4ccc(C#N)cc4s3)c2)CC1] | 541 | 2-((6-cyanobenzo[d]thiazol-2-yl)amino)-4-(1-ethylsulfonylpiperidin-4-yl)pyridine |
| 392 | 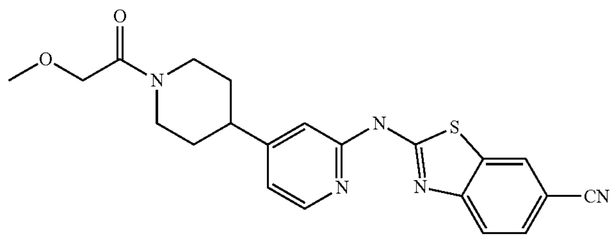 [SMILES: COCC(=O)N1CCC(c2ccnc(Nc3nc4ccc(C#N)cc4s3)c2)CC1] | 542 | 2-((6-cyanobenzo[d]thiazol-2-yl)amino)-4-(1-methoxyacetylpiperidin-4-yl)pyridine |
| 393 | 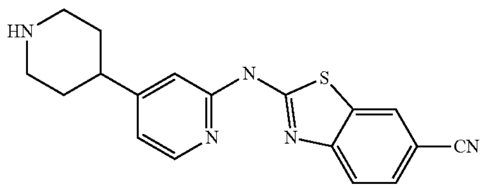 [SMILES: N#Cc1ccc2nc(Nc3cc(C4CCNCC4)ccn3)sc2c1] | 543 | 2-((6-cyanobenzo[d]thiazol-2-yl)amino)-4-(piperidin-4-yl)pyridine |
| 394 | 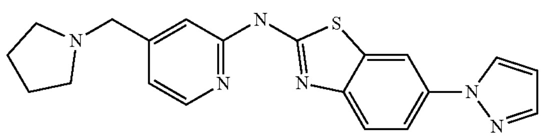 [SMILES: c1cnn(-c2ccc3nc(Nc4cc(CN5CCCC5)ccn4)sc3c2)c1] | 544 | 2-((6-(pyrazol-1-yl)benzo[d]thiazol-2-yl)amino)-4-(pyrrolidin-1-ylmethyl)pyridine |
| 395 | 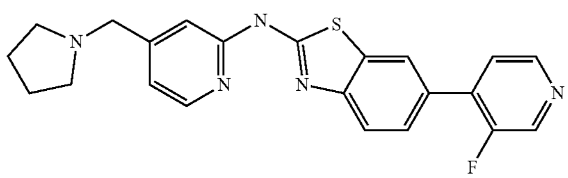 [SMILES: Fc1cnccc1-c1ccc2nc(Nc3cc(CN4CCCC4)ccn3)sc2c1] | 545 | 2-((6-(3-fluoropyridin-4-yl)benzo[d]thiazol-2-yl)amino)-4-(pyrrolidin-1-ylmethyl)pyridine |
| 396 | 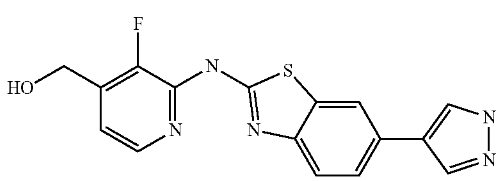 [SMILES: OCc1ccnc(Nc2nc3ccc(-c4cn[nH]c4)cc3s2)c1F] | 546 | 2-((6-(pyrazol-4-yl)benzo[d]thiazol-2-yl)amino)-4-hydroxymethyl-3-fluoropyridine |
| 397 | 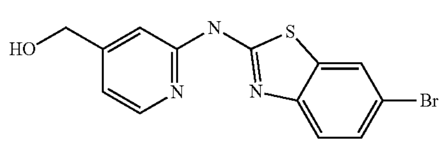 [SMILES: OCc1ccnc(Nc2nc3ccc(Br)cc3s2)c1] | 547 | 2-((6-bromobenzo[d]thiazol-2-yl)amino)-4-hydroxymethylpyridine |
| 398 | 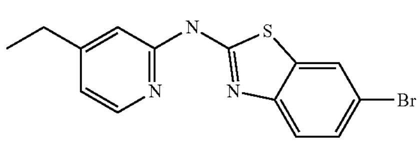 [SMILES: CCc1ccnc(Nc2nc3ccc(Br)cc3s2)c1] | 548 | 2-((6-bromobenzo[d]thiazol-2-yl)amino)-4-ethylpyridine |
| 399 | 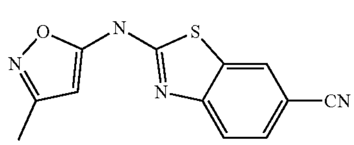 [SMILES: Cc1cc(Nc2nc3ccc(C#N)cc3s2)on1] | 549 | 5-((6-cyanobenzo[d]thiazol-2-yl)amino)-3-methylisoxazole |

TABLE 3-continued

| E.g. | Cmpd | Name |
|---|---|---|
| 400 | 550 | 2-((6-cyanobenzo[d]thiazol-2-yl)amino)-5-methyl-4-phenylthiazole |
| 401 | 551 | 2-((6-cyanobenzo[d]thiazol-2-yl)amino)-5-(4-methoxyphenyl)-1,3,4-thiadiazol |
| 402 | 552 | 2-((6-(oxazol-5-yl)benzo[d]thiazol-2-yl)amino)-4-(4-(2-methoxyethyl)piperazin-1-yl)pyridine |
| 403 | 553 | 2-((6-(2-methyl-1,3,4-oxadiazol-5-yl)benzo[d]thiazol-2-yl)amino)-4-ethylpyridine |
| 404 | 554 | 2-(3-hydroxymethylphenyl)amino-6-cyanobenzo[d]thiazole |
| 405 | 555 | 2-((6-(1,3,4-oxadiazol-2-yl)benzo[d]thiazol-2-yl)amino)-4-ethylpyridine |
| 406 | 556 | 2-((6-(1,3,4-thiadiazol-2-yl)benzo[d]thiazol-2-yl)amino)-4-ethylpyridine |
| 407 | 557 | 2-((6-cyanobenzo[d]thiazol-2-yl)amino)-4-(pyrrolidin-1-ylmethyl) pyridine |
| 408 | 558 | 2-((6-cyanobenzo[d]thiazol-2-yl)amino)-4-(pyrrolidin-1-ylthiocarbonyl) pyridine |
| 409 | 559 | 2-(3,5-dimethoxymethylphenyl)amino-6-cyanobenzo[d]thiazole |

TABLE 3-continued

| E.g. | Structure | Cmpd | Name |
|---|---|---|---|
| 410 | 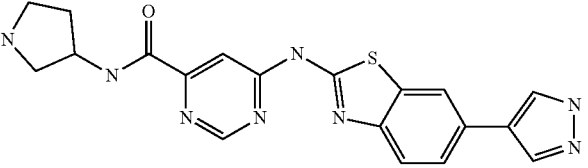 | 560 | 4-((6-(1H-pyrazol-4-yl)benzo[d]thiazol-2-yl)amino)-N-(pyrrolidin-3-yl)-6-pyrimidinecarboxamide |
| 411 | 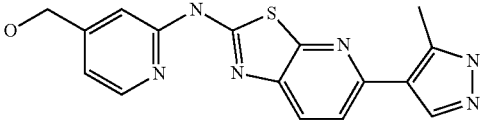 [SMILES: Cc1[nH]ncc1-c1ccc2nc(Nc3cc(CO)ccn3)sc2n1] | 561 | 5-(5-methyl-1H-pyrazol-4-yl)-2-(4-hydroxymethylpyridin-2-ylamino)thiazolo[5,4-b]pyridine |
| 412 | 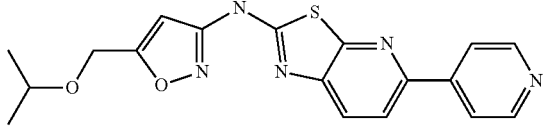 [SMILES: CC(C)OCc1cc(Nc2nc3ccc(-c4ccncc4)nc3s2)no1] | 562 | 5-(pyridin-4-yl)-2-(5-isopropyloxymethylisoxazol-3-ylamino)thiazolo[5,4-b]pyridine |
| 413 | 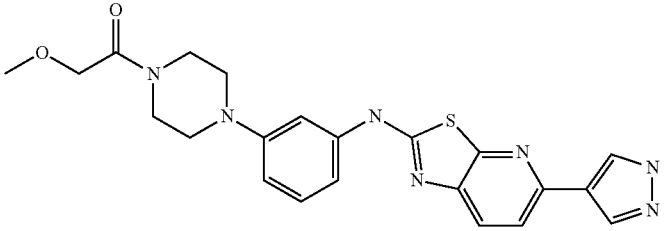 [SMILES: COCC(=O)N1CCN(c2cccc(Nc3nc4ccc(-c5cn[nH]c5)nc4s3)c2)CC1] | 563 | 5-(1H-pyrazol-4-yl)-2-(3-(4-methoxyacetylpiperazin-1-yl)phenyl)amino)thiazolo[5,4-b]pyridine |
| 414 | 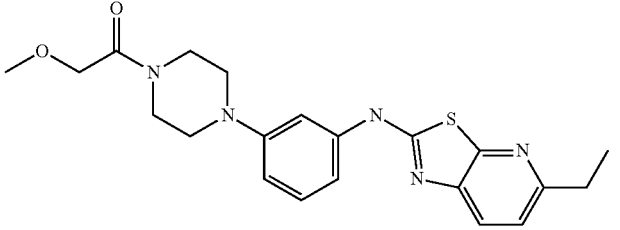 [SMILES: CCc1ccc2nc(Nc3cccc(N4CCN(C(=O)COC)CC4)c3)sc2n1] | 564 | 5-ethyl-2-(3-(4-methoxyacetylpiperazin-1-ylphenyl)amino)thiazolo[5,4-b]pyridine |
| 415 | 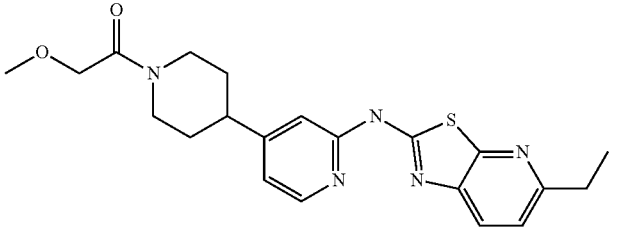 [SMILES: CCc1ccc2nc(Nc3cc(C4CCN(C(=O)COC)CC4)ccn3)sc2n1] | 565 | 5-ethyl-2-(4-(1-methoxyacetylpiperidin-4-yl)pyridin-2-yl)amino)thiazolo[5,4-b]pyridine |
| 416 | 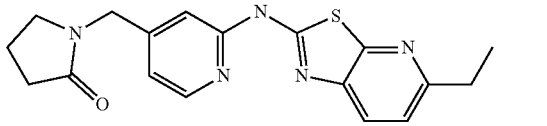 [SMILES: CCc1ccc2nc(Nc3cc(CN4CCCC4=O)ccn3)sc2n1] | 566 | 5-ethyl-2-(4-(pyrrolidon-1-yl)pyridin-2-yl)amino)thiazolo[5,4-b]pyridine |
| 417 | 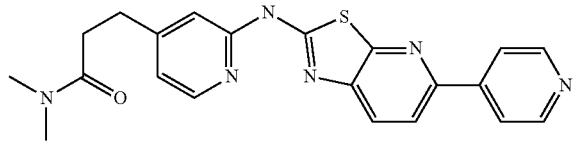 [SMILES: CN(C)C(=O)CCc1ccnc(Nc2nc3ccc(-c4ccncc4)nc3s2)c1] | 567 | 5-(pyridine-4-yl)-2-(4-(3-dimethylamino-3-oxopropyl)pyridin-2-yl)amino)thiazolo[5,4-b]pyridine |

TABLE 3-continued

| E.g. | Structure | Cmpd | Name |
|---|---|---|---|
| 418 | 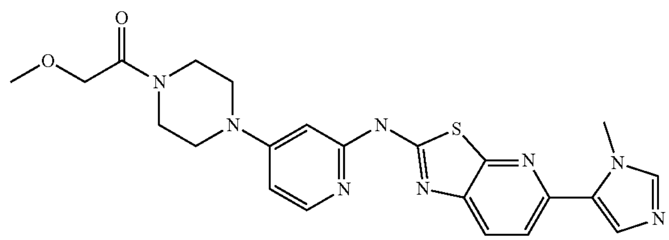 | 568 | 5-(1-methylimidazol-5-yl)-2-(4-(4-methoxyacetylpiperazin-1-ylpyridin-2-yl)amino)thiazolo[5,4-b]pyridine |
| 419 | 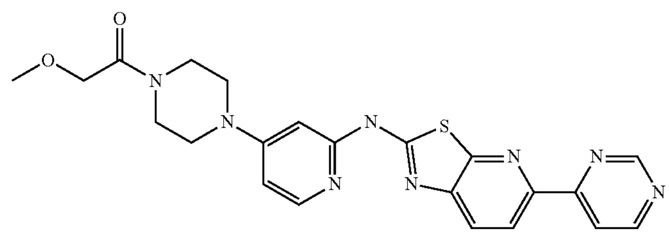 [SMILES: COCC(=O)N1CCN(c2ccnc(Nc3nc4ccc(-c5ccncn5)nc4s3)c2)CC1] | 569 | 5-(pyrimidin-4-yl)-2-(4-(4-methoxyacetylpiperazin-1-ylpyridin-2-yl)amino)thiazolo[5,4-b]pyridine |
| 420 | 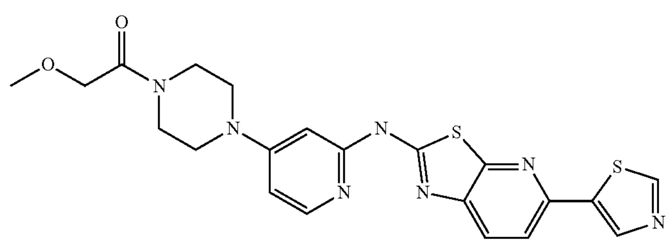 [SMILES: COCC(=O)N1CCN(c2ccnc(Nc3nc4ccc(-c5cncs5)nc4s3)c2)CC1] | 570 | 5-(thiazol-5-yl)-2-(4-(4-methoxyacetylpiperazin-1-ylpyridin-2-yl)amino)thiazolo[5,4-b]pyridine |
| 421 | 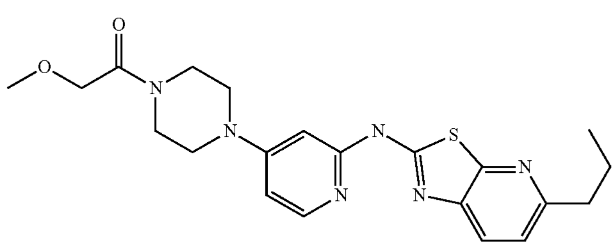 [SMILES: CCCc1ccc2nc(Nc3cc(N4CCN(C(=O)COC)CC4)ccn3)sc2n1] | 571 | 5-propyl-2-(4-(4-methoxyacetylpiperazin-1-ylpyridin-2-yl)amino)thiazolo[5,4-b]pyridine |
| 422 | 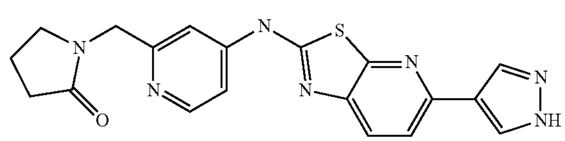 [SMILES: O=C1CCCN1Cc1cc(Nc2nc3ccc(-c4cn[nH]c4)nc3s2)ccn1] | 572 | 5-(1H-pyrazol-4-yl)-2-(2-pyrrolidon-1-ylmethylpyridin-4-yl)amino)thiazolo[5,4-b]pyridine |
| 423 | 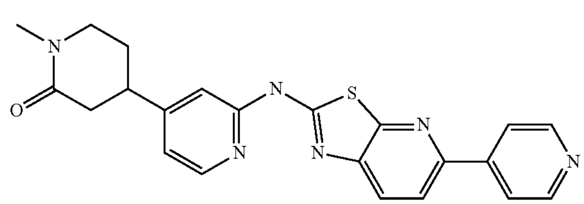 [SMILES: CN1CCC(c2ccnc(Nc3nc4ccc(-c5ccncc5)nc4s3)c2)CC1=O] | 573 | 5-(pyridin-4-yl)-2-(4-(1-methyl-2-oxopiperidin-4-ylpyridin-2-yl)amino)thiazolo[5,4-b]pyridine |
| 424 | 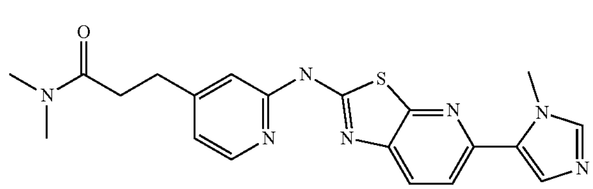 [SMILES: CN(C)C(=O)CCc1ccnc(Nc2nc3ccc(-c4cncn4C)nc3s2)c1] | 574 | 5-(1-methylimidazol-5-yl)-2-(4-(2-dimethylaminocarbonylethyl)pyridin-2-yl)amino)thiazolo[5,4-b]pyridine |

TABLE 3-continued

| E.g. | Cmpd | Name |
|---|---|---|
| 425 | 575 | 5-(pyridine-4-yl)-2-(4-(4-methoxyacetylpiperazin-1-ylpyridin-2-yl)amino)oxazolo[5,4-b]pyridine |
| 426 | 576 | 2-((6-cyanobenzo[d]thiazol-2-yl)amino)-4-(1-phenylcarbonylpiperidin-4-yl)pyridine |
| 427 | 577 | 6-cyano-2-(4-(4-methoxyacetyl-piperazin-1-yl)pyridin-2-ylamino)imidazo[1,2-a]pyridine |
| 428 | 578 | 6-cyano-2-(4-(4-(2-methoxyethyl)piperazin-1-yl)pyridin-2-ylamino)imidazo[1,2-a]pyridine |
| 429 | 579 | 6-(1H-pyrazol-4-yl)-2-(4-morpholinopyridin-2-ylamino)imidazo[1,2-a]pyridine |
| 430 | 580 | 5-(pyridin-3-yl)-2-(4-(piperazin-1-ylmethylpyridin-2-yl)amino)thiazolo[5,4-d]pyridine |

Example 431

Inhibition Assay

The following assay is useful for evaluating test compounds for inhibition of IRAK-1 or IRAK-4 kinase activity. A 96-well polystyrene microtiter plates are coated with neutravidin for IRAK-1 or streptavidin for IRAK-4 (10 mg/mL in PBS, overnight at 4° C.). The coating solution is removed and in 80 μL/well, a kinase reaction mixture is added (for IRAK-1: 20 mM Tris-HCl, pH 7.5, 10 mM MgCl$_2$, 2 mM EGTA, 1 mM NaF, 0.5 mM benzamidine, 1 mM DTT, 3 μM ATP, 1 mM of biotinylated substrate peptide bio-ARFSRFAGSSPSQSSMVAR, sequence derived from IRAK-1; for IRAK-4: 20 mM Tris-HCl, pH 7.5, 10 mM MgCl$_2$, 2 mM EGTA, 1 mM NaF, 0.5 mM benzamidine, 1 mM DTT, 10% glycerol, 10 μM ATP, 1 mM of biotinylated substrate peptide bio-RRRVTSPARRS, sequence derived from GFAP).

At 10 μL/well in DMSO test compounds are added covering a final concentration range from 1 nM to 30 mM. Recombinant, full-length IRAK-1 or IRAK-4 enzyme (baculovirus expression system) is added in 10 μL buffer containing 20 mM Tris-HCl, pH 7.5, 2 mM EGTA, 0.5 mM benzamidine, 1 mM DTT, 10 mM MgCl$_2$, and glycerol 10% (IRAK-4 only) to initiate the kinase reaction. The reaction mixture is incubated at room temperature for 60 min on a shaker. During this incubation the substrate peptide is being phosphorylated by the kinase and gets captured onto the surface of the wells by neutravidin or streptavidin, respectively. The plate is washed 3× with 150 μL distilled water to terminate the reaction and remove components of the reaction mixture. A conventional chemiluminescent ELISA detection technique is initiated by adding 100 μL/well primary antibody (monoclonal antibody YC10, generated to recognize the phosphorylated epitope in the substrate peptide; use at 1:20,000 dilution for IRAK-1 and 1:10,000 dilution for IRAK-4) premixed with horseradish peroxidase (HRP) conjugated anti-mouse secondary antibody (commercially available from several sources; use at 1:10,000 dilution) in PBS containing 2% BSA. The solution is incubated at room temperature for 40 min on a shaker, then washed 3× with 150 μL of water. 100 μL 10× diluted SuperSignal HRP substrate (from Pierce) is added and after 5 min incubation the chemiluminescent signal is captured by a Labsystems LuminoSkan luminometer. The point of 50% inhibition of IRAK-1 or IRAK-4 enzyme activity ($IC_{50}$) is determined. Table 4 summarizes data obtained using an assay substantially similar to the foregoing method (Compound: Cmpd).

TABLE 4

| Cmpd | $EC_{50}$ | Cmpd | $EC_{50}$ | Cmpd | $EC_{50}$ | Cmpd | $EC_{50}$ |
|---|---|---|---|---|---|---|---|
| 101 | A | 110 | A | 120 | A | 130 | A |
| 137 | A | 150 | A | 160 | A | 170 | A |
| 180 | A | 190 | A | 200 | A | 210 | A |
| 220 | A | 230 | A | 240 | A | 250 | A |
| 260 | A | 270 | A | 280 | A | 290 | A |
| 300 | A | 310 | A | 320 | A | 330 | A |
| 340 | A | 350 | A | 360 | A | 370 | A |
| 380 | A | 390 | A | 401 | A | 410 | A |
| 420 | A | 430 | A | 439 | A | 484 | B |
| 490 | A | 500 | A | 510 | B | 521 | B |
| 530 | B | 540 | A | 553 | B | 560 | B |
| 570 | A | 580 | B | | | | |

It is to be understood that both the foregoing general description and detailed description are exemplary and explanatory only and are not restrictive of the embodiments claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting. The term "comprising" as used herein is synonymous with "including," "containing," or "characterized by," and is inclusive or open-ended and does not exclude additional, unrecited elements or method steps.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method of preparing a compound of Formula (IV):

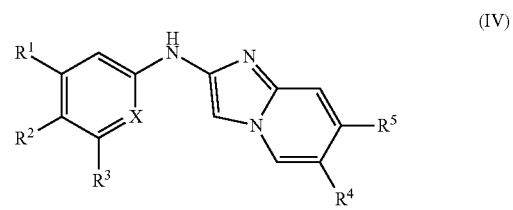

wherein:

X is N;

$R^1$ is selected from hydrogen, halogen, $OR^6$, CN, $NR^7R^8$, $CH_2OR^6$, $CH_2NR^7R_8$, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, $CO_2R^6$, $CONR^7R^8$, $SO_3R^6$, and $SO_2NR^7R^8$;

$R^2$, $R^3$ and $R^5$ are each hydrogen;

$R^4$ is selected from halogen, $OR^6$, CN, $NR^7R^8$, $CH_2OR^6$, an optionally substituted aryl, an optionally substituted three to nine membered heteroaryl, an optionally substituted three to nine membered non-aromatic ring, an optionally substituted three to nine membered carbocycle, an optionally substituted $C_1$-$C_6$ alkyl, an optionally substituted $C_1$-$C_6$ haloalkyl, an optionally substituted $C_1$-$C_6$ alkenyl, an optionally substituted $C_1$-$C_6$ alkynyl, $CO_2R^6$, $SO_3R^6$, $SO_2R^6$ and $SO_2NR^7R^8$;

each $R^6$ is independently selected from an optionally substituted aryl, an optionally substituted three to nine membered heteroaryl, and an optionally substituted three to nine membered non-aromatic ring, each optionally fused with a substituted aryl or a substituted three to nine membered heteroaryl, hydrogen, an optionally substituted $C_1$-$C_{10}$ alkyl;

each $R^7$ and $R^8$ is independently selected from an optionally substituted aryl, an optionally substituted three to nine membered heteroaryl, an optionally substituted three to nine membered non-aromatic ring, each optionally fused with a substituted aryl or a substituted three to nine membered heteroaryl, hydrogen, an optionally substituted $C_1$-$C_{10}$ alkyl, an optionally substituted $C_1$-$C_{10}$ haloalkyl, an optionally substituted $C_1$-$C_{10}$ alkenyl, and an optionally substituted $C_1$-$C_{10}$ alkynyl, or $R^7$ and $R^8$ are linked to form an optionally substituted three to nine membered non-aromatic ring; and each optionally substituted group is either unsubstituted or substituted with one or more groups independently selected from alkyl, alkenyl, alkynyl, haloalkyl, heterohaloalkyl, aryl, arylalkyl, three to nine membered heteroaryl, three to nine membered non-aromatic ring, hydroxy, alkoxy, aryloxy, mercapto, alkylthio, arylthio, cyano, halo, —C(═O)R, —C(═S)R, —O(C═O)NR$_2$, ROC(═O)NH—, —O(C═S)NR$_2$, ROC(═S)NH—, —(C═O)NR$_2$, RC(═O)NH—, —S(═O)$_2$NR, RS(═O)$_2$NH—, —C(═O)OR, RC(═O)O isocyanato, thiocyanato, isothiocyanato, nitro, silyl, trihalomethanesulfonyl, ═O, ═S, and amino, wherein each R is independently selected from the group consisting of alkyl, cycloalkyl, aryl, three to nine membered heteroaryl, and three to nine membered non-aromatic ring; wherein the method comprises:

coupling a 2-halopyridine with an aminoimidazopyridine.

2. The method of claim 1, wherein the 2-halopyridine has the structure:

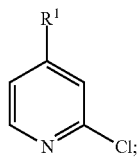

and
the aminoimidazopyridine has the structure:

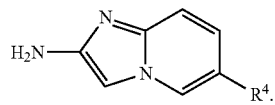

3. The method of claim 1, wherein the coupling is performed in the presence of a palladium catalyst and a base.

4. The method of claim 1, wherein $R^1$ is $NR^7R^8$, $CH_2NR^7R^8$, or an optionally substituted $C_1$-$C_6$ alkyl.

5. The method of claim 4, wherein $R^1$ is selected from $NR^7R^8$, or $CH_2NR^7R^8$.

6. The method of claim 1, wherein $R^4$ is selected from an optionally substituted heteroaryl selected from $C_3$-$C_6$ cycloalkyl, $C_2$-$C_6$ alkenyl, $C_2$-$C_6$ alkynyl, and an optionally substituted heteroaryl selected from pyridine, pyrazole, pyridazine, pyrimidine, wherein the heteroaryl is optionally substituted with 1-2 substituents selected from $C_1$-$C_6$ alkyl and CN.

7. The method of claim 1, wherein $R^4$ is selected from cyano, triazolyl, oxazolyl, isoxazolyl, imidazoyl, pyridyl, pyrazolyl, pyrimidinyl, pyridazinyl, and $C_1$-$C_6$ alkyl.

8. The method of claim 7, wherein $R^4$ is selected from pyridyl, pyrazolyl, pyrimidinyl, and pyridazinyl.

9. The method of claim 8, wherein $R^4$ is selected from pyridyl and pyrazolyl.

10. The method of claim 9, wherein $R^4$ is pyrazolyl.

11. The method of claim 1, wherein the compound is selected from the group consisting of:

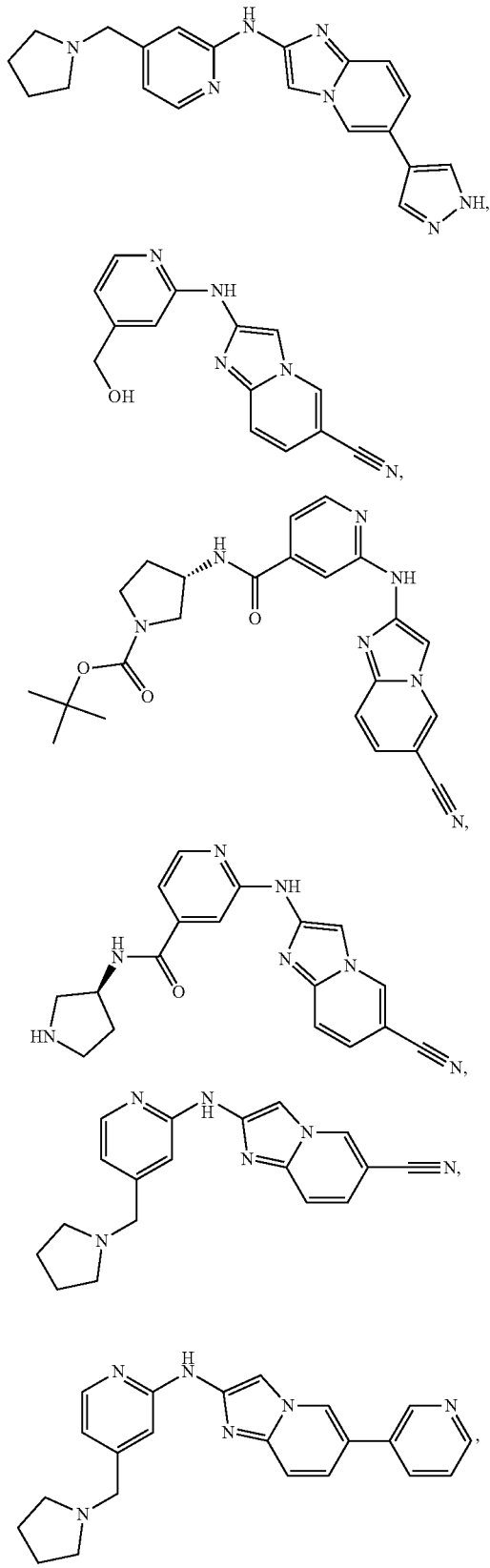

181
-continued
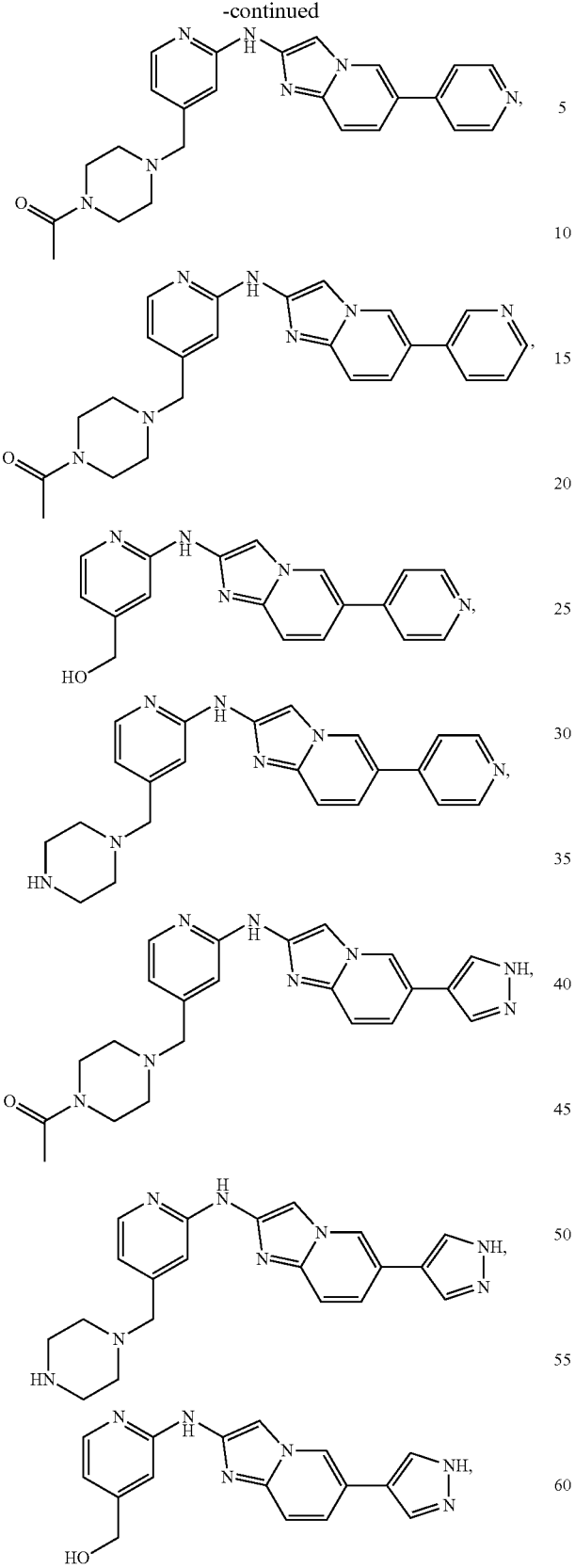
182
-continued
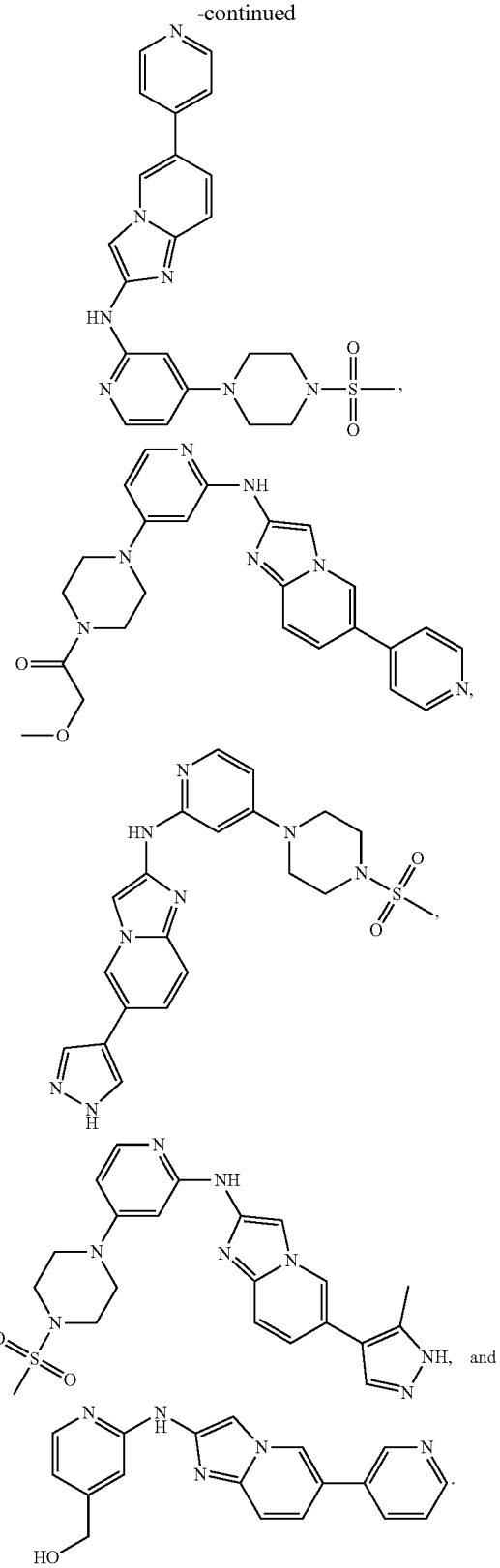
* * * * *

UNITED STATES PATENT AND TRADEMARK OFFICE
CERTIFICATE OF CORRECTION

PATENT NO. : 11,773,110 B2
APPLICATION NO. : 17/513093
DATED : October 3, 2023
INVENTOR(S) : Koc-Kan Ho et al.

It is certified that error appears in the above-identified patent and that said Letters Patent is hereby corrected as shown below:

On the Title Page

Page 2, Column 1 (Other Publications), Line 22, delete "3rd" and insert -- $3^{rd}$ --.

Page 2, Column 2 (Other Publications), Line 27, delete "forTh17Differentiation" and insert -- for Th17 Differentiation --.

Page 2, Column 2 (Other Publications), Line 40, delete "Diesases: Desinsitized" and insert -- Diseases: Desensitized --.

In the Specification

Column 3, Line 41, delete "imidazoyl," and insert -- imidazolyl, --.

Column 3, Line 41, delete "imidazoyl" and insert -- imidazolyl --.

Column 7, Line 1, delete "p Z" and insert -- Z --.

Column 8, Line 8 (approx.), delete "imidazoyl," and insert -- imidazolyl, --.

Column 8, Line 8 (approx.), delete "imidazoyl" and insert -- imidazolyl --.

Column 13, Line 29, delete "O—C" and insert -- O-C --.

Column 14, Line 43, delete "—S(=O) 13 R." and insert -- —S(=O)—R. --.

Column 18, Line 4 (approx.), delete "imidazoyl," and insert -- imidazolyl, --.

Column 18, Line 4 (approx.), delete "imidazoyl" and insert -- imidazolyl --.

Signed and Sealed this
Ninth Day of January, 2024

Katherine Kelly Vidal
*Director of the United States Patent and Trademark Office*

Page 1 of 4

Column 20, Line 7 (approx.), delete "imidazoyl" and insert -- imidazolyl --.

Column 20, Line 10, delete "imidazoyl" and insert -- imidazolyl --.

Column 20, Line 17 (approx.), delete "by" and insert -- be --.

Column 21, Line 3-11, delete " 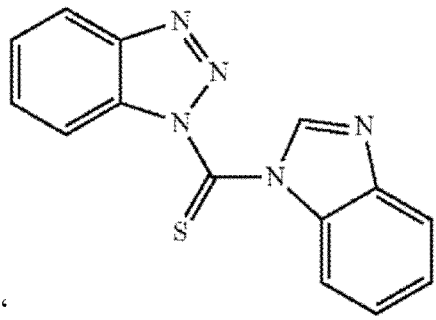 " and insert

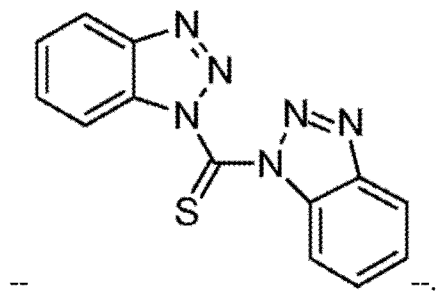

-- --.

Column 25, Line 26, delete "formulatory" and insert -- formulary --.

Column 27, Line 64-65, delete "compoistions" and insert -- compositions --.

Column 28, Line 1, delete "pseudophedrine," and insert -- pseudoephedrine, --.

Column 28, Line 2, delete "ephinephrine," and insert -- epinephrine, --.

Column 28, Line 45-46, delete "bezpiperylon," and insert -- benzpiperylone, --.

Column 28, Line 51, delete "j)" and insert -- (j) --.

Column 28, Line 58, delete "meglinatide)," and insert -- meglinitide), --.

Column 28, Line 62, delete "(1)" and insert -- (l) --.

Column 28, Line 63, delete "β;" and insert -- β); --.

Column 29, Line 35 (approx.), delete "methotrextate," and insert -- methotrexate, --.

Column 29, Line 55 (approx.), delete "benzo [d]" and insert -- benzo[d] --.

CERTIFICATE OF CORRECTION (continued)
U.S. Pat. No. 11,773,110 B2

Column 30, Line 25, delete "1H NMR" and insert -- $^1$HNMR --.

Column 30, Line 66-67, delete "benzo [d]" and insert -- benzo[d] --.

Column 31, Line 24 (approx.), delete "N-(4-4(Tert-butyldimethylsilyl)oxy)methyppyridin" and insert -- N-(4-(((Tert-butyldimethylsilyl)oxy)methyl)pyridin --.

Column 31, Line 31 (approx.), delete "benzo [d]" and insert -- benzo[d] --.

Column 31, Line 42 (approx.), delete "$R^1$=$CH_2$" and insert -- $R^1$=$CH_2$. --.

Column 32, Line 7, delete "(chloromethyppyridin-" and insert -- (chloromethyl)pyridin- --.

Column 32, Line 16 (approx.), delete "$POCl_3$" and insert -- pyrolidine --.

Column 32, Line 55 (approx.), delete "δ8.83" and insert -- δ 8.83 --.

Column 49-50, Line 10 (approx., Table 1-continued), delete "methylamino)-" and insert -- methylamino- --.

Column 137-138, Line 5 (approx., Table 1-continued), delete "yl)-" and insert -- yl- --.

Column 147, Line 29 (approx.), delete "benzo [d]" and insert -- benzo[d] --.

Column 147, Line 30 (approx.), delete "IL" and insert -- II, --.

Column 149, Line 7, delete "$R^1$=$CH_2$" and insert -- $R^1$=$CH_2$. --.

Column 149-150, Line 2 (Table 2), delete "hydoxymethyl" and insert -- hydroxymethyl --.

Column 151-152, Line 5 (approx., Table 2-continued), delete "carboxylale" and insert -- carboxylate --.

Column 159-160, Line 8 (approx., Table 3-continued), delete "isonicolinamide" and insert -- isonicotinamide --.

Column 159-160, Line 14 (approx., Table 3-continued), delete "isonicolinamide" and insert -- isonicotinamide --.

Column 159-160, Line 17 (approx., Table 3-continued), delete "isonicolinamide" and insert -- isonicotinamide --.

Column 159-160, Line 23 (approx., Table 3-continued), delete "isonicolinamide" and insert -- isonicotinamide --.

Column 163-164, Line 22 (approx., Table 3-continued), delete "cyanoacetylpiperidin" and insert

CERTIFICATE OF CORRECTION (continued)
U.S. Pat. No. 11,773,110 B2

-- cyanomethylpiperidin --.

Column 169-170, Line 5 (approx., Table 3-continued), delete "thiadiazol" and insert -- thiadiazole --.

Column 171-172, Line 22 (approx., Table 3-continued), delete "amino)" and insert -- amino --.

Column 173-174, Line 15 (approx., Table 3-continued), delete "amino)" and insert -- amino --.

Column 173-174, Line 22 (approx., Table 3-continued), delete "amino)" and insert -- amino --.

Column 175-176, Line 18 (approx., Table 3-continued), delete "d]" and insert -- b] --.

In the Claims

Column 178, Line 34, Claim 1, delete "$CH_2NR^7R_8$," and insert -- $CH_2NR^7R^8$, --.

Column 179, Line 60, Claim 7, delete "imidazoyl," and insert -- imidazolyl, --.